(12) United States Patent
Heckel et al.

(10) Patent No.: US 8,853,193 B2
(45) Date of Patent: *Oct. 7, 2014

(54) THIENOPYRIMIDINES CONTAINING A SUBSTITUTED ALKYL GROUP FOR PHARMACEUTICAL COMPOSITIONS

(75) Inventors: Armin Heckel, Biberach (DE); Frank Himmelsbach, Mittelbiberach (DE); Joerg Kley, Mittelbiberach (DE); Thorsten Lehmann-Lintz, Ochsenhausen (DE); Norbert Redemann, Biberach (DE); Achim Sauer, Ravensburg-Torkenweiler (DE); Leo Thomas, Biberach (DE); Dieter Wiedenmayer, Biberach (DE); Phillip Black, Saffron Walden Essex (GB); Wesley Blackaby, Saffron Walden Essex (GB); Ian Linney, Saffron Walden Essex (GB); Matthias Austen, Goettingen (DE); John Danilewicz, Canterbury (GB); Martin Schneider, Goettingen (DE); Kay Schreiter, Goettingen (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 368 days.

This patent is subject to a terminal disclaimer.

(21) Appl. No.: 13/035,023

(22) Filed: Feb. 25, 2011

(65) Prior Publication Data

US 2011/0212103 A1    Sep. 1, 2011

(30) Foreign Application Priority Data

Feb. 26, 2010   (EP) .................................. 10154930

(51) Int. Cl.
| | | |
|---|---|---|
| *C07D 495/04* | (2006.01) | |
| *A61K 31/519* | (2006.01) | |
| *A61K 31/5377* | (2006.01) | |
| *A61K 31/56* | (2006.01) | |
| *A61P 29/00* | (2006.01) | |
| *A61P 35/00* | (2006.01) | |
| *A61P 25/28* | (2006.01) | |
| *A61P 13/12* | (2006.01) | |
| *A61K 31/395* | (2006.01) | |

(52) U.S. Cl.
CPC ................... *C07D 495/04* (2013.01)
USPC ........ 514/171; 544/278; 544/117; 424/158.1; 424/172.1; 514/260.1; 514/234.2

(58) Field of Classification Search
CPC .............. C07D 495/04; A61K 31/519
USPC ...................... 544/278; 514/260.1
See application file for complete search history.

(56) References Cited

U.S. PATENT DOCUMENTS

| | | | |
|---|---|---|---|
| 5,686,457 A | 11/1997 | Traxler et al. | |
| 6,096,749 A | 8/2000 | Traxler et al. | |
| 6,395,733 B1 | 5/2002 | Arnold et al. | |
| 6,784,174 B1 | 8/2004 | Cumming | |
| 8,071,607 B2 | 12/2011 | Coulter et al. | |
| 2001/0027197 A1 | 10/2001 | Bridges et al. | |
| 2003/0162795 A1 | 8/2003 | Munchhof et al. | |
| 2006/0020042 A1 | 1/2006 | McDonald et al. | |
| 2007/0099877 A1 | 5/2007 | Cai et al. | |
| 2009/0163520 A1 | 6/2009 | Coulter et al. | |
| 2010/0015708 A1 | 1/2010 | Quay et al. | |
| 2010/0056548 A1 | 3/2010 | Aicher et al. | |
| 2010/0143341 A1 | 6/2010 | Taylor et al. | |
| 2010/0247517 A1 | 9/2010 | Austen et al. | |
| 2011/0021203 A1 | 1/2011 | Yamada et al. | |
| 2011/0212102 A1 | 9/2011 | Lehmann-Lintz et al. | |
| 2011/0217311 A1 | 9/2011 | Lehmann-Lintz et al. | |
| 2011/0312908 A1* | 12/2011 | Gray et al. .................. 514/46 |
| 2012/0128686 A1 | 5/2012 | Austen et al. | |
| 2013/0056914 A1 | 3/2013 | Frankowski et al. | |

FOREIGN PATENT DOCUMENTS

| | | | |
|---|---|---|---|
| CA | 2038521 A1 | 9/1991 | |
| CH | 408945 A | 3/1966 | |
| DE | 3036390 A1 | 5/1982 | |
| DE | 248593 A1 | 8/1987 | |
| EP | 0447891 A1 | 9/1991 | |
| EP | 0452002 A2 | 10/1991 | |
| EP | 0682027 A1 | 11/1995 | |
| EP | 0729758 A2 | 9/1996 | |
| EP | 1724268 A1 | 11/2006 | |
| JP | 2005503345 A | 2/2005 | |

(Continued)

OTHER PUBLICATIONS

STN printout, downloaded Feb. 21, 2013.*

(Continued)

*Primary Examiner* — Susanna Moore
(74) *Attorney, Agent, or Firm* — Michael P. Morris; Edward S. Lazer

(57) ABSTRACT

The present invention relates to novel thienopyrimidine compounds of general formula

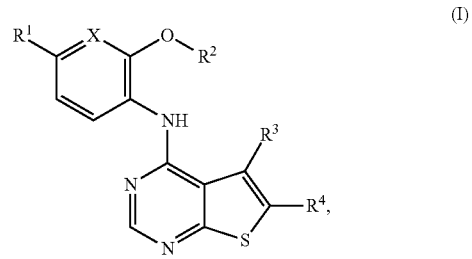

pharmaceutical compositions comprising these compounds and their therapeutic use for the prophylaxis and/or treatment of diseases which can be influenced by the inhibition of the kinase activity of Mnk1 and/or Mnk2 (Mnk2a or Mnk2b) and/or variants thereof.

11 Claims, No Drawings

(56) References Cited

FOREIGN PATENT DOCUMENTS

| | | |
|---|---|---|
| WO | 9413677 A1 | 6/1994 |
| WO | 9713771 A1 | 4/1997 |
| WO | 9924440 A1 | 5/1999 |
| WO | 0056738 A1 | 9/2000 |
| WO | 0075145 A1 | 12/2000 |
| WO | 02088138 A1 | 11/2002 |
| WO | 03037362 A2 | 5/2003 |
| WO | 2004037159 A2 | 5/2004 |
| WO | 2004106340 A2 | 12/2004 |
| WO | 2004113347 A1 | 12/2004 |
| WO | 2005010008 A1 | 2/2005 |
| WO | 2005042537 A1 | 5/2005 |
| WO | 2005080377 A1 | 9/2005 |
| WO | 2005117890 A2 | 12/2005 |
| WO | 2006014325 A2 | 2/2006 |
| WO | 2006066937 A2 | 6/2006 |
| WO | 2006094791 A1 | 9/2006 |
| WO | 2006124874 A2 | 11/2006 |
| WO | 2006136402 A1 | 12/2006 |
| WO | 2007056214 A2 | 5/2007 |
| WO | 2007056215 A2 | 5/2007 |
| WO | 2007059905 A2 | 5/2007 |
| WO | 2007081517 A2 | 7/2007 |
| WO | 2007084815 A2 | 7/2007 |
| WO | 2007115822 A1 | 10/2007 |
| WO | 2007147874 A1 | 12/2007 |
| WO | 2008006547 A2 | 1/2008 |
| WO | 2008041053 A2 | 4/2008 |
| WO | 2009065596 A2 | 5/2009 |
| WO | 2010023181 A1 | 3/2010 |
| WO | 2011104334 A1 | 9/2011 |
| WO | 2011104337 A1 | 9/2011 |
| WO | 2011104338 A1 | 9/2011 |
| WO | 2011104340 A1 | 9/2011 |

OTHER PUBLICATIONS

Banker, Gilbert S., et al; Modern Pharmaceutics (1996) 3rd Ed. Marcel Dekker, Inc. New York, p. 596.
Baumgartner, A., et al; Uber Thieno-Verbindungen: 14. Mitteilung: Darstellung 4-Aminosubstituierter Thieno[2.3-d]pyrimidyn-6-carbosa bsauurederivate; Institut fur Pharnazeutischer, 1993.
Cheng, C.C., et al; Potential Purine Antagonists. VI. Synthesis of 1-Alkyl- and 1-Aryl-4-substituted Pyrazolo[3,4-d] pyrimidines1,2; Journal of Organic Chemistry, American Chemical Society (1956) vol. 21 pp. 1240-1256.
Dörwald, Florencio Zaragoza, et al; Side Reactions in Organic Synthesis: A Guide to Successful Synthesys Design; (2005) Wiley; VCH, Weinheim p. IX of preface.
http://www.medterms.com/script/main/art.asp?articlekey=12063, last accessed on Aug. 24, 2010.
International Search Report for PCT/EP2006/005980 mailed Nov. 16, 2006.
International Search Report for PCT/EP2007/003186 mailed Jun. 8, 2007.
International Search Report for PCT/EP2007/006109 mailed Dec. 20, 2007.
International Search Report for PCT/EP2009/060876 mailed Nov. 10, 2009.
International Search Report for PCT/EP2011/052810 mailed May 16, 2011.
International Search Report for PCT/EP2011/052811/mailed May 18, 2011.
International Search Report for PCT/EP2011/052813 mailed May 30, 2011.
International Search Reportfor PCT/EP2008/009880 mailed Jun. 25, 2009.
Jorgensen, Anker, et al; Phosphorus Pentoxide in Organic Synthesis. XX [1]. Synthesis of N-Aryl-7H-pyrrolo [2 ,3-d]pyrimidin-4-amines; Journal of Heterocyclic Chemistry (1985) pp. 859-863.
Mogensen, Jorgen, et al; Phosphorus Pentoxide in Organic Synthesis: XXXIV*. Synthesis of 3-Arylthieno[2,3-d] pyrimidin-4(3H)-imines and their Rearrangement to N-arylthieno[2,3-d]pyrimidin-4-amines; Chemica Scripta (1988) vol. 28 pp. 195-200.
Munchhof, Michael J., et al; Design and SAR of Thienopyrimidine and Thienopyridine Inhibitors of VEGFR-2 Kinase Activity; Bioorganic & Medicinal Chemistry Letters (2004) vol. 14 pp. 21-24.
Peat, Andrew, J., et al; Novel Pyrazolopyrimidine Derivates as GSK-3 Inhibitors; Bioorganic & Medicinal Chemistry Letters (2004) vol. 14 pp. 2121-2125.
Showalter, H. D. Hollis, et al; Tyrosine Kinase Inhibitors. 16. 6,5,6-Tricyclic Benzothieno[3-,2-d]pyrimidines and Pyrimido[5,4-b]- and -[4,5-b]indoles as Potent Inhibitors of the Epidermal Growth Factor Receptor Tyrosine Kinase; Journal of Medicinal Chemistry (1999) vol. 42 pp. 5464-5474.
Sobolov, Susan B., et al; Selective N-Alkylation of Pyrrolopyrimidines and Indoles by "Transfer of Activation"; Tetrahedron Letters (1998) vol. 39 pp. 5685-5688.
Traxler, Peter, et al; Use of a Pharmacophore Model for the Design of EGF-R Tyrosine Kinase Inhibitors: 4-(Phenylamino)pyrazolo[3,4-d]pyrimidines; Journal of Medicinal Chemistry (1997) vol. 40, No. 22 pp. 3601-3616.
Traxler, Peter, M., et at; 4-(Phenylamino)pyrrolopyrimidines: Potent and Selective, ATP Site Directed Inhibitors of the EGF-Receptor Protein Tyrosine Kinase; Journal of Medicinal Chemistry (1996) vol. 39 pp. 2285-2292.
West, R. A., et al; 2-Alkyl(aryl)-and2,7-Dimethyl-4-substituted Aminopyrrolo [2,3-d]pyrimidines; Journal of Organic Chemistry (1961) vol. 26 pp. 3809-3812.
Wolff, Manfred, E.; Principles and Practice; Burger's Medicinal Chemistry and Drug Discovery (1995) 5ed, vol. 1 pp. 975-977.
Young, Rodney, C., et al; Purine Derivates as Competitive Inhibitors of Human Erythrocyte Membrane Phosphatidylinositol 4-Kinase; Journal of Medicinal Chemistry (1990) vol. 33 pp. 2073-2080.

* cited by examiner

SEQUENCE LISTING

<160> NUMBER OF SEQ ID NOS: 7

<210> SEQ ID NO 1
<211> LENGTH: 29
<212> TYPE: DNA
<213> ORGANISM: Homo sapiens

<400> SEQUENCE: 1
tttaggatcc gtatcttctc aaaagttgg          29

<210> SEQ ID NO 2
<211> LENGTH: 28
<212> TYPE: DNA
<213> ORGANISM: Homo sapiens

<400> SEQUENCE: 2
ctgggtcgac tcagagtgct gtgggcgg           28

<210> SEQ ID NO 3
<211> LENGTH: 28
<212> TYPE: DNA
<213> ORGANISM: Homo sapiens

<400> SEQUENCE: 3
acagggatcc gtgcagaaga aaccagcc           28

```
<210> SEQ ID NO 4
<211> LENGTH: 29
<212> TYPE: DNA
<213> ORGANISM: Homo sapiens

<400> SEQUENCE: 4
gatggtcgac tcaggcgtgg tctcccacc                                          29

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ala Thr Lys Ser Gly Ser Thr Thr Lys Asn Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphorylated-Ser

<400> SEQUENCE: 6

Thr Ala Thr Lys Ser Gly Ser Thr Thr Lys Asn Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phosphorylated-Ser
<220> FEATURE:
<223> OTHER INFORMATION: C-term CONH2

<400> SEQUENCE: 7

Cys Thr Ala Thr Lys Ser Gly Ser Thr Thr Lys Asn Arg
1               5                   10
```

THIENOPYRIMIDINES CONTAINING A SUBSTITUTED ALKYL GROUP FOR PHARMACEUTICAL COMPOSITIONS

SEQUENCE LISTING

The instant application contains a Sequence Listing which has been submitted in ASCII format via EFS-Web and is hereby incorporated by reference in its entirety. Said ASCII copy, created on Apr. 29, 2011, is named 012600.txt and is 2,135 bytes in size.

The present invention relates to thienopyrimidine compounds and to novel pharmaceutical compositions comprising thienopyrimidine compounds.

Moreover, the present invention relates to the use of the thienopyrimidine compounds of the invention for the production of pharmaceutical compositions for the prophylaxis and/or treatment of diseases which can be influenced by the inhibition of the kinase activity of Mnkl (Mnk1a or MnK1b) and/or Mnk2 (Mnk2a or Mnk2b) or further variants thereof. Particularly, the present invention relates to the use of the thienopyrimidine compounds of the invention for the production of pharmaceutical compositions for the prophylaxis and/or therapy of metabolic diseases, such as diabetes, hyperlipidemia and obesity, hematopoietic disorders, neurodegenerative diseases, kidney damage, inflammatory disorders, and cancer and their consecutive complications and disorders associated therewith.

Metabolic diseases are diseases caused by an abnormal metabolic process and may either be congenital due to an inherited enzyme abnormality or acquired due to a disease of an endocrine organ or failure of a metabolically important organ such as the liver or the pancreas.

The present invention is more particularly directed to the treatment and/or prophylaxis of in particular metabolic diseases of the lipid and carbohydrate metabolism and the consecutive complications and disorders associated therewith.

Lipid disorders cover a group of conditions which cause abnormalities in the level and metabolism of plasma lipids and lipoproteins. Thus, hyperlipidemias are of particular clinical relevance since they constitute an important risk factor for the development of atherosclerosis and subsequent vascular diseases such as coronary heart disease.

Diabetes mellitus is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Diabetes is a very disabling disease, because today's common anti-diabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

In one embodiment of the present invention the compounds and compositions of the present invention are useful for the treatment and/or prophylaxis of metabolic diseases of the carbohydrate metabolism and their consecutive complications and disorders such as impaired glucose tolerance, diabetes (preferably diabetes type II), diabetic complications such as diabetic gangrene, diabetic arthropathy, diabetic osteopenia, diabetic glomerosclerosis, diabetic nephropathy, diabetic dermopathy, diabetic neuropathy, diabetic cataract and diabetic retinopathy, diabetic maculopathy, diabetic feet syndrome, diabetic coma with or without ketoacidosis, diabetic hyperosmolar coma, hypoglycemic coma, hyperglycemic coma, diabetic acidosis, diabetic ketoacidosis, intracapillary glomerulonephrosis, Kimmelstiel-Wilson syndrome, diabetic amyotrophy, diabetic autonomic neuropathy, diabetic mononeuropathy, diabetic polyneuropathy, diabetic angiopathies, diabetic peripheral angiopathy, diabetic ulcer, diabetic arthropathy, or obesity in diabetes.

In a further embodiment the compounds and compositions of the present invention are useful for the treatment and/or prophylaxis of metabolic diseases of the lipid metabolism (i.e. lipid disorders) and their consecutive complications and disorders such as hypercholesterolemia, familial hypercholesterolemia, Fredrickson's hyperlipoproteinemia, hyperbetalipoproteinemia, hyperlipidemia, low-density-lipoprotein-type [LDL] hyperlipoproteinemia, pure hyperglyceridemia, endogenous hyperglyceridemia, isolated hypercholesterolemia, isolated hypertroglyceridemia, cardiovascular diseases such as hypertension, ischemia, varicose veins, retinal vein occlusion, atherosclerosis, angina pectoris, myocardial infarction, stenocardia, pulmonary hypertension, congestive heart failure, glomerulopaty, tubulointestitial disorders, renal failure, angiostenosis, or cerebrovascular disorders, such as cerebral apoplexy.

In a further embodiment of the present invention the compounds and compositions of the present invention are useful for the treatment and/or prophylaxis of hematopoetic disorders and their consecutive complications and disorders such as acute myeloid leukemia (AML), Morbus Hodgkin, Non-Hodgkin's lymphoma; hematopoetic disease, acute non-lymphocytic leukemia (ANLL), myeloproliferative disease acute promyelocytic leukemia (APL), acute myelomonocytic leukemia (AMMoL), multiple myeloma, polycythemia vera, lymphoma, acute lymphocytic leukemia (ALL), chronic lymphocytic leukemia (CCL), Wilm's tumor, or Ewing's Sarcoma.

In a further embodiment of the present invention the compounds and compositions of the present invention are useful for the treatment and/or prophylaxis of cancer and consecutive complications and disorders such as cancer of the upper gastrointestinal tract, pancreatic carcinoma, breast cancer, colon cancer, ovarian carcinoma, cervix carcinoma, endometrial cancer, brain tumor, testicular cancer, laryngeal carcinoma, osteocarcinoma, prostatic cancer, retinoblastoma, liver carcinoma, lung cancer, neuroblastoma, renal carcinoma, thyroid carcinoma, esophageal cancer, soft tissue sarcoma, skin cancer, osteosarcoma, rhabdomyosarcoma, bladder cancer, metastatic cancer, cachexia, or pain.

Certain anti-cancer drugs such as cisplatin are linked to serious side effects such as nephrotoxicity or ototoxicity, which can be dose limiting. Activation of Mnks has been linked to these side effects. In a further embodiment of the present invention, the compounds and compositions of the present invention are useful for the treatment and/or prophylaxis of ear or kidney damage, in particular for the prevention or treatment of ear and kidney drug induced damage Furthermore, the present invention relates to the use of thienopyrimidine compounds for the production of pharmaceutical compositions for the prophylaxis and/or therapy of cytokine related diseases.

Such diseases are i.a. inflammatory diseases, autoimmune diseases, destructive bone disorders, proliferative disorders, infectious diseases, neurodegenerative diseases, allergies, or other conditions associated with proinflammatory cytokines.

Allergic and inflammatory diseases such as acute or chronic inflammation, chronic inflammatory arthritis, rheumatoid arthritis, psoriasis, COPD, inflammatory bowel disease, asthma and septic shock and their consecutive complications and disorders associated therewith.

Inflammatory diseases like rheumatoid arthritis, inflammatory lung diseases like COPD, inflammatory bowel disease and psoriasis afflict one in three people in the course of their lives. Not only do those diseases impose immense health care costs, but also they are often crippling and debilitating.

Although inflammation is the unifying pathogenic process of these inflammatory diseases below, the current treatment approach is complex and is generally specific for any one disease. Many of the current therapies available today only treat the symptoms of the disease and not the underlying cause of inflammation.

The compositions of the present invention are useful for the treatment and/or prophylaxis of inflammatory diseases and consecutive complications and disorders. such as chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitrel valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Moreover, cytokines are also believed to be implicated in the production and development of various cardiovascular and cerebrovascular disorders such as congestive heart disease, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoporosis and periodontitis, and the abnormal changes in bone metabolism which may accompany rheumatoid arthritis and osteoarthritis.

Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke.

Excessive cytokine production has, moreover, been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis. The treatment and/or prophylaxis of these diseases are also contemplated by the present invention Additionally, the inventive compositions may be used to treat inflammation associated with autoimmune diseases including, but not limited to, systemic lupus erythematosis, Addison's disease, autoimmune polyglandular disease (also known as autoimmune polyglandular syndrome), glomerulonephritis, rheumatoid arthritis scleroderma, chronic thyroiditis, Graves' disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, and graft vs. host disease.

In a further embodiment the compositions of the present invention may be used for the treatment and prevention of infectious diseases such as sepsis, septic shock, Shigellosis, and *Helicobacter pylori* and viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS or malignancy, malaria, mycobacterial infection and meningitis. These also include viral infections, by influenza virus, varicella-zoster virus (VZV), Epstein-Barr virus, human herpesvirus-6 (HHV-6), human herpesvirus-7 (HHV-7), human herpesvirus-8 (HHV-8), Poxvirus, Vacciniavirus, Monkeypoxvirus, pseudorabies and rhinotracheitis.

The compositions of the present invention may also be used topically in the treatment or prophylaxis of topical disease states mediated by or exacerbated by excessive cytokine production, such as inflamed joints, eczema, psoriasis and other inflammatory skin conditions such as sunburn; inflammatory eye conditions including conjunctivitis; pyresis, pain and other conditions associated with inflammation.

Periodontal disease has also been implemented in cytokine production, both topically and systemically. Hence, use of compositions of the present invention to control the inflammation associated with cytokine production in such peroral diseases such as gingivitis and periodontitis is another aspect of the present invention.

Finally, the compositions of the present invention may also be used to treat or prevent neurodegenerative disease selected from Alzheimer's disease, Parkinson's disease, amyotrophic lateral sclerosis, Huntington's disease, frontotemporal lobar dementia, spinocerebellar ataxia, dementia with Lewy bodies, cerebral ischemia or neurodegenerative disease caused by traumatic injury, glutamate neurotoxicity or hypoxia.

In a preferred embodiment the compositions of the present invention may be used to treat or prevent a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Protein kinases are important enzymes involved in the regulation of many cellular functions. The LK6-serine/threonine-kinase gene of Drosophila melanogaster was described as a short-lived kinase which can associate with microtubules (J. Cell Sci. 1997, 110(2): 209-219). Genetic analysis in the development of the compound eye of Drosophila suggested a role in the modulation of the RAS signal pathway (Genetics 2000 156(3): 1219-1230). The closest human homologues of Drosophila LK6-kinase are the MAP-kinase interacting kinase 2 (Mnk2, e.g. the variants Mnk2a and Mnk2b) and MAP-kinase interacting kinase 1 (Mnk1) and variants thereof. These kinases are mostly localized in the cytoplasm. Mnks are phosphorylated by the p42 MAP kinases Erk1 and Erk2 and the p38-MAP kinases. This phosphorylation is triggered in a response to growth factors, phorbol esters and oncogenes such as Ras and Mos, and by stress signaling molecules and cytokines. The phosphorylation of Mnk proteins stimulates their kinase activity towards eukaryotic initiation factor 4E (eIF4E) (EMBO J. 16: 1909-1920, 1997; Mol Cell Biol 19, 1871-1880, 1990; Mol Cell Biol 21, 743-754, 2001). Simultaneous disruption of both, the Mnk1 and Mnk2 gene in mice diminishes basal and stimulated eIF4E phosphorylation (Mol Cell Biol 24, 6539-6549, 2004). Phosphorylation of eIF4E results in a regulation of the protein translation (Mol Cell Biol 22: 5500-5511, 2001).

There are different hypotheses describing the mode of the stimulation of the protein translation by Mnk proteins. Most publications describe a positive stimulatory effect on the cap-dependent protein translation upon activation of MAP kinase-interacting kinases. Thus, the activation of Mnk proteins can lead to an indirect stimulation or regulation of the protein translation, e.g. by the effect on the cytosolic phospholipase 2 alpha (BBA 1488:124-138, 2000).

WO 03/037362 discloses a link between human Mnk genes, particularly the variants of the human Mnk2 genes, and diseases which are associated with the regulation of body weight or thermogenesis. It is postulated that human Mnk genes, particularly the Mnk2 variants are involved in diseases such as e.g. metabolic diseases including obesity, eating disorders, cachexia, diabetes mellitus, hypertension, coronary heart disease, hypercholesterolemia, dyslipidemia, osteoarthritis, biliary stones, cancer of the genitals and sleep apnea, and in diseases connected with the ROS defense, such as e.g. diabetes mellitus and cancer. WO 03/03762 moreover discloses the use of nucleic acid sequences of the MAP kinase-interacting kinase (Mnk) gene family and amino acid sequences encoding these and the use of these sequences or of effectors of Mnk nucleic acids or polypeptides, particularly Mnk inhibitors and activators in the diagnosis, prophylaxis or therapy of diseases associated with the regulation of body weight or thermogenesis.

WO 02/103361 describes the use of kinases 2a and 2b (Mnk2a and Mnk2b) interacting with the human MAP kinase in assays for the identification of pharmacologically active ingredients, particularly useful for the treatment of diabetes mellitus type 2. Moreover, WO 02/103361 discloses also the prophylaxis and/or therapy of diseases associated with insulin resistance, by modulation of the expression or the activity of Mnk2a or Mnk2b. Apart from peptides, peptidomimetics, amino acids, amino acid analogues, polynucleotides, polynucleotide analogues, nucleotides and nucleotide analogues, 4-hydroxybenzoic acid methyl ester are described as a substance which binds the human Mnk2 protein.

First evidence for a role of Mnks in inflammation was provided by studies demonstrating activation of Mnk1 by proinflammatory stimuli. The cytokines TNFα and IL-1β trigger the activation of Mnk1 in vitro (Fukunaga and Hunter, EMBO J. 16(8): 1921-1933, 1997) and induce the phosphorylation of the Mnk-specific substrate eIF4E in vivo (Ueda et al., Mol Cell Biol 24(15): 6539-6549, 2004). In addition, administration of lipopolysaccharide (LPS), a potent stimulant of the inflammatory response, induces activation of Mnk1 and Mnk2 in mice, concomitant with a phosphorylation of their substrate eIF4E (Ueda et al., Mol Cell Biol 24(15): 6539-6549, 2004).

Furthermore, Mnk1 has been shown to be involved in regulating the production of proinflammatory cytokines. Mnk1 enhances expression of the chemokine RANTES (Nikolcheva et al., J Clin Invest 110, 119-126, 2002). RANTES is a potent chemotractant of monocytes, eosinophils, basophiles and, natural killer cells. It activates and induces proliferation of T lymphocytes, mediates degranulation of basophils and induces the respiratory burst in eosinophils (Conti and DiGioacchino, Allergy Asthma Proc 22(3):133-7, 2001)

WO 2005/00385 and Buxade et al., Immunity 23: 177-189, August 2005 both disclose a link between Mnks and the control of TNFα biosynthesis. The proposed mechanism is mediated by a regulatory AU-rich element (ARE) in the TNFα mRNA. Buxade et al. demonstrate proteins binding and controlling ARE function to be phosphorylated by Mnk1 and Mnk2. Specifically Mnk-mediated phosphorylation of the ARE-binding protein hnRNP A1 has been suggested to enhance translation of the TNFα mRNA.

TNFα is not the only cytokine regulated by an ARE. Functional AREs are also found in the transcripts of several interleukins, interferones and chemokines (Khabar, J Interf Cytokine Res 25: 1-10, 2005). The Mnk-mediated phosphorylation of ARE-binding proteins has thus the potential to control biosynthesis of cytokines in addition to that of TNFα.

Current evidence demonstrates Mnks as down stream targets of inflammatory signalling as well as mediators of the inflammatory response. Their involvement in the production of TNFα, RANTES, and potentially additional cytokines suggests inhibition of Mnks as strategy for anti-inflammatory therapeutic intervention.

Mnk1 and Mnk2 (including all splice forms) phosphorylate the translation factor eIF4E on Serine 209. Mnk1/2 double knockout mice completely lack phosphorylation on Serine 209, indicating that Mnk kinase are the only kinases able to phosphorylate this site in vivo (Ueda et al., Mol Cell Biol. 2004; 24(15):6539-49). eIF4E is overexpressed in a wide range of human malignancies, and high eIF4E expression is frequently associated with more aggressive disease and poor prognosis. Furthermore, eIF4E can act as an oncogene when assayed in standard assays for oncogenic activity (e.g. Ruggero et al., Nat. Med. 2004 May; 10(5):484-6). eIF4E excerts its oncogenic activity by stimulating the translation of oncogenes such as c-myc and cyclinD1 (Culjkovic et al., J. Cell Biol. 2006; 175(3):415-26), by increasing the expression of pro-survival factors such as MCP-1 (Wendel et al., Genes Dev. 2007; 21(24):3232-7) and by positively regulating pathways of drug resistance (Wendel et al., Nature 2004; 428(6980):332-7; Graff et el., Cancer Res. 2008; 68(3): 631-4; De Benedetti and Graff, Oncogene 2004; 23(18):3189-99; Barnhart and Simon, J Clin Invest. 2007; 117(9):2385-8). Suppression of eIF4E expression by antisense oligonucleotides has shown promise in preclinical experiments with human tumor cells (Graff et al., J Clin Invest. 2007; 117(9):2638-48). It has been shown that phosphorylation on Ser209 is strictly required for the oncogenic activity of eIF4E in vitro and in vivo (Topisirovic et al., Cancer Res. 2004; 64(23):8639-42; Wendel et al., Genes Dev. 2007; 21(24):3232-7). Thus, inhibition of Mnk1 and Mnk2 is expected to have beneficial effects in human malignancies.

Inhibitors of Mnk (referred to as CGP57380 and CGP052088) have been described (cf. Mol. Cell. Biol. 21, 5500, 2001; Mol Cell Biol Res Comm 3, 205, 2000; Genomics 69, 63, 2000). CGP052088 is a staurosporine derivative having an $IC_{50}$ of 70 nM for inhibition of in vitro kinase activity of Mnk1. CGP57380 is a low molecular weight selective, non-cytotoxic inhibitor of Mnk2 (Mnk2a or Mnk2b) or of Mnk1: The addition of CGP57380 to cell culture cells, transfected with Mnk2 (Mnk2a or Mnk2b) or Mnk1 showed a strong reduction of phosphorylated eIF4E.

Further inhibitors of Mnk have been described. See for example Applicants patent applications WO 06/066937, describing pyrazolopyrimidine compounds, WO 06/136402 describing certain thienopyrimidine compounds, WO 07/115,822 describing further thienopyrimidine compounds with modified core ring, and WO 08/006,547 describing pyrrolopyrimidines as inhibitors of Mnk kinases.

The problem underlying the present invention is to provide potent and selective Mnk1 and/or Mnk2 inhibitors which may effectively and safely be used for the treatment of metabolic diseases, inflammatory diseases, cancer, neurodegenerative diseases and their consecutive complication and disorders.

It has now been surprisingly found that certain thienopyrimidine compounds are potent inhibitors of the kinase enzymes Mnk1 and/or Mnk2 and/or variants thereof and as such may be useful in the prophylaxis and/or therapy of diseases which can be influenced by the inhibition of the kinase activity of Mnk1 and/or Mnk2 (Mnk2a or Mnk2b) and/or variants thereof.

In contrast to the thienopyrimidine compounds known in the art, for example, the compoonds disclosed in the Applicants patent applications WO 06/136402 and WO 2007/115822, the thienopyrimidine compounds of the present invention provide several advantages, namely, enhanced solubility, the possibility to form stable salts, improved metabolic stability, improved pharmacokinetic properties, enhanced or retained activity in biochemical or cellular Mnk activity assays and enhanced or retained selectivity against other kinases.

The thienopyrimidine compounds disclosed in WO 06/136402 and WO 07/115,822 exhibit high activity in Mnk enzyme assays and extremely high selectivity, however they show a very low solubility and are in most cases metabolic unstable resulting in undesired pharmacokinetic properties.

It has been surprisingly found that by the introduction of a polar group at the $R^4$-position in the compounds of general formula (I) below leads to surprising substantial metabolic stabilization, rendering the thienopyrimidines of the present invention useful for in vivo pharmacological applications.

Moreover, compounds described in this application also show improved solubility, have strong inhibitory potency in biochemical and cellular assays and are highly selective, resulting in overall greatly improved pharmacological properties.

If not specified otherwise, any alkyl moiety mentioned in this application may be straight-chained or branched.

Thienopyrimidine compounds of the present invention are compounds of the general formula (I):

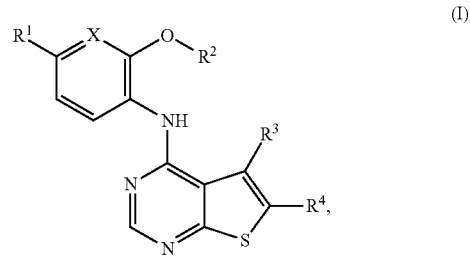

wherein
X is CH or N,
$R^1$ is a hydrogen or halogen atom or CN or an $C_{1-3}$ alkyl or CONH$_2$ group,
$R^2$ is a straight-chained or branched $C_{1-6}$ alkyl group which is independently substituted with one or two fluorine atoms, or one or two trifluoromethyl, tetrahydropyranyl, cyclopropyl, H$_2$N—CO—, R$^5$NHCO— or (R$^5$)$_2$N—CO— groups,
   wherein the above-mentioned cyclopropyl group may be substituted with one or two F or —CH$_2$—CN,
   and wherein the two R$^5$ groups together with the N atom to which they are attached may form a 4- to 8-membered ring, in which a carbon atom may be replaced by a O, S, SO, SO$_2$ and/or which may be substituted with OH, NH$_2$, N(C$_{1-3}$-alkyl)$_2$, NH(C$_{1-3}$ alkyl), CF$_3$ or C$_{1-3}$-alkyl, or a straight-chained or branched C$_{2-6}$ alkyl group which is independently substituted in position 2 to 6 with one or two hydroxy, C$_{1-3}$ alkoxy, amino, CN, R$^5$NH—, (R$^5$)$_2$N—, R$^5$OCONH—, R$^5$CONH—, R$^5$SO$_2$NH—, R$^5$NHCONH— groups,
   wherein R$^5$ is a C$_{1-5}$ alkyl group, preferably a O$_{1-4}$ alkyl group, more preferably Me, i-Pr or t-Bu, each optionally substituted with one CF$_3$, NH$_2$, NH(C$_{1-3}$ alkyl), N(C$_{1-3}$-alkyl)$_2$ or MeO— group, and wherein the hydrogen atoms of any of the above-mentioned NH moiety may be replaced by methyl,
$R^3$ is a $C_{1-2}$ alkyl group and
$R^4$ is a carboxy, $C_{1-3}$ alkoxy-carbonyl, —$CONH_2$, —$CONHR^7$, —CONH—$OR^7$, —CONH—$SO_2R^7$ or —CO—NH-L-$R^6$ group,
wherein L is a —$(CH_2)_n$—, —$CH_2$—C≡C—$CH_2$—, or

, $R^6$ is OH, —$NH_2$, —$NHR^7$, —$N(R^7)_2$, —NH—$CO_2R^7$ or a 3- to 6-membered cyclic amine such as pyrrolidine or piperidine,
n is 2 or 3 and
$R^7$ is $C_{1-4}$ alkyl, preferably methyl,
or a tautomer, enantiomer or salt thereof.
Preferred compounds of formula (I) are those, wherein
X, $R^1$, $R^2$ and $R^4$ are as defined above and
$R^3$ is methyl,
or a tautomer or salt thereof.
A preferred subgroup concerns those compound of formula (I), wherein
$R^2$ to $R^4$ are as defined as above,
X is CH and
$R^1$ is a fluorine atom,
or a tautomer or salt thereof.
Another preferred subgroup concerns those compounds of formula (I), wherein
$R^2$ to $R^4$ are as defined above,
X is N and
$R^1$ is a hydrogen atom,
or a tautomer or salt thereof.
A third preferred subgroup concerns those compounds of formula (I), wherein
X, $R^1$, $R^3$ and $R^4$ are as defined above and
$R^2$ is selected from:
(dimethylamino)-carbonylmethyl,
ethyl, 2-amino-ethyl, 1-(trifluoromethyl)-ethyl;
isopropyl optionally substituted in position 2 with ethoxycarbonyl, amino or tert-butyloxycarbonylamino;
2,2"-diamino-isopropyl, 2,2"-difluoro-isopropyl, 2,2"-di-(ethoxy)-isopropyl, 2,2"-bis-(tert-butyloxycarbonylamino)-isopropyl, 2-[2'-(trifluoromethyl)-ethylamino]-isopropyl, 3-amino-1-methyl-propyl, 3-(dimethylamino)-1-methyl-propyl, 3-hydroxy-1,3-dimethyl-butyl, or
a fluor-containing residue such as 1,3-difluoropropan-2-yl, 1,1,1-trifluoropropan-2-yl or 1,1-difluoroethyl-,
or a tautomer or salt thereof,
particularly those compounds of formula (I), wherein
X, $R^1$, $R^3$ and $R^4$ are as defined above and
$R^2$ is selected from:
isopropyl and isobutyl optionally substituted in position 2 or 3 with ethoxycarbonyl, amino, tert-butyloxycarbonylamino or methylsulfonylamino or a tautomer or salt thereof.
A fourth preferred subgroup concerns those compounds of formula (I), wherein
X, $R^1$ to $R^3$ are as defined above and
$R^4$ is selected from:
carboxy, $C_{1-3}$ alkoxy-carbonyl, aminocarbonyl, N—($C_{1-3}$ alkyl)-aminocarbonyl or N,N-[di-($C_{1-3}$ alkyl)]-aminocarbonyl group,
wherein the alkyl moiety of the above-mentioned N—($C_{1-3}$ alkyl)-aminocarbonyl and N,N-[di-($C_{1-3}$ alkyl)]-aminocarbonyl groups may optionally be terminally substituted with a hydroxy, amino, N—($C_{1-3}$ alkyl)-amino or N,N-[di-($C_{1-3}$ alkyl)]-amino group,
or a tautomer or salt thereof,
particularly those compounds of formula (I), wherein
X, $R^1$ to $R^3$ are as defined above and
$R^4$ is selected from:
aminocarbonyl, N-methyl-aminocarbonyl;
N-ethyl-aminocarbonyl terminally substituted in the ethyl moiety with hydroxy or N,N-dimethylamino;
N-(n-propyl)-aminocarbonyl terminally substituted in the n-propyl moiety with N,N-dimethylamino;
Carboxy or methoxycarbonyl,
or a tautomer or salt thereof.
Particularly preferred Compounds of formula (I) are:
a) Methyl 4-(2-(1-aminopropan-2-yloxy)-4-fluorophenylamino)-5-methyl-thieno[2,3-d]pyrimidine-6-carboxylate,
b) 4-(2-(1-Aminopropan-2-yloxy)-4-fluorophenylamino)-N-5-methylthieno[2,3-d]pyrimidine-6-carboxamide,
c) Methyl 4-(4-fluoro-(2-(1-methylsulfonamido)propan-2-yloxy)phenylamino)-5-methyl-thieno[2,3-d]pyrimidine-6-carboxylate,
d) 4-(2-(1-Aminopropan-2-yloxy)-4-fluorophenylamino)-5-methylthieno[2,3-d]pyrimidine-6-carboxamide,
e) 4-(2-(1-Aminopropan-2yloxy)-4-fluorophenylamino)-5-methyl-Ithieno[2,3-d]pyrimidine-6-carboxylic acid,
f) Methyl 4-(2-(4-aminobutan-2yloxy)-4-fluorophenylamino)-5-methyl-thieno[2,3-d]pyrimidine-6-carboxylate,
g) Methyl 4-(4-fluoro-2-(4-(methylsulfonamido)butan-2yloxy)phenylamino)-5-methyl-thieno[2,3-d]pyrimidine-6-carboxylate,
h) 4-(2-(4-Aminobutan-2yloxy)pyridin-3-ylamino)-5-methylthieno[2,3-d]pyrimidine-6-carboxylic acid,
i) N-(3-(Dimethylamino)propyl)-4-(4-fluoro-2-(4-hydroxy-4-methylpentan-2-yloxy)phenylamino)-5-methylthieno[2,3-d]pyrimidine-6-carboxamide,
j) 5-Methyl-4-(2-(1,1,1-trifluoropropan-2yloxy)pyridin-3-ylamino)thieno[2,3-d]pyrimidine-6-carboxylic acid,
k) 5-Methyl-4-(2-(1,1,1-trifluoropropan-2yloxy)pyridin-3-ylamino)thieno[2,3-d]pyrimidine-6-carboxamide,
l) N-Methyl-5-methyl-4-(2-(1,1,1-trifluoropropan-2yloxy)pyridin-3-ylamino)thieno[2,3-d]pyrimidine-6-N-methyl-carboxamide,
m) 4-(2-(1,3-Difluoropropan-2yloxy)-4-fluorophenylamino)-5-methyl-thieno[2,3-d]pyrimidine-6-carboxamide,
n) N-Methyl-4-(2-(1,3-difluoropropan-2-yloxy)-4-fluorophenylamino)-5-methyl-thieno[2,3d]pyrimidine-6-carboxamide,
o) 4-(2-(1,3-Difluoropropan-2yloxy)-4-fluorophenylamino)-N-(3-(dimethylamino)propyl)-5-methyl-thieno[2,3-d]-pyrimidine-6-carboxamide,
p) 4-(2-(1,3-Difluoropropan-2yloxy)-4-fluorophenylamino)-N-(2-(dimethylamino)ethyl)-5-methylthieno[2,3-d]pyrimidine-6-carboxamide,
q) 4-(2-(1,3-Difluoropropan-2yloxy)-4-fluorophenylamino)-N-(2-(hydroxyethyl)-5-methylthieno[2,3-d]pyrimidine-6-carboxamide,
r) 4-(2-(1,3-Difluoropropan-2yloxy)-4-fluorophenylamino)-5-methyl-N-(3-(pyrrolidin-1-yl)propyl)thieno[2,3-d]pyrimidine-6-carboxamide,
s) N-((trans)-2-Aminocyclopropyl)-4-(2-(1,3-difluoropropan-2-yloxy)-4-fluorophenylamino)-5-methylthieno[2,3-d]pyrimidine-6-carboxamide, t) 4-(2-(2-Fluoropropoxy)pyridin-3-ylamino)-N-(2-hydroxyethyl)-5-methylthieno[2,3-d]pyrimidine-6-carboxamide, u) 4-(2-(2,2-Difluoroethoxy)pyridin-3-ylamino)-5-methylthieno[2,3-d]pyrimidine-6-carboxylic acid, v) 4-(2-(2,2-Difluoroethoxy)pyridin-3-ylamino)-5-methylthieno[2,3-d]pyrimidine-6-carboxamide, w) 4-(2-(2,2-Difluoroethoxy)pyridin-3-ylamino)-N-(3-(dimethylamino)propyl)-5-methylthieno[2,3-d]pyrimidine-6-carboxamide, x) 4-(2-(1-(Ethylamino)-1-oxopropan-2-yloxy)-4-fluorophenylamino)-N,5-dimethylthieno[2,3-d]pyrimidine-6-carboxamide and y) 4-(2-(1-(Ethylamino)-1-oxopropan-2-yloxy)-4-fluorophenylamino)-N,5-dimethylthieno[2,3-d]pyrimidine-6-carboxamide, or a pharmaceutically acceptable salt thereof.

Typical methods of preparing the compounds of the invention are described below in the experimental section.

The potent inhibitory effect of the compounds of the invention may be determined by in vitro enzyme assays as described in the Examples in more detail.

The compounds of the present invention can be synthesized according to the following synthesis schemes:

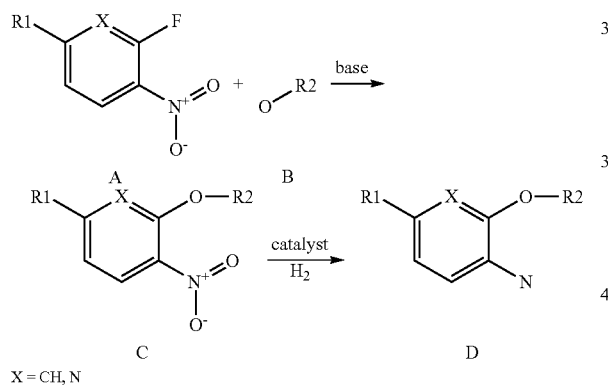

X = CH, N

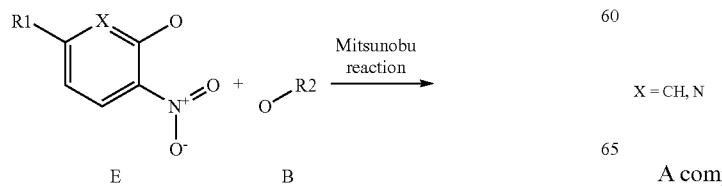

Compounds of the general formula C can be synthesized by reaction of a compound A with the deprotonated alcohol B in appropriate solvents such as THF or DMF at a temperature between 0° C. and 150° C. The deprotonated form of B can be obtained by deprotonation with a base such as sodium hydride or lithium hexamethyldisilazane at a preferred temperature of 0° C. Hydrogenation of compound C in order to obtain a compound of the general formula D can be achieved by reacting C in the presence of hydrogen and a catalyst such as palladium or Raney nickel. The hydrogen can be introduced as a gas or stem from a hydrogen source such as ammonium formate.

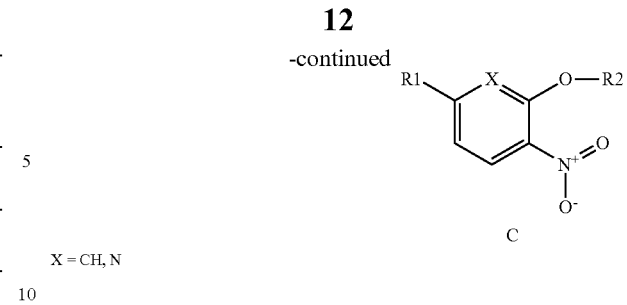

X = CH, N

Compounds of the general formula C can be also obtained by Mitsunobu reaction of a compound with the general formula E with an alcohol B in the presence of triphenylphosphine and an dialkylazodicarboxylate such as diethylazodicarboxylate, diisopropylazodicarboxylate or di-tert.butylazodiacarboxylate in a solvent such as THF at temperatures between −10° C. and 80° C., preferrably between 0° C. and 30° C.

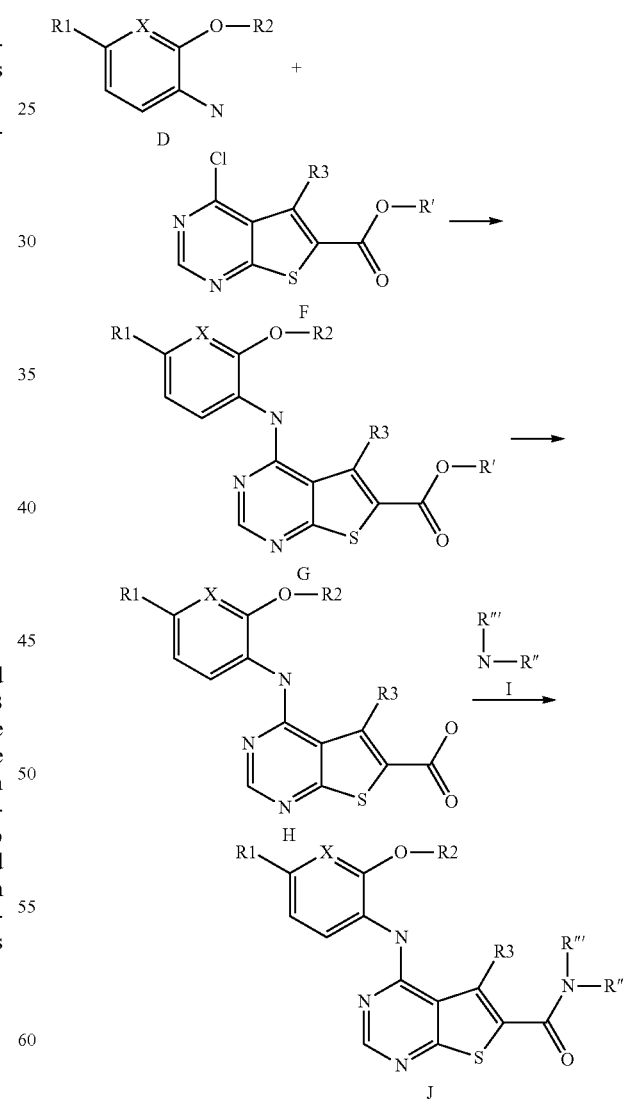

X = CH, N

A compound of the formula G can be synthesized by reaction of compound D with F preferably in the presence of an acid such as p-toluene sulfonic acid or hydrochloric acid in solvents such as dioxan at temperatures between 10° C. and 150° C. Synthesis of a compound with the general formula H can be achieved by reaction of compound G with a base such as sodium hydroxide or lithium hydroxide in solvents such as methanol, ethanol, THF and water or mixtures thereof, preferably in ethanol/THF or THF/water at temperatures between 10° C. and 100° C. A compound of the general formula J can be obtained by reaction of compound H with amines of the general formula I using amide coupling procedures employing reagents such as TBTU, HATU or EDC/N-Hydroxysuccinimide in the presence or absence of bases such as diisopropylethylamine in solvents such as DMF or THF at temperatures between 0° C. and 120° C. preferably between 0° C. and 30° C.

Pharmaceutically acceptable salts of the compounds of the invention of formula (I) can be formed with numerous organic and inorganic acids and bases. Exemplary acid addition salts including acetate, adipate, alginate, ascorbate, aspartate, benzoate, benzenesulfonate, bisulfate, borate, butyrate, citrate, camphorate, camphersulfonate, cyclopentanepropionate, digluconate, dodecyl sulfate, ethane sulfonate, fumarate, glucoheptanoate, glycerophosphate, hemisulfate, heptanoate, hexanoate, hydrochloride, hydrobromide, hydroiodide, 2-hydroxyethane sulfonate, lactate, maleate, methane sulfonate, 2-naphthalene sulfonate, nicotinate, nitrate, oxalate, pamoate, pectinate, persulfate, 3-phenyl sulfonate, 3-phenylpropionate, phosphate, picrate, pivalate, propionate, salicylate, succinate, sulfate, sulfonate, tartrate, thiocyanate, toluene sulfonate such as tosylate, undecanoate, or the like.

Basic nitrogen-containing moieties can be quaternized with such agents as lower alkyl halides, such as methyl, ethyl, propyl, and butyl chloride, bromide and iodide; dialkyl sulfates like dimethyl, diethyl, dibutyl, and diamyl sulfates, long-chain alkyl halides such as decyl, lauryl, myristyl and stearyl chloride, bromide and iodide, or aralkyl halides like benzyl and phenethyl bromides, or others. Water soluble or dispersible products are thereby obtained.

Pharmaceutically acceptable basic addition salts include but are not limited to cations based on the alkaline and alkaline earth metals such as sodium, lithium, potassium, calcium, magnesium, aluminum salts and the like, as well as non toxic ammonium quarternary ammonium, and amine cations, including but not limited to ammonium, tetramethylammonium, tetraethylammonium, methylamine, dimethylamine, trimethylamine, triethylamine, ethylamine and the like. Other representative amines useful for the formation of base addition salts include benzazethine, dicyclohexyl amine, hydrabine, N-methyl-D-glucamine, N-methyl-D-glucamide, t-butyl amine, diethylamine, ethylendiamine, ethanolamine, diethanolamine, piperazine and the like and salts with amino acids such as arginine, lysine, or the like.

Unless specifically indicated, throughout the specification and the appended claims, a given chemical formula or name shall encompass tautomers and all stereo, optical and geometrical isomers (e.g. enantiomers, diastereomers, E/Z isomers etc. ...) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

As used herein the term "metabolite" refers to (i) a product of metabolism, including intermediate and products, (ii) any substance involved in metabolism (either as a product of metabolism or as necessary for metabolism), or (iii) any substance produced or used during metabolism. In particular it refers to the end product that remains after metabolism.

As used herein the term "prodrug" refers to (i) an inactive form of a drug that exerts its effects after metabolic processes within the body convert it to a usable or active form, or (ii) a substance that gives rise to a pharmacologically active metabolite, although not itself active (i.e. an inactive precursor).

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309-396; *Burger's Medicinal Chemistry and Drug Discovery*, 5th Ed., M. Wolff (ed.), John Wiley & Sons, 1995, particularly Vol. 1 and pp. 172-178 and pp. 949-982; *Pro-Drugs as Novel Delivery Systems*, T. Higuchi and V. Stella (eds.), Am. Chem. Soc., 1975; *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

As used herein the term "$C_{3-10}$ cycloalkyl" or "$C_{3-8}$ cycloalkyl" refers to mono- or polycyclic carbocyclic alkyl substituent or group having 3 to 10 or 3 to 8 ring atoms respectively, such as cyclopropyl, cyclobutyl, cyclopentyl, cyclohexyl, cycloheptyl, cyclobutenyl, cyclopentenyl, cyclopentadienyl, cyclohexenyl, cyclohexadienyl, cycloheptenyl, cycloheptadienyl, cycloheptatrienyl perhydrated naphthalene or indene, adamantyl or norbonanyl and the like.

The term "$C_{1-8}$ alkyl" as used herein alone or in combination with other terms such as in alkoxy refers to a $O_{1-8}$, preferably $C_{1-4}$ straight or branched alkyl/alkoxy group such as methyl, ethyl, propyl (iso-, n-), butyl (iso-, n-, sec-, tert-), pentyl, hexyl, methoxy, ethoxy, propoxy (iso-, n-), butoxy (iso-, n-, sec-, tert-), pentoxy, hexoxy; moreover, the term "$C_{1-8}$ alkyl" also includes an alkyl group which may contain oxygen in the chain and may be substituted with halogen to form an ether or halogenated ether group.

Any hydrogen atom, particularly in an alkyl, alkoxy or alkenyl group may be replaced by a fluorine atom.

The term "$C_{2-8}$ alkenyl" by itself or as part of another group refers to a straight or branched alkenyl group of 2 to 8 carbons, preferably 2 to 6 carbons, in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl.

The term "heterocyclyl" refers to monocyclic saturated or unsaturated heterocyclyl groups with 1 to 4 hetero atoms selected from N, S and O, with the remainder of the ring atoms being carbon atoms and having preferably a total number of ring atoms of 3 to 10, such as morpholino, piperazinyl, piperidinyl, pyridyl, pyrimidinyl, thiazolyl, indolyl, imidazolyl, oxadiazolyl, tetrazolyl, pyrazinyl, triazolyl, thiophenyl or furanyl.

The term "heteroaryl" refers to a mono- or bicyclic aromatic group with 1 to 4 hetero atoms selected from N, S and O, with the remainder of the ring atoms being carbon atoms and having preferably a total number of ring atoms of 5 to 10. Examples without limitation of heteroaryl groups are such as benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, quinolinyl, isoquinolinyl, purinyl, carbazolyl, benzoxazolyl, benzamidazolyl, indolyl, isoindolyl, pyrazinyl, diazinyl, pyrazine, triazinyltriazine, tetrazinyl, tetrazolyl, benzothiophenyl, benzopyridyl and benzimidazolyl.

In a further aspect the present invention provides pharmaceutical compositions comprising a thienopyrimidine compound of the present invention and optionally a pharmaceutically acceptable carrier.

The pharmaceutical composition according to the present invention may further comprise an additional therapeutic agent. Particularly preferred are compositions, wherein the additional therapeutic agent is selected from antidiabetics like insulin, long and short acting insulin analogues, sulfonylureas, biguanides, DPP-IV inhibitors, SGLT2 inhibitors, 11β-HSD inhibitors, glucokinase activators, AMPK activators, Glp-1 receptor agonists, GIP receptor agonists, DGAT inhibitors, PPARgamma agonists, PPARdelta agonists, and other antidiabetics derived from thiazolidinediones, lipid lowering agents such as statines, fibrates, ion exchange resins nicotinic acid derivatives, or HMG-CoA reductase inhibitors, cardiovascular therapeutics such as nitrates, antihypertensiva such as β-blockers, ACE inhibitors, Ca-channel blockers, angiotensin II receptor antagonists, diuretics, thrombocyte aggregation inhibitors, or antineoplastic agents such as alkaloids, alkylating agents, antibiotics, or antimetabolites, or anti-obesity agents. Further preferred compositions are compositions wherein the additional therapeutic agent is selected from a histamine antagonist, a bradikinin antagonist, serotonin antagonist, leukotriene, an anti-asthmatic, an NSAID, an antipyretic, a corticosteroid, an antibiotic, an analgetic, a uricosuric agent, chemotherapeutic agent, an anti gout agent, a bronchodilator, a cyclooxygenase-2 inhibitor, a steroid, a 5-lipoxygenase inhibitor, an immunosuppressive agent, a leukotriene antagonist, a cytostatic agent, an antineoplastic agent, a mTor inhibitor, a Tyrosine kinase inhibitor, antibodies or fragments thereof against cytokines and soluble parts (fragments) of cytokine receptors.

More particularly preferred are compounds such as human NPH insulin, human lente or ultralente insulin, insulin Lispro, insulin Aspart, insulin Glulisine, insulin detemir or insulin Glargine, metformin, phenformin, acarbose, miglitol, voglibose, pioglitazone, rosiglizatone, rivoglitazone, aleglitazar, alogliptin, saxagliptin, sitagliptin, vildagliptin, exenatide, liraglutide, albiglutide, pramlintide, carbutamide, chlorpropamide, glibenclamide (glyburide), gliclazide, glimepiride, glipizide, gliquidone, tolazamide, tolbutamide, atenolol, bisoprolol, metoprolol, esmolol, celiprolol, talinolol, oxprenolol, pindolol, propanolol, bupropanolol, penbutolol, mepindolol, sotalol, certeolol, nadolol, carvedilol, nifedipin, nitrendipin, amlodipin, nicardipin, nisoldipin, diltiazem, enalapril, verapamil, gallopamil, quinapril, captopril, lisinopril, benazepril, ramipril, peridopril, fosinopril, trandolapril, irbesatan, losartan, valsartan, telmisartan, eprosartan, olmesartan, hydrochlorothiazide, piretanid, chlorotalidone, mefruside, furosemide, bendroflumethiazid, triamterene, dehydralazine, acetylsalicylic acid, tirofiban-HCl, dipyramidol, triclopidin, iloprost-trometanol, eptifibatide, clopidogrel, piratecam, abciximab, trapidil, simvastatine, bezafibrate, fenofibrate, gemfibrozil, etofyllin, clofibrate, etofibrate, fluvastatine, lovastatine, pravastatin, colestyramide, colestipol-HCl, xantinol nicotinat, inositol nicotinat, acipimox, nebivolol, glyceroInitrate, isosorbide mononitrate, isosorbide dinitrate, pentaerythrityl tetranitrate, indapamide, cilazepril, urapidil, eprosartan, nilvadipin, metoprolol, doxazosin, molsidormin, moxaverin, acebutolol, prazosine, trapidil, clonidine, vinca alkaloids and analogues such as vinblastin, vincristin, vindesin, vinorelbin, podophyllotoxine derivatives, etoposid, teniposid, alkylating agents, nitroso ureas, N-lost analogues, cycloplonphamid, estamustin, melphalan, ifosfamid, mitoxantron, idarubicin, doxorubicin, bleomycin, mitomycin, dactinomycin, daptomycin, docetaxel, paclitaxel, carboplatin, cisplatin, oxaliplatin, BBR3464, satraplatin, busulfan, treosulfan, procarbazine, dacarbazine, temozolomide, chlorambucil, chlormethine, cyclophosphamide, ifosfamide, melphalan, bendamustine, uramustine, ThioTEPA, camptothecin, topotecan, irinotecan, rubitecan, etoposide, teniposide, cetuximab, panitumumab, trastuzumab, rituximab, tositumomab, alemtuzumab, bevacizumab, gemtuzumab, aminolevulinic acid, methyl aminolevulinate, porfimer sodium, verteporfin, axitinib, bosutinib, cediranib, dasatinib, erlotinib, gefitinib, imatinib, lapatinib, lestaurtinib, nilotinib, semaxanib, sorafenib, sunitinib, vandetanib, retinoids (alitretinoin, tretinoin), altretamine, amsacrine, anagrelide, arsenic trioxide, asparaginase (pegaspargase), bexarotene, bortezomib, denileukin diftitox, estramustine, ixabepilone, masoprocol, mitotane, testolactone, tipifarnib, abetimus, deforolimus, everolimus, gusperimus, pimecrolimus, sirolimus, tacrolimus, temsirolimus, antimetabolites such as cytarabin, fluorouracil, fluoroarabin, gemcitabin, tioguanin, capecitabin, combinations such as adriamycin/daunorubicin, cytosine arabinosid/cytarabine, 4-HC, or other phosphamides.

Other particularly preferred compounds are compounds such as clemastine, diphenhydramine, dimenhydrinate, promethazine, cetirizine, astemizole, levocabastine, loratidine, terfenadine, acetylsalicylic acid, sodoum salicylate, salsalate, diflunisal, salicylsalicylic acid, mesalazine, sulfasalazine, osalazine, acetaminophen, indomethacin, sulindac, etodolac, tolmetin, ketorolac, bethamethason, budesonide, chromoglycinic acid, dimeticone, simeticone, domperidone, metoclopramid, acemetacine, oxaceprol, ibuprofen, naproxen, ketoprofen, flubriprofen, fenoprofen, oxaprozin, mefenamic acid, meclofenamic acid, pheylbutazone, oxyphenbutazone, azapropazone, nimesulide, metamizole, leflunamide, eforicoxib, lonazolac, misoprostol, paracetamol, aceclofenac, valdecoxib, parecoxib, celecoxib, propyphenazon, codein, oxapozin, dapson, prednisone, prednisolon, triamcinolone, dexibuprofen, dexamethasone, flunisolide, albuterol, salmeterol, terbutalin, theophylline, caffeine, naproxen, glucosamine sulfate, etanercept, ketoprofen, adalimumab, hyaluronic acid, indometacine, proglumetacine dimaleate, hydroxychloroquine, chloroquine, infliximab, etofenamate, auranofin, gold, [$^{224}$Ra]radium chloride, tiaprofenic acid, dexketoprofen(trometamol), cloprednol, sodium aurothiomalate aurothioglucose, colchicine, allopurinol, probenecid, sulfinpyrazone, benzbromarone, carbamazepine, lornoxicam, fluorcortolon, diclofenac, efalizumab, idarubicin, doxorubicin, bleomycin, mitomycin, dactinomycin, daptomycin, cytarabin, fluorouracil, fluoroarabin, gemcitabin, tioguanin, capecitabin, adriamydin/daunorubicin, cytosine arabinosid/cytarabine, 4-HC, or other phosphamides, penicillamine, a hyaluronic acid preparation, arteparon, glucosamine, MTX, soluble fragments of the TNF-receptor (such as etanercept (Enbrel)) and antibodies against TNF (such as infliximab (Remicade), natalizumab (Tysabri) and adalimumab (Humira)).

It will be appreciated by the person of ordinary skill in the art that the compounds of the invention and the additional therapeutic agent may be formulated in one single dosage form, or may be present in separate dosage forms and may be either administered concomitantly (i.e. at the same time) or sequentially.

The pharmaceutical compositions of the present invention may be in any form suitable for the intended method of administration.

The compounds of the present invention may be administered orally, parenterally, such as bronchopulmonary, subcutaneously, intravenously, intramuscularly, intraperitoneally, intrathecally, transdermally, transmucosally, subdurally, locally or topically via iontopheresis, sublingually, by inhalation spray, aerosol or rectally and the like in dosage unit formulations optionally comprising conventional pharmaceutically acceptable excipients.

Excipients that may be used in the formulation of the pharmaceutical compositions of the present invention comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins.

Other suitable pharmaceutically acceptable excipients are described in *Remington's Pharmaceutical Sciences,* 15$^{th}$ Ed., Mack Publishing Co., New Jersey (1991).

Dosage forms for oral administration include tablets, capsules, lozenges, pills, wafers, granules, oral liquids such as syrups, suspensions, solutions, emulsions, powder for reconstitution.

Dosage forms for parenteral administration include aqueous or olageous solutions or emulsions for infusion, aqueous or olageous solutions, suspensions or emulsions for injection pre-filled syringes, and/or powders for reconstitution.

Dosage forms for local/topical administration comprise insufflations, aerosols, metered aerosols, transdermal therapeutic systems, medicated patches, rectal suppositories, and/or ovula.

The amount of the compound of the present invention that may be combined with the excipients to formulate a single dosage form will vary upon the host treated and the particular mode of administration.

The pharmaceutical compositions of the invention can be produced in a manner known per se to the skilled person as described, for example, in Remington's Pharmaceutical Sciences, 15$^{th}$ Ed., Mack Publishing Co., New Jersey (1991).

In a further aspect of the invention the use of a thienopyrimidine compound of the present invention for the production of a pharmaceutical composition for inhibiting the activity of the kinase activity of Mnk1 or Mnk2 (Mnk2a, Mnk2b) or further variants thereof is provided, in particular for the prophylaxis or therapy of metabolic diseases, hematopoietic disorders, cancer and their consecutive complications and disorders.

Whereby the prophylaxis and therapy of metabolic diseases of the carbohydrate and/or lipid metabolism is preferred.

Diseases of the invention that are influenced by the inhibition of the kinase activity of Mnk1 and/or Mnk2 (Mnk2a or Mnk2b) and/or further variants thereof include diseases related to the regulation of metabolic diseases, such as obesity, eating disorders, cachexia, diabetes mellitus, metabolic syndrome, hypertension, coronary heart diseases, hypercholesterolemia, dyslipidemia, osteoarthritis, biliary stones and/or sleep apnea and diseases related to reactive oxygen compounds (ROS defense) such as diabetes mellitus, neurodegenerative diseases and cancer.

The pharmaceutical compositions of the invention are particularly useful for prophylaxis and treatment of obesity, diabetes mellitus and other metabolic diseases of the carbohydrate and lipid metabolism as stated above, in particular diabetes mellitus and obesity.

Thus in a more preferred embodiment of this invention the use of a thienopyrimidine compound for the production of a pharmaceutical composition for the prophylaxis or therapy of metabolic diseases is provided.

In yet a further aspect of the invention the use of a thienopyrimidine compound of the invention for the production of a pharmaceutical composition for treating or preventing a cytokine mediated disorder such as an inflammatory disease is provided.

The pharmaceutical compositions of the invention are thus useful for the prophylaxis or therapy of inflammatory diseases, in particular chronic or acute inflammation, chronic inflammatory arthritis, rheumatoid arthritis, psoriatic arthritis, osteoarthritis, juvenile rheumatoid arthritis, gouty arthritis; psoriasis, erythrodermic psoriasis, pustular psoriasis, inflammatory bowel disease, Crohn's disease and related conditions, ulcerative colitis, colitis, diverticulitis, nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, chronic obstructive disease (COPD), inflammatory lung disease, allergic rhinitis, endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjubctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, dermatitis, endomyometritis, myometritis, metritis, cervicitis, endocervicitis, exocervicitis, parametritis, tuberculosis, vaginitis, vulvitis, silicosis, sarcoidosis, pneumoconiosis, inflammatory polyarthropathies, psoriatric arthropathies, intestinal fibrosis, bronchiectasis and enteropathic arthropathies.

As already stated above, the compositions of the present invention are particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Thus, in a more preferred embodiment of this invention the use of a thienopyrimidine compound for the production of a pharmaceutical composition for the prophylaxis or therapy of inflammatory diseases selected from chronic or acute inflammation, chronic inflammatory arthritis, rheumatoid arthritis, psoriasis, COPD, inflammatory bowel disease, septic shock Crohn's disease, ulcerative colitis, multiple sclerosis and asthma is provided.

In yet a further aspect of the invention the use of a thienopyrimidine compound of the invention for the production of a pharmaceutical composition for treating or preventing cancer, viral diseases or neurodegenerative diseases is provided.

For the purpose of the present invention, a therapeutically effective dosage will generally be from about 1 to 2000 mg/day, preferably from about 10 to about 1000 mg/day, and most preferably from about 10 to about 500 mg/day, which may be administered in one or multiple doses.

It will be appreciated, however, that specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician.

Abbreviations:
CDI: carbonyldiimidazole
TEA: triethylamine
HATU: (2-(7-aza-1H-benzotriazole-1-yl)-1,1,3,3-tetramethyluronium hexafluorophosphate)
TBTU: 2-(1H-Benzotriazol-1-yl)-1,1,3,3-tetramethyluroniumtetrafluorborat
THF: tetrahydrofuran
EE: ethylacetate
ACN: acetonitrile
EtOH: ethanol
MeOH: methanol
DCM: methylene chloride
DMF: N,N-dimethylformamide
EtOAc: ethyl acetate
HCl: hydrochloric acid
t-BuOH: tert.butanol
DTAD: Di-ter-butyl azodicarboxylate
DEAD: diethyl azodicarboxylate
DIAD: diisopropyl azodicarboxylate
LiHMDS: lithium hexymethyldisilazane
DIPEA: diisopropylethyl amine
EDC: 1-ethyl-3-(3-dimethylaminopropyl)carbodiimid TFA: trifluoro acetic acid
brine: saturated sodium chloride solution in water
rt: room temperature
min: minute

EXAMPLES

Intermediate I tert-Butyl 2-(2-amino-5-fluorophenoxy)propylcarbamate

I.1. tert-Butyl 2-(5-fluoro-2-nitrophenoxy)propylcarbamate

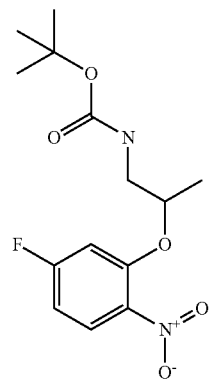 [SMILES: CC(CNC(=O)OC(C)(C)C)Oc1cc(F)ccc1[N+](=O)[O-]]

2-Nitro-5-fluorophenol (3.0 g) and tert-butyl-N-(2-hydroxypropyl)carbamate were dissolved in THF (20 ml) and triphenylphosphine (7.5 g) and di-tert-butyl-azodicarboxylate were added. The exothermic reaction was cooled in an ice bath. Then the reaction mixture was stirred at room temperature for 2 h. The mixture was concentrated in vacuo and the residue was purified by chromatography (silica gel/dichloromethane: petroleum ether 1:2). The fractions were combined and concentrated in vacuo. The residue was dissolved in dichloromethane and washed with 1M NaOH. The organic layer was separated, dried, filtered and concentrated in vacuo.

Yield: 3.12 g
ESI mass spectrum: m/z=315 (M+H)$^+$

I.2: tert-Butyl 2-(2-amino-5-fluorophenoxy)propylcarbamate

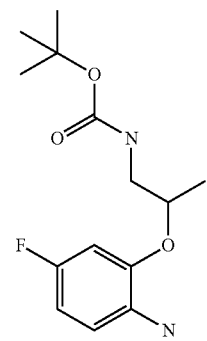 [SMILES: CC(CNC(=O)OC(C)(C)C)Oc1cc(F)ccc1N]

To a solution of tert-butyl 2-(5-fluoro-2-nitrophenoxy)propylcarbamate (3.1 g) in MeOH (5 ml) was added 10% palladium on carbon (300 mg) and the reaction mixture was hydrogenated at room temperature at 50 psi. The catalyst was filtered off and the filtrate was concentrated in vacuo.

Yield: 2.5 g
ESI mass spectrum: m/z=285 (M+H)$^+$

Intermediate II Tert-butyl 2-hydroxybutylcarbamate

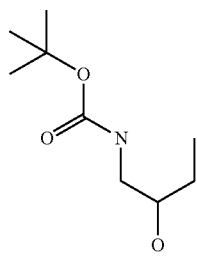

1-Amino-2-butanol (1.0 g) was dissolved in dichloromethane (50.0 ml) and di-(tert-butyl) dicarbonate (2.6 g) was added. The reaction mixture was stirred at room temperature for 4 h then washed with 1M NaOH. The organic layer was separated and concentrated in vacuo.
Yield: 1.8 g

Intermediate III Methyl 4-(4-fluoro-2-hydroxyphenylamino)-5-methyl-thieno[2,3-d]pyrimidine-6-carboxylate

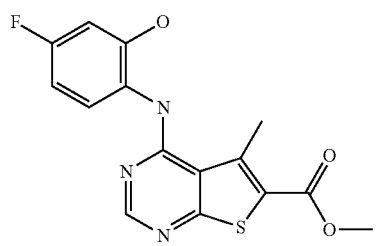 [SMILES: COC(=O)c1sc2ncnc(Nc3ccc(F)cc3O)c2c1C]

4-Chloro-5-methyl-thieno[2,3-d]pyrimidine-6-carboxylic acid methyl ester (0.5 g), 2-amino-5-fluorophenol (265.0 mg), p-toluenesulfonic acid monohydrate (75.0 mg) and dioxane (5.0 ml) were combined in a microwave tube. The mixture was heated at 140° C. for 15 min under microwave irradiation. Then the mixture was allowed to cool to room temperature and a precipitate formed. The precipitate was collected by filtration, washed with dioxane, methanol and Et$_2$O to yield the title compound.
Yield: 605.0 mg
ESI mass spectrum: m/z=334 (M+H)$^+$

Intermediate IV

Methyl 4-(2-hydroxypyridin-3-ylamino)-5-methylthieno[2,3-d]pyrimidine-6-carboxylate

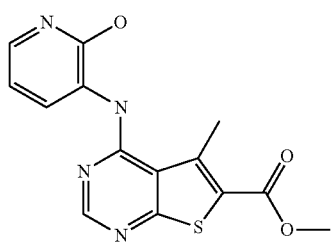 [SMILES: COC(=O)c1sc2ncnc(Nc3cccnc3O)c2c1C]

Prepared analogously to example III using 4-chloro-5-methyl-thieno[2,3-d]pyrimidine-6-carboxylic acid methyl ester and 3-amino-2-hydroxypyridine
Yield: 258.0 mg
ESI mass spectrum: m/z=317 (M+H)$^+$

Intermediate V tert-Butyl 3-(2-amino-5-fluorophenoxy)butylcarbamate

V.1 tert-Butyl 2-(5-fluoro-2-nitrophenoxy)butylcarbamate

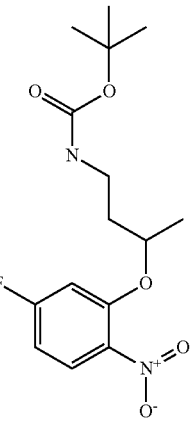

Prepared analogously to example I-1 using BOC-4-amino-2-butanol and 2-nitro-5-fluorophenol.
Yield: 2.20 g
ESI mass spectrum: m/z=329 (M+H)$^+$

V.2 tert-Butyl 3-(2-amino-5-fluorophenoxy)butylcarbamate

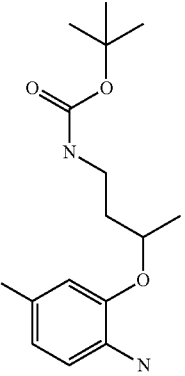

Prepared analogously to example 1-2 using tert-butyl 3-(5-fluoro-2-nitrophenoxy)butylcarbamate
Yield: 1.8 g

Intermediate VI 3-(2-Amino-5-fluoro-phenoxy)-butyric acid ethyl ester

Intermediate VI.1 Ethyl 3-(5-fluoro-2-nitrophenoxy)butanoate

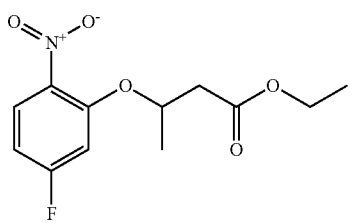 [SMILES: CCOC(=O)CC(C)Oc1cc(F)ccc1[N+](=O)[O-]]

Ethyl 3-Hydroxybutyrate (6.5 ml) was dissolved in THF (350.0 ml) at 0° C. and NaH (4.8 g) was added. The reaction was stirred at room temperature for 30 min. Then 5.5 g 2,4-difluoronitrobenzene was added and the mixture was heated at reflux overnight. The reaction was concentrated in vacuo and the residue was dissolved in water and dichloromethane. The organic layer was separated, dried and concentrated in vacuo. The residue was purified by chromatography (silica/dichloromethane) to yield the title compound.

Yield: 1.36 g

ESI mass spectrum: m/z=272 (M+H)+

VI. 2 3-(2-Amino-5-fluoro-phenoxy)-butyric acid ethyl ester

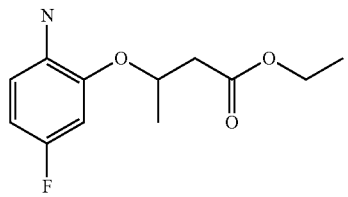 [SMILES: CCOC(=O)CC(C)Oc1cc(F)ccc1N]

To a solution of Ethyl 3-(5-fluoro-2-nitrophenoxy)butanoate (1.3 g) in THF (50 ml) was added Raney nickel (150 mg) and the reaction mixture was hydrogenated. The catalyst was filtered off and the filtrate was concentrated in vacuo.

Yield: 2.5 g

ESI mass spectrum: m/z=285 (M+H)+

Intermediate VII

[2-(2-Amino-5-fluoro-phenoxy)-3-tert-butoxycarbonylamino-propyl]-carbamic acid tert-butyl ester

VII.1 (3-tert-Butoxycarbonylamino-2-hydroxy-propyl)-carbamic acid tert-butyl ester

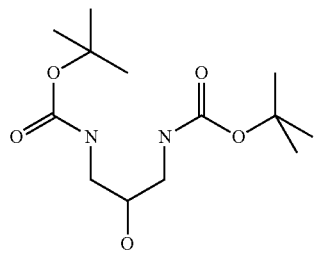 [SMILES: CC(C)(C)OC(=O)NCC(O)CNC(=O)OC(C)(C)C]

Di-tert-butyl dicarbonate (41.5 g) was dissolved in dichloromethane (40.0 ml), a solution of 1,3-diamino-propan-2-ol (8.0 g) and triethylamine (1.5 ml) in dichloromethane/methanol (1:5; 100 ml) was added and the reaction mixture was stirred at room temperature overnight. The solution was concentrated in vacuo and the residue was dissolved in dichlormethane. The organic layer was washed with water, separated, dried and concentrated in vacuo. The residue was purfied by chromatography (silica/dichloromethane:methanol 25:1).

Yield: 17 g

ESI mass spectrum: m/z=291 (M+H)+

VII. 2 [3-tert-Butoxycarbonylamino-2-(5-fluoro-2-nitro-phenoxy)-propyl]-carbamic acid tert-butyl ester

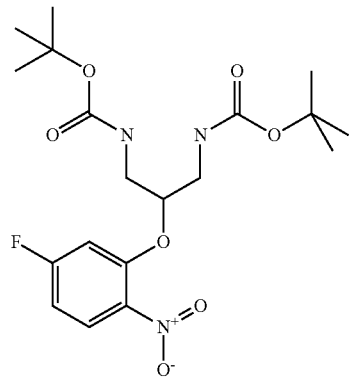 [SMILES: CC(C)(C)OC(=O)NCC(CNC(=O)OC(C)(C)C)Oc1cc(F)ccc1[N+](=O)[O-]]

2-Nitro-5-fluorophenol (8.4 g) and (3-tert-butoxycarbonylamino-2-hydroxy-propyl)-carbamic acid tert-butyl ester (17.0 g) were dissolved in THF (60 ml) and triphenylphosphine (21 g) and di-tert-butyl-azodicarboxylate (18.4 g) were added. The exothermic reaction was cooled in an ice bath. Then the mixture was stirred at room temperature overnight. It was concentrated in vacuo and the residue was dissolved in dichloromethane, washed with water and 1M NaOH. The organic layer was dried and concentrated in vacuo. The residue was purified by chromatography (silica/dichloromethane:methanol 25:1).

Yield: 25 g

ESI mass spectrum: m/z=430 (M+H)+

VII.3 [2-(2-Amino-5-fluoro-phenoxy)-3-tert-butoxycarbonylamino-propyl]-carbamic acid tert-butyl ester

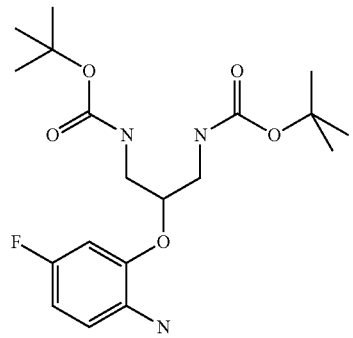 [SMILES: CC(C)(C)OC(=O)NCC(CNC(=O)OC(C)(C)C)Oc1cc(F)ccc1N]

Prepared analogously to example 1-2 using [3-tert-butoxycarbonylamino-2-(5-fluoro-2-nitro-phenoxy)-propyl]-carbamic acid tert-butyl ester Yield: 12.7 g ESI mass spectrum: m/z=400 (M+H)+

Intermediate VIII 4-(2-amino-5-fluorophenoxy)-2-methylpentan-2-ol

VIII.1
4-(5-fluoro-2-nitrophenoxy)-2-methylpentan-2-ol

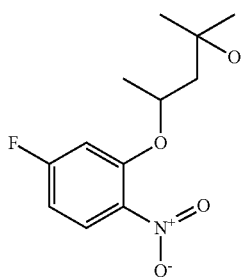

2-Methylpentane-2,4-diol (2.8 ml) was dissolved in THF (20.0 ml) and NaH (60% in mineral oil; 1 g) was added. At room temperature 2,4-difluoronitrobenzene was added and the reaction mixture was stirred overnight. Then the reaction was quenched with water and concentrated in vacuo. The residue was dissolved in dichloromethane, washed with water and concentrated in vacuo.
Yield: 2.4 g
ESI mass spectrum: m/z=258 (M+H)$^+$ VIII. 2
4-(2-amino-5-fluorophenoxy)-2-methylpentan-2-ol

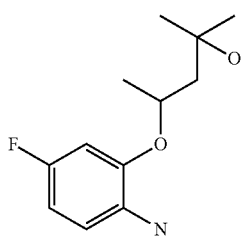

Prepared analogously to example 1-2 using 4-(5-fluoro-2-nitrophenoxy)-2-methylpentan-2-ol
Yield: 2.12 g
ESI mass spectrum: m/z=228 (M+H)$^+$

Intermediate IX 2-(1,1,1-Trifluoropropan-2-yloxy)pyridin-3-amine

IX.1
3-Nitro-2-(1,1,1-trifluoropropan-2-yloxy)pyridine

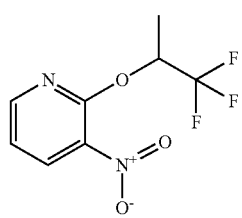 [SMILES: CC(Oc1ncccc1[N+](=O)[O-])C(F)(F)F]

1,1,1-Trifluoro-2-propanol (3.2 g) was dissolved in THF (4.0 ml) and cooled to 0° C. Then LiHMDS (1M in THF; 28.3 ml) was added dropwise. The reaction mixture was stirred at 0° C. for 20 minutes. A solution of 2-fluoro-3-nitro-pyridine (4.0 g) in THF (1 ml) was added and the mixture was stirred overnight. It was quenched by addition of saturated NH$_4$Cl solution and extracted with dichloromethane. The organic layer was dried and concentrated in vacuo.
Yield: 6.24 g
ESI mass spectrum: m/z=237 (M+H)$^+$ IX. 2
2-(1,1,1-Trifluoropropan-2-yloxy)pyridin-3-amine

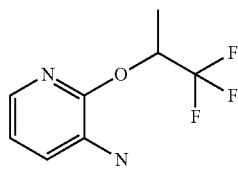

3-Nitro-2-(1,1,1-trifluoropropan-2-yloxy)pyridine (6.2 g) was dissolved in methanol (500 ml) and Raney nickel (1.0 g) was added. The reaction mixture was hydrogenated at room temperature and 5 bar. The catalyst was filtered off and the filtrate was concentrated in vacuo.
Yield: 4.83 g
ESI mass spectrum: m/z=207 (M+H)$^+$

Intermediate X 2-(1,3-Difluoropropan-2-yloxy)-4-fluoroaniline

X. 1 2-(1,3-Difluoropropan-2-yloxy)-4-fluoro-1-nitrobenzene

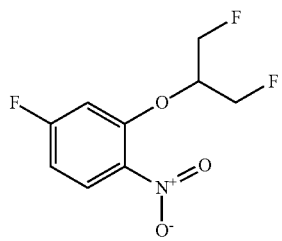 [SMILES: O=[N+]([O-])c1ccc(F)cc1OC(CF)CF]

Prepared analogously to example 1X.1 using 2,4-difluoronitrobenzene.
Yield: 11.96 g X. 2 2-(1,3-Difluoropropan-2-yloxy)-4-fluoroaniline

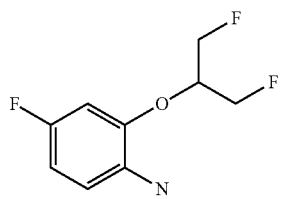 [SMILES: Nc1ccc(F)cc1OC(CF)CF]

Prepared analogously to example IX. 2
Yield: 4.42 g
ESI mass spectrum: m/z=206 (M+H)$^+$

Intermediate XI 2-(2-Fluoropropoxy)pyridin-3-amine

XI.1 2-(2-fluoropropoxy)-3-nitropyridine

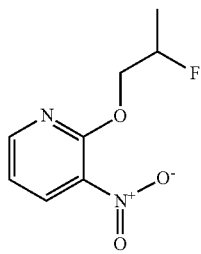

2-Fluoropropan-1-ol (93.6 mg) was dissolved in THF (10 ml). LiHMDS in THF(1M; 1.2 ml) was added and the reaction was stirred for 15 min. Then a solution of 2-fluoro-3-nitro-pyridine (142 mg) in THF was added and the reaction stirred at room temperature overnight.

An aqueous solution of $K_2CO_3$ (2M; 750 µl) was added to the reaction mixture and filtered over Alox B. The filtrat was concentrated in vacuo.
Yield: 200 mg
Retention time HPLC: 2.05 min
HPLC method: 003_CC_ZQ6

XI.2 2-(2-Fluoropropoxy)pyridin-3-amine

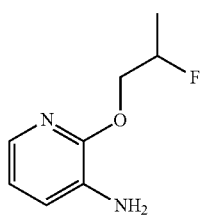

2-(2-fluoropropoxy)-3-nitropyridine (199.97 mg) was dissolved in a mixture of THF (10 ml) and methanol (5 ml). Pd/C (20 mg) was added and the mixture was hydrogenated at room temperature for 4 h and 3 bar. The mixture was concentrated in vacuo.
Yield: 153 mg
Retention time HPLC: 1.50 min
HPLC method: 002_CC_ZQ4

Intermediate XII 2-(1-methoxypropan-2-yloxy)pyridin-3-amine

XII.1 2-(1-methoxypropan-2-yloxy)-3-nitropyridine

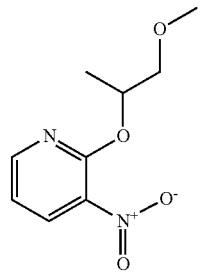

Prepared analogously to example XI.1 using 2-fluoro-3-nitropyridine (142 mg) and 1-methoxypropan-2-ol (108 mg).
Yield: 212 mg
Retention time HPLC: 2.04 min
HPLC method: 003_CC_ZQ6

XII.1 2-(1-Methoxypropan-2-yloxy)pyridin-3-amine

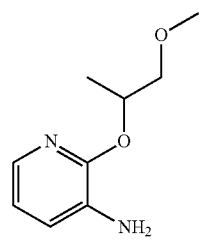

Prepared analogously to example XI.2 using 2-(1-methoxypropan-2-yloxy)-3-nitropyridine (212 mg).
Yield: 165 mg
Retention time HPLC: 1.52 min
HPLC method: 002_CC_ZQ4

Intermediate XIII 2-(3-Aminopyridin-2yloxy)ethanol

XIII.1 2-(3-Nitropyridin-2-yloxy)ethanol

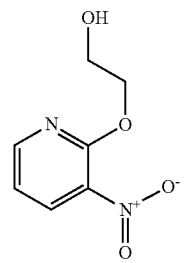

Ethylene glycole (88.8 mg) was dissolved in THF (10 ml). LiHMDS in THF(1M; 1.2 ml) was added and the reaction was stirred for 15 min. Then a solution of 2-fluoro-3-nitro-pyridine (142 mg) in THF was added and the reaction was stirred at room temperature overnight.

The reaction mixture was concentrated in vacuo and the residue was purified by RP-chromatography (H2O+0.1% TFA/MeOH=40%-->99%).
Yield: 176 mg
Retention time HPLC: 1.68 min
HPLC method: 003_CC_ZQ6

XIII.2 2-(3-Aminopyridin-2yloxy)ethanol

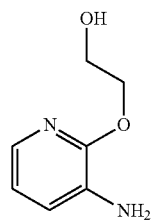

Prepared analogously to example XII.2 using 2-(3-nitro-pyridin-2-yloxy)ethanol (115 mg).
Yield: 175 mg
Retention time HPLC: 1.43 min
HPLC method: 003_CC_ZQ7

Intermediate XIV 2-(2,2-Difluoroethoxy)pyridin-3-amine

XIV.1 2-(2,2-Difluoroethoxy)-3-nitropyridine

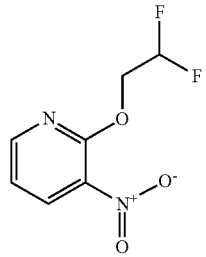 [SMILES: O=[N+]([O-])c1cccnc1OCC(F)F]

Prepared analogously to example XII.1 using 2-fluoro-3-nitropyridine (142 mg) and 2,2-difluoroethanol (98 mg).
Yield: 204 mg
Retention time HPLC: 1.99 min
HPLC method: 003_CC_ZQ6

XIV.2 2-(2,2-Difluoroethoxy)pyridin-3-amine

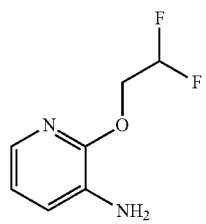

Prepared analogously to example XII.2 using 2-(2,2-difluoroethoxy)-3-nitropyridine (204 mg).
Yield: 171 mg
Retention time HPLC: 1.58 min
HPLC method: 002_CC_ZQ4

Intermediate XV 2-((3-Aminopyridin-2-yloxy)methyl)propane-1,3-diol

XV.1
2-((3-Nitropyridin-2-yloxy)methyl)propane-1,3-diol

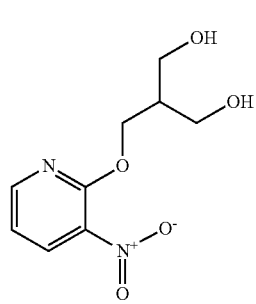 [SMILES: O=[N+]([O-])c1cccnc1OCC(CO)CO]

Prepared analogously to example XII.1 using 2-fluoro-3-nitropyridine (142 mg) and 2-(hydroxymethyl)-1,3-propanediol (148 mg)
Yield: 130 mg
Retention time HPLC: 1.65 min
HPLC method: 003_CC_ZQ6

XV.2
2-((3-Aminopyridin-2-yloxy)methyl)propane-1,3-diol

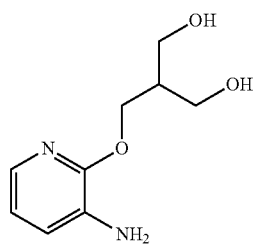 [SMILES: Nc1cccnc1OCC(CO)CO]

Prepared analogously to example XII.2 using 2-((3-nitropyridin-2-yloxy)methyl)propane-1,3-diol (130 mg).
Yield: 99 mg

Intermediate XVI 2-(1-((3-Aminopyridin-2-yloxy)methyl)cyclopropyl)acetonitrile XVI.1 2-(1-((3-Nitropyridin-2-yloxy)methyl)cyclopropyl)acetonitrile

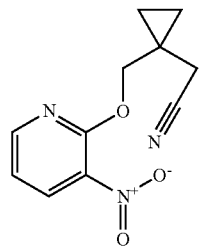 [SMILES: N#CCC1(COc2ncccc2[N+](=O)[O-])CC1]

Prepared analogously to example XI.1 using [1-(hydroxymethyl)cyclopropyl]acetonitrile (267 mg)
Yield: 488 mg
Retention time HPLC: 1.82 min
HPLC method: 004_CC_ZQ6

XVI.2 2-(1-((3-Aminopyridin-2-yloxy)methyl)cyclopropyl)acetonitrile

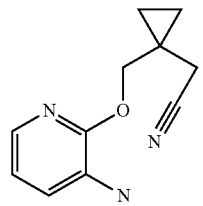 [SMILES: N#CCC1(COc2ncccc2N)CC1]

2-(1-((3-Nitropyridin-2-yloxy)methyl)cyclopropyl)acetonitrile (466 mg) was dissolved in a mixture of glacial acetic acid (4 ml) and ethanol (8 ml). Ferrum (1.1 g) was added and the reaction mixture was heated to 100° C. for 2 h. The mixture was concentrated in vacuo and the residue was dissolved in dichloromethane, extracted with an aqueous solution of $K_2CO_3$ (2M) and concentrated in vacuo
Yield: 264 mg
Retention time HPLC: 2.07 min
HPLC method: 003_CC_ZQ7

Intermediate XVII 2-((2,2-Difluorocyclopropyl)methoxy)pyridine-3-amine

XVII.1 2-((2,2-Difluorocyclopropyl)methoxy)-3-nitropyridine

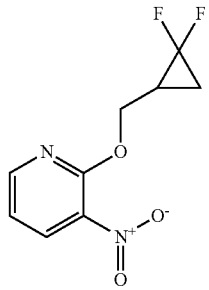 [SMILES: O=[N+]([O-])c1cccnc1OCC1CC1(F)F]

Prepared analogously to example XII.1 using (2,2-difluorocyclopropyl)methanol and 2-fluoro-3-nitro-pyridine
Yield: 469 mg
Retention time HPLC: 2.00 min
HPLC method: 004_CC_ZQ6

XVII.2 2-((2,2-Difluorocyclocropyl)methoxy)pyridine-3-amine

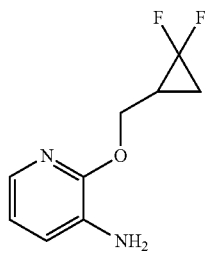 [SMILES: Nc1cccnc1OCC1CC1(F)F]

Prepared analogously to example XII.2 using 2-((2,2-difluorocyclopropyl)methoxy)-3-nitropyridine
Yield: 391 mg
Retention time HPLC: 1.45 min
HPLC method: 004_CC_ZQ6

Intermediate XVIII

4-[2-(1-Ethylcabamoyl-ethoxy)-4-fluoro-phenylamino]-5-methyl-thieno[2,3d]pyrimidine-6-carboxylic acid methyl ester

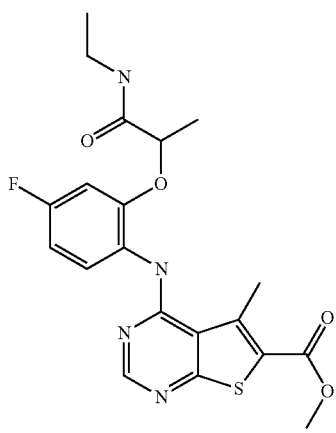 [SMILES: CCNC(=O)C(C)Oc1cc(F)ccc1Nc1ncnc2sc(C(=O)OC)c(C)c12]

XVIII.1 4-(4-fluoro-2-methoxy-phenylamino)-5-methyl-thieno[2,3-d]pyrimidine-6-carboxylic acid methyl ester

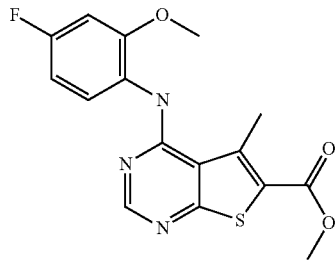 [SMILES: COC(=O)c1sc2ncnc(Nc3ccc(F)cc3OC)c2c1C]

4-Chloro-5-methyl-thieno[2,3-d]pyrimidine-6-carboxylic acid methyl ester (15.0 g), 4-fluoro-2-methoxyaniline (9.5 g), 4M hydrochloric acid in dioxane (4.5 ml) and dioxane (100.0 ml) were stirred at 100° C. overnight. Then the mixture was filtrated and the solid was dried in vacuo.

Yield: 24.0 g

ESI mass spectrum: m/z=348 (M+H)$^+$

XVI11.2 4-(4-Fluoro-2-hydroxy-phenylamino)-5-methyl-thieno[2,3-d]pyrimidine-6-carboxylic acid methyl ester

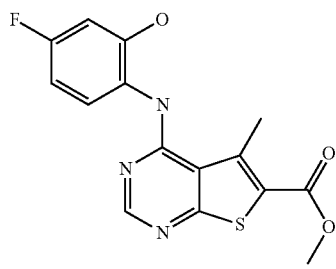 [SMILES: COC(=O)c1sc2ncnc(Nc3ccc(F)cc3O)c2c1C]

The resulting product from XVIII.1 (24.0 g) was dissolved in DCM (500 ml) and was cooled with a dry ice bath. To the mixture was dropped slowly boron tribromide (35 ml) and stirred for 30 min. The mixture was allowed to cool to room temperature overnight. Then the mixture was cooled with an dry ice bath, dropped 100 ml methanol to the mixture, stirred for 30 min and concentrated. The residue was suspended in methonol and stirred at reflux for 1 hour. The mixture was filtrated and dried in vacuo.

Yield: 18.6 g

ESI mass spectrum: m/z=334 (M+H)$^+$

Retention time HPLC: 2.16 min

HPLC method: 007_CC_ZQ5

XVIII.3 4-[2-(1-tert-Butoxycyrbonyl-ethoxy)-4-fluoro-phenylamino]-5-methyl-thieno[2,3-d]pyrimidine-6-carboxylic acid methyl ester

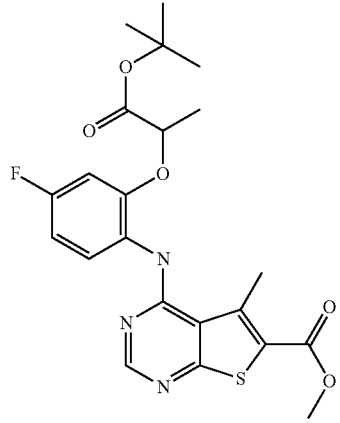

To the resulting product from XVI11.2 (2.0 g) was added 2-bromopropionic acid tert-butyl ester (1.4 g), cesium carbonate (4.8 g) and ACN (50 ml). The mixture was stirred at 60° C. for 2 hours. Then water was added and the mixture was filtrated.
Yield: 2.1 g
ESI mass spectrum: m/z=462 (M+H)+

XVIII.4 4-[2-(1-Carboxy-ethoxy)-4-fluoro-phenylamino]-5-methyl-thieno[2,3-d]pyrimidine-6-carboxylic acid methyl ester

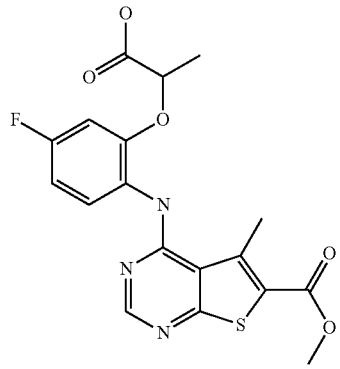 [SMILES: COC(=O)c1sc2ncnc(Nc3ccc(F)cc3OC(C)C(=O)O)c2c1C]

To the resulting product from XVI11.3 (2.1 g) was added trifluoroacetic acid 50% in DCM (20 ml) and stirred at rt overnight. The mixture was concentrated and triturated with diethylether.
Yield: 1.9 g
ESI mass spectrum: m/z=406 (M+H)+
Retention time HPLC: 1.96 min
HPLC method: Method A 9

XVIII.5 4-[2-(1-Ethylcarbamoyl-ethoxy)-4-fluoro-phenylamino]-5-methyl-thieno[2,3-d]pyrimidine-6-carboxylic acid methyl ester

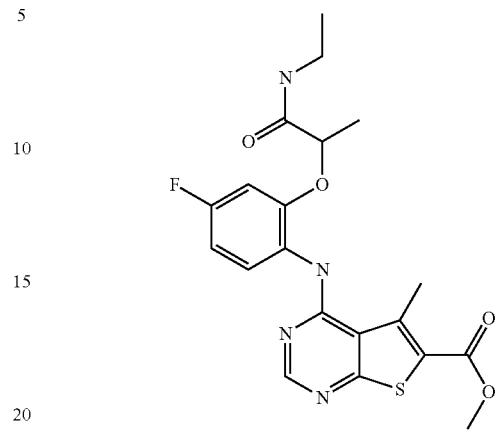

To the resulting product from XVI11.4 (0.5 g) in ACN (10 ml) was added TBTU (0.4 g) and TEA (0.43 ml). The mixture was stirred at rt for 20 min. To the mixture was added ethylamine (2 mol/l (1.5 ml)) and stirred at rt overnight. Then the mixture was concentrated and triturated with diethylether. The mixture was diluted with methanol and purified by chromatography.
Yield: 0.36 g
ESI mass spectrum: m/z=433 (M+H)+
Retention time HPLC: 1.89 min
HPLC method: Method A 9

Intermediate XIX

4-Amino-3-(2-fluoro-1-fluoromethyl-ethoxy)-benzonitrile

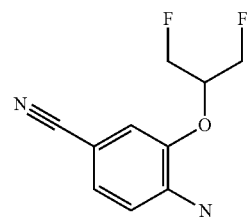 [SMILES: N#Cc1ccc(N)c(OC(CF)CF)c1]

XIX.1 3-(2-Fluoro-1-fluoromethyl-ethoxy)-4-nitrobenzonitrile

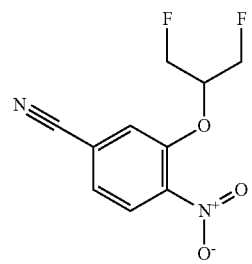 [SMILES: N#Cc1ccc([N+](=O)[O-])c(OC(CF)CF)c1]

1,3-Difluoro-propan-2-ol (4.2 g) was dissolved under argon in THF (250 ml) and cooled to 0° C. LiHMDS (28 ml) was added to the mixture and stirred at rt for 1 hour. Then the mixture was cooled to 0° C. and 3-fluoro-4-nitrobenzonitrile (1.95 ml) was added in portions and stirred for 2 hours. The mixture was poured in water and extracted with DCM. The organic layer was washed with water, dried and concentrated.
Yield: 4.9 g XIX.2 4-Amino-3-(2-fluoro-1-fluoromethyl-ethoxy)-benzonitrile

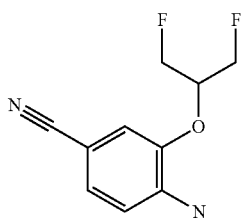 [SMILES: N#Cc1ccc(N)c(OC(CF)CF)c1]

3-(2-Fluoro-1-fluoromethyl-ethoxy)-4-nitro-benzonitrile (1.45 g), tin(II) chloride dihydrate (4.00 g) and ethanol (60 ml) were stirred at 100° C. for 2 hours. The mixture was poured in water and extracted with DCM. The organic layer was washed with water, dried and concentrated.
Yield: 1.04 g Intermediate XXIV 4-Chloro-5-methyl-thieno[2,3-d]pyrimidine-6-carboxylic acid amide

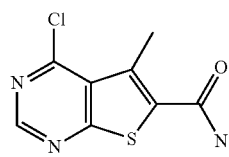

XXIV.1
5-Amino-4-cyano-3-methyl-thiophene-2-carboxylic acid methyl ester

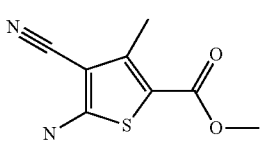

To a mixture of methylacetoacetate (80.9 ml), malononitrile (49.5 g), sulfur (24 g) in methanol (750 ml) was added morpholin (139.4 ml). The mixture was stirred at rt for 10 min. Then the mixture was stirred at reflux for 3.5 hours. After that time the mixture was cooled with an ice bath and filtrated. The solid was washed with methanol and oven dried at 60° C.
Yield: 88.2 g
ESI mass spectrum: m/z=197 (M+H)$^+$ XXIV.2 5-Methyl-4-oxo-3,4-dihydro-thieno[2,3-d]pyrimidine-6-carboxylic acid methyl ester

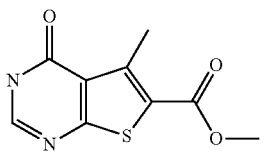

To the product from XXIV.1 (70 g) was added formic acid (875 ml) and the mixture was stirred at reflux overnight. The mixture was cooled down, poured in ice water and filtrated. The solid was washed with water and a small portion of methanol. Then the residue was triturated with diethylether.
Yield: 72.98 g
ESI mass spectrum: m/z=225 (M+H)$^+$ XXIV.3 5-Methyl-4-oxo-3,4-dihydro-thieno[2,3-d]pyrimidine-6-carboxylic acid

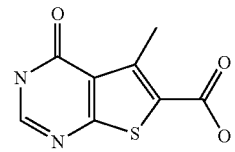

The product from XXIV.2 (1 g), sodium hydroxide 4M (5 ml) and methanol were stirred at reflux for 1 hour. At rt 5 ml hydrochloric acid 4M were added and the mixture was filtrated. The solid was washed with water and dried at 60° C. in an oven overnight.
Yield: 950 mg
ESI mass spectrum: m/z=211 (M+H)$^+$ XXIV.4 4-Chloro-5-methyl-thieno[2,3-c]pyrimidine-6-carbonyl chloride

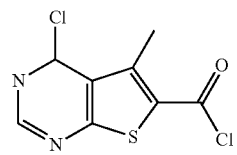

DMF (0.2 ml) was added to a mixture of the product from XXIV.3 (1 g) and thionylchloride (10 ml). The mixture was stirred at reflux for 1 hour. Then the mixture was concentrated.
Yield: 1.2 g XXIV.5 4-Chloro-5-methyl-thieno[2,3-d]pyrimidine-6-carboxylic acid amide

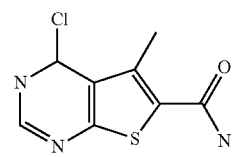

The product from XXIV.4 (1 g) was dissolved warm in ACN (10 ml). This mixture was added dropwise to an ice cooled solution of concentrated ammonia (20 ml) and stirred for 15 min. The mixture was filtrated. The solid was washed with water and oven dried at 50° C.
Yield: 677 mg
ESI mass spectrum: m/z=226 (M+H)$^+$
Retention time HPLC: 0.766 min
HPLC method: M2-SB-C18

Intermediate XXVI

3-(2-Amino-5-fluoro-phenoxy)-2-methyl-butan-2-ol

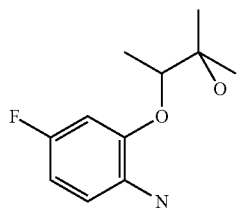

XXVI.1 2-Methyl-butane-2,3-diol

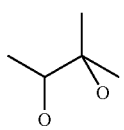

3-Hydroxy-3-methyl-2-butanon (5 ml) was dissolved in ethanol (20 ml). PtO2 (100 mg) was added and the mixture was hydrogenated at room temperature for 4 h and 3 bar. The mixture was concentrated in vacuo.
Yield: 3.87 g

XXVI.2 3-(5-Fluoro-2-nitro-phenoxy)-2-methyl-butan-2-ol

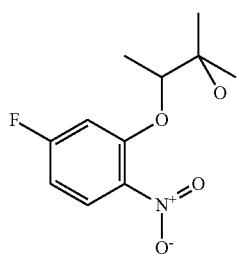 [SMILES: CC(Oc1cc(F)ccc1[N+](=O)[O-])C(C)(C)O]

Prepared analogously to example XX.2 using the product from XXVI.1 (0.9 ml).
Yield: 1.7 g
ESI mass spectrum: m/z=261 (M+H)$^+$
Retention time HPLC: 1.185 min
HPLC method: M2-SB-C18

XXVI.3 3-(2-Amino-5-fluoro-phenoxy)-2-methyl-butan-2-ol

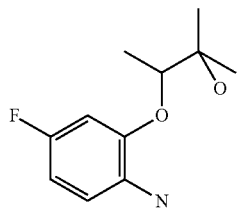

Prepared analogously to example XI.2 using the product from XXVI.2 (1.7 g).
Yield: 1.45 g
ESI mass spectrum: m/z=214 (M+H)$^+$
Retention time HPLC: 0.681 min
HPLC method: M2-SB-C18

Compound 1 tert-Butyl 2-(5-fluoro-2-(5-methyl-6-(methylcarbamoyl)thieno[2,3-d]pyrimidin-4-ylamino)phenoxy)propylcarbamate

1.1 Methyl 4-(2-(1-tert-butoxycarbonylamino)propan-2-yloxy)-4-fluorophenylamino)-5-methyl-thieno[2,3-d]pyrimidine-6-carboxylate

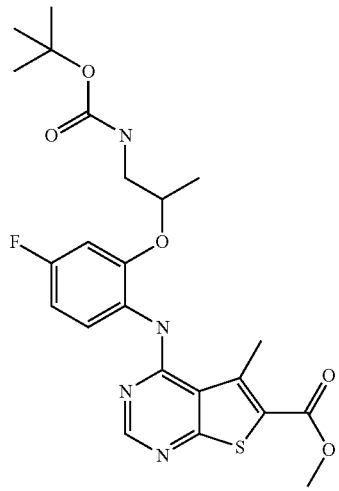 [SMILES: COC(=O)c1sc2ncnc(Nc3ccc(F)cc3OC(C)CNC(=O)OC(C)(C)C)c2c1C]

4-Chloro-5-methyl-thieno[2,3-d]pyrimidine-6-carboxylic acid methyl ester (2.0 g), tert-butyl 2-(2-amino-5-fluorophenoxy)propylcarbamate (2.3 g) and Hünig's base (4.2 ml) were dissolved in dioxane (70 ml). The reaction mixture was heated at 100° C. for three days. Then the reaction was cooled and the precipitate was filtered, washed with dioxane, water and diethylether.
Yield: 1.4 g
ESI mass spectrum: m/z=491 (M+H)$^+$
Retention time HPLC: 3.36 min
HPLC method: A_4

1.2 4-(2-(1-(tert-Butoxycarbonylamino)propan-2-yloxy)-4-fluorophenylamino)-5-methyl-thieno[2,3-d]pyrimidine-6-carboxylic acid

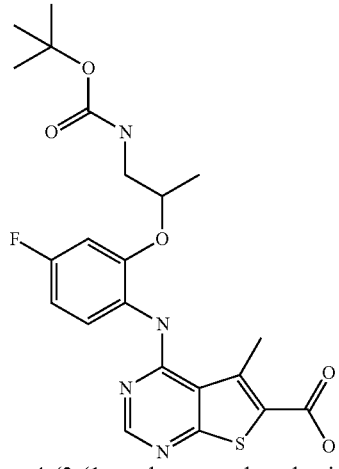

Methyl 4-(2-(1-tert-butoxycarbonylamino)propan-2-yloxy)-4-fluorophenylamino)-5-methylthieno[2,3-d]pyrimidine-6-carboxylate (700 mg) and NaOH (1M; 3.6 ml) was dissolved in a mixture of methanol and THF (1:1; 20 ml). The reaction was stirred at room temperature overnight. Aqueous HCl (1M; 3.6 ml) was added and the organic solvent was evaporated. The residue was triturated with water and filtered. The residue was washed with water, methanol and Et$_2$O and dried at 60° C.
Yield: 0.63 g
ESI mass spectrum: m/z=477 (M+H)$^+$
Retention time HPLC: 1.96 min
HPLC method: A_9

1.3 tert-Butyl 2-(5-fluoro-2-(5-methyl-6-(methylcarbamoyl)thieno[2,3-d]pyrimidin-4-ylamino)phenoxy)propylcarbamate

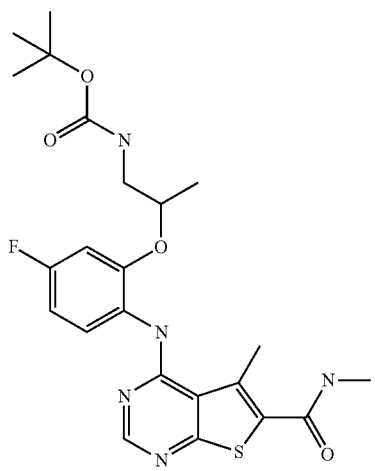 [SMILES: CNC(=O)c1sc2ncnc(Nc3ccc(F)cc3OC(C)CNC(=O)OC(C)(C)C)c2c1C]

To a solution of 4-(2-(1-(tert-Butoxycarbonylamino)propan-2-yloxy)-4-fluorophenylamino)-5-methylthieno[2,3-d]pyrimidine-6-carboxylic acid (80 mg) in DMF (1 ml), TBTU (54 mg) and triethylamine (60 μl) were added. The mixture was stirred at room temperature for 5 min then methylamine in THF (2M; 420 μl) was added and the reaction stirred at room temperature overnight. The mixture was diluted with methanol and purified directly by RP-chromatography (water with 0.2% trifluoroacetic acid/methanol 72-100%) to give the title compound.

Yield: 38 mg

ESI mass spectrum: m/z=490 (M+H)$^+$

Retention time HPLC: 1.86 min

HPLC method: A_9

Further Analogues of 1:

The compounds listed in table 1 were synthesized analogously to example 1.3 using 4-(2-(1-(tert-butoxycarbonylamino)propan-2-yloxy)-4-fluorophenylamino)-5-methylthieno[2,3-d]pyrimidine-6-carboxylic acid and the corresponding amine.

TABLE 1

| | Structure | Name | Yield | Mass | Retention time | HPLC method |
|---|---|---|---|---|---|---|
| 1.4 | 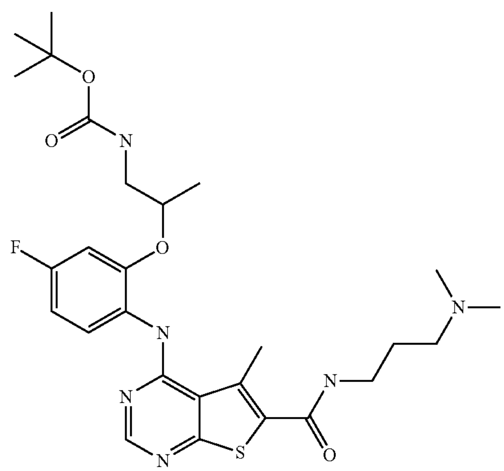 [SMILES: Cc1c(C(=O)NCCCN(C)C)sc2ncnc(Nc3ccc(F)cc3OC(C)CNC(=O)OC(C)(C)C)c12] | tert-Butyl 2-(2-(6-(3-(dimethymino)propylcarbamoyl)-5-methyl-thieno[2,3-d]pyrimidin-4-ylamino)-5-fluorophenoxy)propylcarbamate | 35 mg | 561 | 1.41 | A_9 |
| 1.5 | 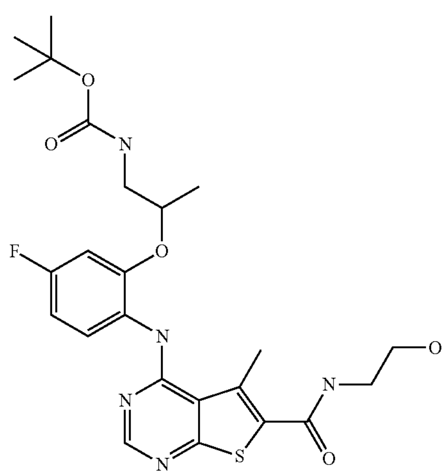 [SMILES: Cc1c(C(=O)NCCO)sc2ncnc(Nc3ccc(F)cc3OC(C)CNC(=O)OC(C)(C)C)c12] | tert-Butyl 2-(5-fluoro-2-(6-(2-hydroxyethylcarbamoyl)-5-methylthieno[2,3-d]-pyrimidin-4-yl-amino)-phenoxy)propylcarbamate | 35 mg | 520 | 1.74 | A_9 |

Compound 2

2.1 Methyl 4-(2-(1-aminopropan-2-yloxy)-4-fluorophenylamino)-5-methyl-thieno[2,3-d]pyrimidine-6-carboxylate trifluoroacetate

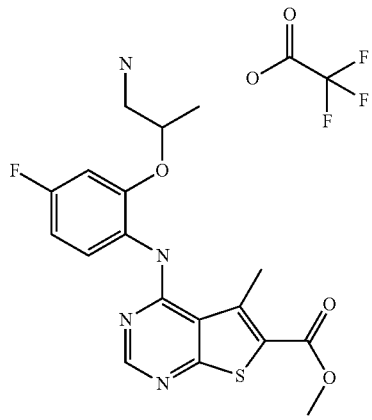 [SMILES: COC(=O)c1sc2ncnc(Nc3ccc(F)cc3OC(C)CN)c2c1C ; O=C(O)C(F)(F)F]

Methyl 4-(2-(1-tert-butoxycarbonylamino)propan-2-yloxy)-4-fluorophenylamino)-5-methyl-thieno[2,3-d]pyrimidine-6-carboxylate (500 mg) was dissolved in a solution of 25% trifluoracetic acid in dichloromethane (10 ml). The reaction mixture was stirred at room temperature for 2 h and then concentrated in vacuo.

Yield: 460 mg

ESI mass spectrum: m/z=391 (M+H)$^+$

Retention time HPLC: 1.31 min

HPLC method: A_9

Further Analogues of 2:

The compounds listed in table 2 were synthesized analogously to example 2.1 using the corresponding BOC protected derivatives shown in Table 1.

TABLE 2

| | Structure | Name | Yield | Mass | Retention time | HPLC method |
|---|---|---|---|---|---|---|
| 2.2 | 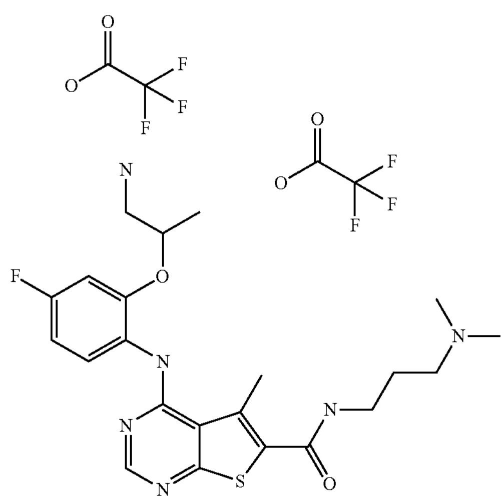 | 4-(2-(1-Amino-propan-2-yloxy)-4-fluorophenylamino)-N-(3-(diemthyl-amino)propyl)-5-methylthieno[2,3-d]pyrimidine-6-carboxamide bis(trifloroacetate) | 35 mg | 461 | 1.03 | A_9 |
| 2.3 | 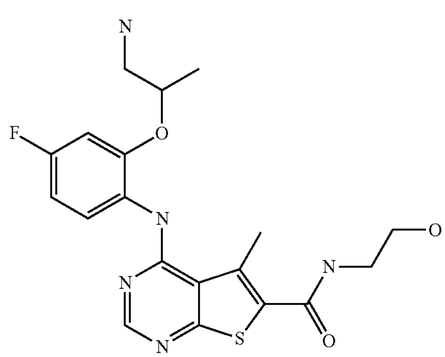 [SMILES: Cc1c(C(=O)NCCO)sc2ncnc(Nc3ccc(F)cc3OC(C)CN)c12] | 4-(2-(1-Amino-propan-2-yloxy)-4-fluorophenylamino)-N-(2-hydroxy-ethyl)-5-methyl-thieno[2,3-d]-pyrimidine-6-carboxamide | 13 mg | 420 | 1.16 | A_9 |

TABLE 2-continued

| | Structure | Name | Yield | Mass | Retention time | HPLC method |
|---|---|---|---|---|---|---|
| 2.4 | 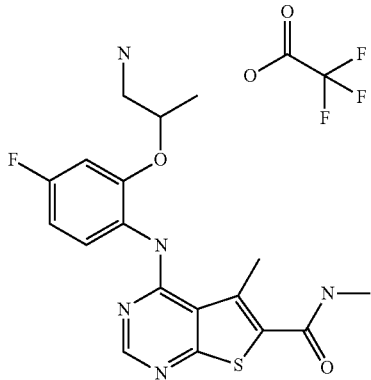 | 4-(2-(1-Amino-propan-2-yloxy)-4-fluorophenylamino)-N-5-methyl-thieno[2,3-d]-pyrimidin-6-carboxamide trifluoroacetate | 24 mg | 390 | 1.16 | A_9 |

Compound 3
Methyl 4-(4-fluoro-2-(1-(methylsulfonamido)propan-2-yloxy)phenylamino)-5-methyl-thieno[2,3-d]pyrimidine-6-carboxylate 3.1 Methyl 4-(4-fluoro-(2-(1-methylsulfonamido)propan-2-yloxy)phenylamino)-5-methyl-thieno[2,3-d]pyrimidine-6-carboxylate

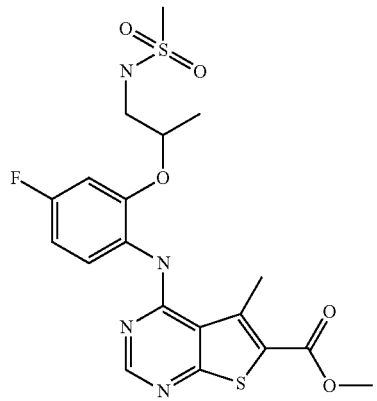 [SMILES: COC(=O)c1sc2ncnc(Nc3ccc(F)cc3OC(C)CNS(C)(=O)=O)c2c1C]

To a solution of Methyl 4-(2-(1-aminopropan-2-yloxy)-4-fluorophenylamino)-5-methyl-thieno[2,3-d]pyrimidine 6-carboxylate trifluoroacetate (80 mg) and triethylamine (55 µl) in dichloromethane (1.5 ml), methansulfonyl chloride (16 µl) was added. The reaction mixture was stirred at room temperature overnight. Then the reaction was quenched with water and methanol. The organic layer was separated and concentrated in vacuo.

Yield: 68 mg

ESI mass spectrum: m/z=469 (M+H)$^+$

Retention time HPLC: 1.99 min

HPLC method: A_9

Further Analogues of Compound 3:

The compounds listed in table 3 were synthesized analogously to example 3.1 using the appropriate amine and the corresponding chloride.

TABLE 3

| | Structure | Name | Yield | Mass | Retention time | HPLC method | Chloride |
|---|---|---|---|---|---|---|---|
| 3.2 | 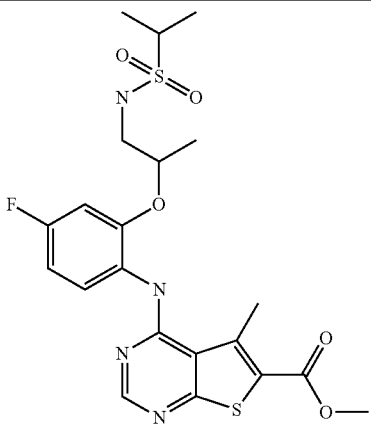 | Methyl 4-(4-fluoro-2-(1-(1-methylethylsulfon-amino)propan-2yloxy)-phenylamino)-5-methyl-thieno[2,3-d]pyrimidine-6-carboxylate | 28 mg | 497 | 1.99 | A_9 | 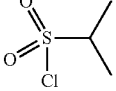 |

TABLE 3-continued

| | Structure | Name | Yield | Mass | Retention time | HPLC method | Chloride |
|---|---|---|---|---|---|---|---|
| 3.3 | 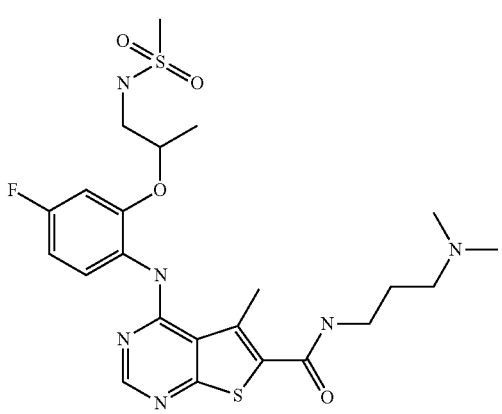 [SMILES: Cc1c(C(=O)NCCCN(C)C)sc2ncnc(Nc3ccc(F)cc3OC(C)CNS(C)(=O)=O)c12] | N-(3-(Dimethylamino)propyl)-4-(4-fluoro-2-(1-methyl-sulfonamido)-propan-2-yloxy)phenyl-amino)-5-methylthieno-[2,3-d]pyrimidine-6-carboxamide | 5.1 mg | 539 | 1.28 | A_9 |  |
| 3.4 | 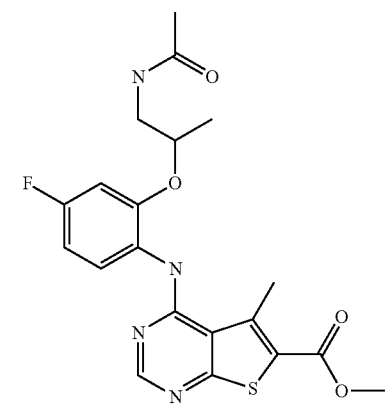 [SMILES: COC(=O)c1sc2ncnc(Nc3ccc(F)cc3OC(C)CNC(C)=O)c2c1C] | Methyl 4-(2-(1-acet-amidopropan-2-yloxy)-4-fluorophenylamino)-5-methylthieno[2,3-d]pyrimidine-6-carboxylate | 64 mg | 433 | 1.82 | A_AL CMS2_9 |  |
| 3.5 | 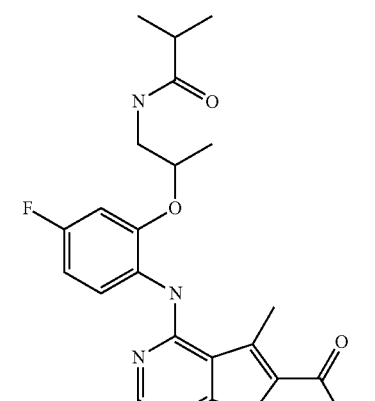 | Methyl 4-(4-fluoro2-(1-isobutyramidopropan-2-yloxy)phenylamino)-5-methylthieno[2,3-d]-pyrimidine-6-carboxylate | 58 mg | 461 | 1.99 | A_AL CMS2_9 |  |

Compound 4

Methyl 4-(2-(1-dimethylamino)propan-2yloxy)-4-fluorophenylamino)-5-methyl-thieno[2,3-d]pyrimidine-6-carboxylate trifluoroacetate

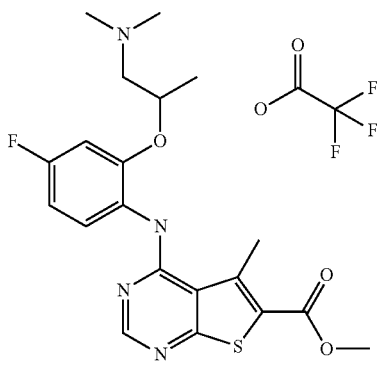 [SMILES: COC(=O)c1sc2ncnc(Nc3ccc(F)cc3OC(C)CN(C)C)c2c1C ; O=C(O)C(F)(F)F]

Methyl 4-(2-(1-aminopropan-2-yloxy)-4-fluorophenylamino)-5-methyl-thieno[2,3-d]pyrimidine-6-carboxylate trifluoroacetate (100 mg) was dissolved in THF (2.5 ml), NaOH (4M; 55 μl) and formaldehyde 37% in water (55 μl) was added. The reaction mixture was stirred a few minutes. Then sodium triacetoxyborohydride (220 mg) was added and the reaction was stirred at room temperature for 4 h. Then the mixture was concentrated in vacuo. The residue was dissolved in dichloromethane and washed with aqueous NaOH (1M). The organic layer was separated and concentrated in vacuo. The product was purified by RP-chromatography (water with 0.2% trifluoroacetic acid/methanol 72-100%) to afford the title compound.

Yield: 83 mg
ESI mass spectrum: m/z=419 (M+H)$^+$
Retention time HPLC: 1.32 min
HPLC method: A_9

Compound 5 tert-Butyl 2-(2-(6-carbamoyl-5-methyl-thieno[2,3-d]pyrimidin-4-ylamino)-5-fluorophenoxy)propylcarbamate

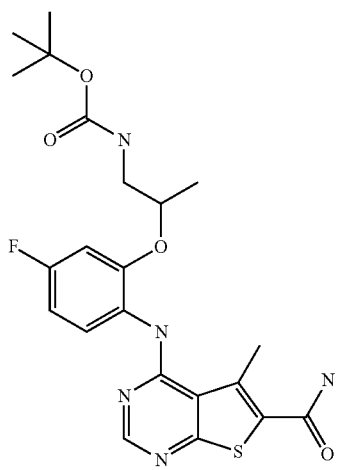 [SMILES: Cc1c(C(N)=O)sc2ncnc(Nc3ccc(F)cc3OC(C)CNC(=O)OC(C)(C)C)c12]

4-(2-(1-(tert-Butoxycarbonylamino)propan-2-yloxy)-4-fluorophenylamino)-5-methyl-thieno[2,3-d]pyrimidine-6-carboxylic acid (250 mg) and TBTU (170 mg) was dissolved in DMF (3 ml) and triethylamine (1900) was added. The mixture was stirred at room temperature for 10 min, then 0.5 ml conc. ammonia was added. The reaction was stirred for 2 h. Then the reaction mixture was concentrated in vacuo and purified by RP-chromatography (water with 0.2% trifluoroacetic acid/methanol 72-100%) to give the title compound.

Yield: 55 mg
ESI mass spectrum: m/z=476 (M+H)$^+$
Retention time HPLC: 1.80 min
HPLC method: A_9

Compound 6

(R) and (S)-4-(2-(1-aminopropan-2-yloxy)-4-fluorophenylamino)-5-methyl-thieno[2,3-d]pyrimidine-6-carboxamide trifluoroacetate 6.1 (R) and (S)-tert-butyl 2-(2-(6-carbamoyl-5-methyl-thieno[2,3-d]pyrimidin-4-ylamino)-5-fluorophenoxy)propylcarbamate

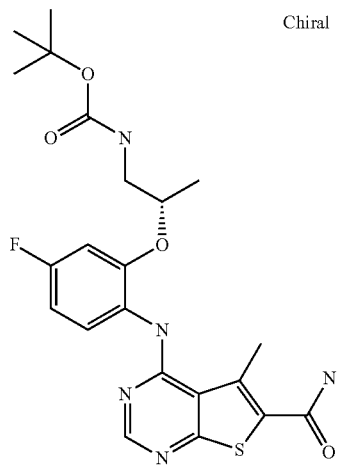 [SMILES: Cc1c(C(N)=O)sc2ncnc(Nc3ccc(F)cc3O[C@@H](C)CNC(=O)OC(C)(C)C)c12]

The racemate of example 5 was separated by means of HPLC to afford the two enantiomers. The configuration was assigned arbitrarily.

Enantiomer A:
Yield: 10 mg
ESI mass spectrum: m/z=476 (M+H)$^+$
Retention time HPLC: 1.80 min
HPLC method: A_9

Enantiomer B:
Yield: 14.2 mg
ESI mass spectrum: m/z=476 (M+H)$^+$
Retention time HPLC: 1.80 min
HPLC method: A_9

6.2 (R) and (S)-4-(2-(1-aminopropan-2-yloxy)-4-fluorophenylamino)-5-methylthieno[2,3-d]pyrimidine-6-carboxamide trifluoroacetate

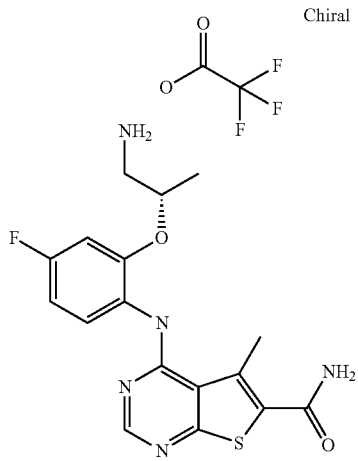 [SMILES: O=C(O)C(F)(F)F ; Cc1c(C(N)=O)sc2ncnc(Nc3ccc(F)cc3O[C@@H](C)CN)c12]

Prepared analogously to example 2.1 from (S)-tert-butyl 2-(2-(6-carbamoyl-5-methylthieno[2,3-d]pyrimidin-4-ylamino)-5-fluorophenoxy)propylcarbamate and the enantiomer, respectively.

The configuration was assigned arbitrarily.
Enantiomer A
Yield: 7 mg
ESI mass spectrum: m/z=376 (M+H)$^+$
Retention time HPLC: 1.16 min
HPLC method: A__9
Enantiomer B
Yield: 11 mg
ESI mass spectrum: m/z=376 (M+H)$^+$
Retention time HPLC: 1.16 min
HPLC method: A__9

Compound 7

4-(2-(1-Aminopropan-2-yloxy)-4-fluorophenylamino)-5-methyl-thieno[2,3-d]pyrimidine-6-carboxylic acid trifluoroacetate

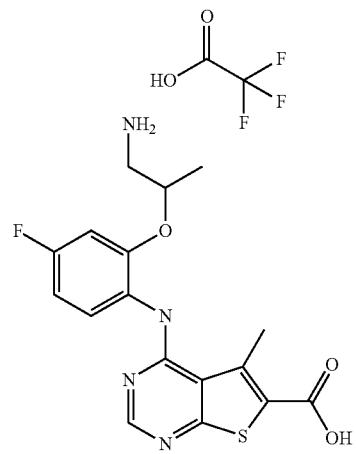 [SMILES: O=C(O)C(F)(F)F ; Cc1c(C(=O)O)sc2ncnc(Nc3ccc(F)cc3OC(C)CN)c12]

Synthesized analogously to example 2-1 from 4-(2-(1-(tert-butoxycarbonyl-amino)propan-2-yloxy)-4-fluorophenylamino)-5-methyl-thieno[2,3-d]pyrimidine-6-carboxylic acid Yield: 89 mg
ESI mass spectrum: m/z=377 (M+H)$^+$
Retention time HPLC: 1.26 min
HPLC method: A__9

Compound 8

4-(4-Fluoro-2-(1-(3,3,3-trifluoropropylamino)propan-2-yloxy)phenylamino-5-methyl-thieno[2,3-d]pyrimidine-6-carboxamide

8.1 4-(2-(1-Aminopropan-2-yloxy)-4-fluorophenylamino)-5-methyl-thieno[2,3-d]pyrimidine-6-carboxamide trifluoroacetate

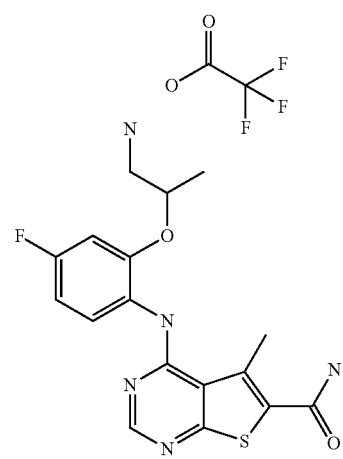 [SMILES: O=C(O)C(F)(F)F ; Cc1c(C(N)=O)sc2ncnc(Nc3ccc(F)cc3OC(C)CN)c12]

tert-Butyl 2-(2-(6-carbamoyl-5-methylthieno[2,3-d]pyrimidin-4-ylamino)-5-fluorophenoxy)propylcarbamate (740 mg) was dissolved in dichloromethane (20 ml) and trifluoroacetic acid (4 ml) was added and the reaction was stirred at room temperature overnight. The reaction was concentrated in vacuo to give the title compound.
Yield: 667 mg
ESI mass spectrum: m/z=376 (M+H)$^+$

8.2 4-(4-Fluoro-2-(1-(3,3,3-trifluoropropylamino)propan-2-yloxy)phenylamino-5-methyl-thienor[2,3-d]pyrimidine-6-carboxamide

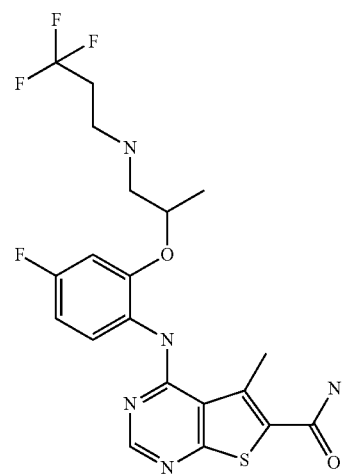 [SMILES: Cc1c(C(N)=O)sc2ncnc(Nc3ccc(F)cc3OC(C)CNCCC(F)(F)F)c12]

4-(2-(1-Aminopropan-2-yloxy)-4-fluorophenylamino)-5-methyl-thieno[2,3-d]pyrimidine-6-carboxamide 2,2,2-trifluoroacetate (200 mg) was dissolved in THF (20 ml) and buffer pH 5 (2 ml), 3,3,3,-trifluoropropanal (50.4 mg) and sodium cyanoborohydride (30.8 mg) were added.

The reacion was stirred at room temperature for 4 days. The residue was diluted with 10 ml water, then the organic solvent was evaporated. The residual aqueous fraction was extracted with ethylacetate. The organic layer was separated, dried and concentrated in vacuo.

Yield: 190 mg

ESI mass spectrum: m/z=472 (M+H)+

Retention time HPLC: 1.38 min

HPLC method: A_10

Compound 9

Methyl 4-(2-(2-aminoethoxy)-4-fluorophenylamino)-5-methyl-thieno[2,3-d]pyrimidine-6-carboxylate hydrochloride 9.1 Methyl 4-(2-(2-(tert-butoxycarbonylamino)ethoxy)-4-fluorophenylamino)-5-methyl-thieno[2,3-d]pyrimidine-6-carboxylate

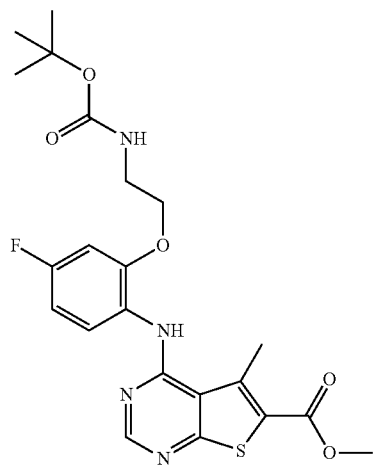 [SMILES: COC(=O)c1sc2ncnc(Nc3ccc(F)cc3OCCNC(=O)OC(C)(C)C)c2c1C]

Methyl 4-(4-fluoro-2-hydroxyphenylamino)-5-methyl-thieno[2,3-d]pyrimidine-6-carboxylate (80.0 mg), Boc-amino-ethanol (50.0 mg) and polymer-bound triphenylphosphine (240.0 mg) was suspended in THF (3.0 ml). The mixture was stirred at room temperature for 5 min. Then di-tert-butyl azodicarboxylate (165.0 mg) was added and the mixture stirred at room temperature overnight. To this reaction celite was added, the resulting mixture was filtered through celite and the filtrate was concentrated in vacuo. The residue was purified by RP-chromatography (water with 0.2% trifluoroacetic acid/methanol 59-100%)

Yield: 25.0 mg

ESI mass spectrum: m/z=477 (M+H)+

Retention time HPLC: 2.12 min

HPLC method: A_9

9.2 Methyl 4-(2-(2-aminoethoxy)-4-fluorophenylamino)-5-methyl-thieno[2,3-d]pyrimidine-6-carboxylate hydrochloride

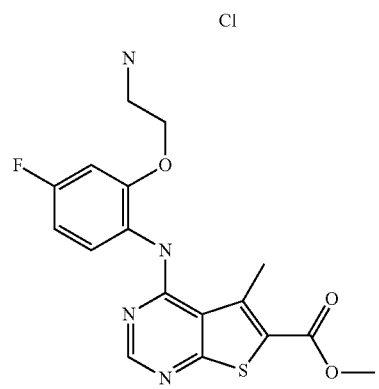 [SMILES: Cl ; COC(=O)c1sc2ncnc(Nc3ccc(F)cc3OCCN)c2c1C]

Methyl 4-(2-(2-(tert-butoxycarbonylamino)ethoxy)-4-fluorophenylamino)-5-methyl-thieno[2,3-d]pyrimidine-6-carboxylate (20 mg) was dissolved in 25% solution of trifluoroacetic acid in dichlormethane (2 ml). The reaction was stirred at room temperature for 2 h. The solvent was concentrated in vacuo and the residue was dissolved in methanol and triturated with HCl in methanol.

Yield: 15 mg

ESI mass spectrum: m/z=377 (M+H)+

Retention time HPLC: 1.28 min

HPLC method: A_9

Compound 10

Methyl 4-(2-(1-aminobutan-2yloxy)-4-fluorophenylamino)-5-methyl-thieno[2,3-d]pyrimidine-6-carboxylate hydrochloride 10.1 Methyl 4-(2-(1-(tert-butoxycarbonylamino)butan-2yloxy)-4-fluorophenylamino)-5-methyl-thieno[2,3-d]pyrimidine-6-carboxylate

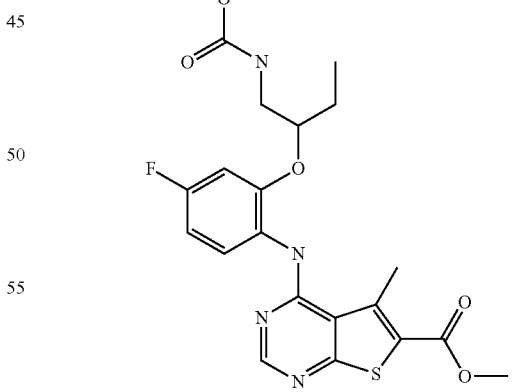

Synthesized analogously to example 9.1 using methyl 4-(4-fluoro-2-hydroxyphenylamino)-5-methylthieno[2,3-d]pyrimidine-6-carboxylate and tert-butyl 2-hydroxybutylcarbamate.

Yield: 36 mg

ESI mass spectrum: m/z=505 (M+H)+

Retention time HPLC: 2.24 min

HPLC method: A_9

10.2 Methyl 4-(2-(1-aminobutan-2yloxy)-4-fluorophenylamino)-5-methyl-thieno[2,3-d]pyrimidine-6-carboxylate hydrochloride

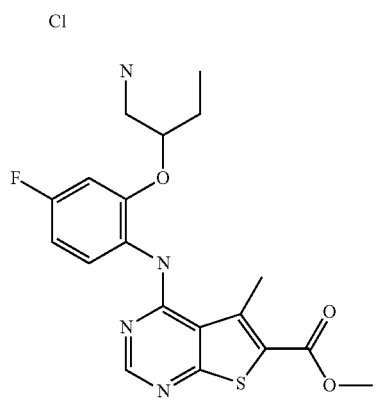 [SMILES: Cl ; CCC(CN)Oc1cc(F)ccc1Nc1ncnc2sc(C(=O)OC)c(C)c12]

Synthesized analogously to example 9.2 using methyl 4-(2-(1-(tert-butoxycarbonylamino)butan-2yloxy)-4-fluorophenylamino)-5-methylthieno[2,3-d]pyrimidine-6-carboxylate
Yield: 21 mg
ESI mass spectrum: m/z=405 (M+H)$^+$
Retention time HPLC: 1.38 min
HPLC method: A_9

Compound 11

Methyl 4-(2-(1-aminopropan-2yloxy)-pyridin-3-ylamino)-5-methyl-thieno[2,3-d]pyrimidine-6-carboxylate hydrochloride 11.1 Methyl 4-(2-(1-(tert-butoxycarbonylamino)propan-2-yloxy)pyridin-3-ylamino)-5-methyl-thieno[2,3-d]pyrimidine-6-carboxylate

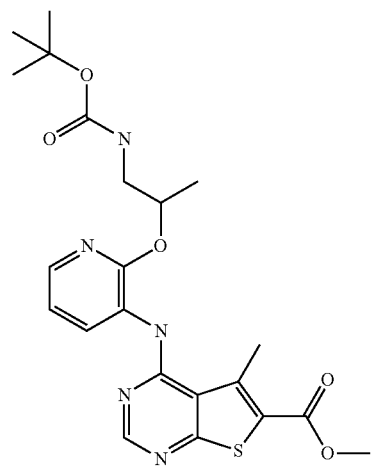 [SMILES: COC(=O)c1sc2ncnc(Nc3cccnc3OC(C)CNC(=O)OC(C)(C)C)c2c1C]

Prepared analogously to example 9.1 using methyl 4-(2-hydroxypyridin-3-ylamino)-5-methylthieno[2,3-d]pyrimidine-6-carboxylate and tert-butyl N-(2-hydroxypropyl)-carbamate.
Yield: 65 mg
ESI mass spectrum: m/z=474 (M+H)$^+$
Retention time HPLC: 1.97 min
HPLC method: A_9

11.2 Methyl 4-(2-(1-aminopropan-2yloxy)-pyridin-3-ylamino)-5-methyl-thieno[2,3-d]pyrimidine-6-carboxylate hydrochloride

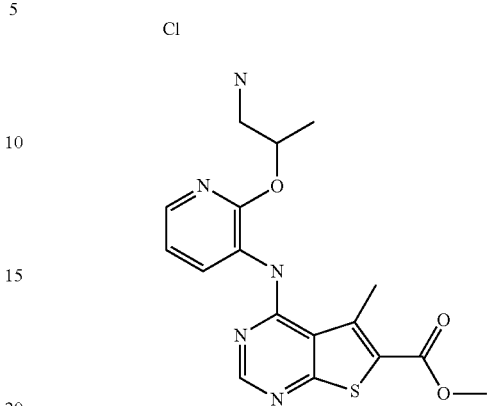

Prepared analogously to example 9.2 using methyl 4-(2-(1-(tert-butoxycarbonyl-amino)-propan-2-yloxy)pyridin-3-ylamino)-5-methylthieno[2,3-d]pyrimidine-6-carboxylate
Yield: 14 mg
ESI mass spectrum: m/z=374 (M+H)$^+$
Retention time HPLC: 1.29 min
HPLC method: A_9

Compound 12

Methyl 4-(2-(4-aminobutan-2yloxy)-4-fluorophenylamino)-5-methyl-thieno[2,3-d]pyrimidine-6-carboxylate hydrochloride

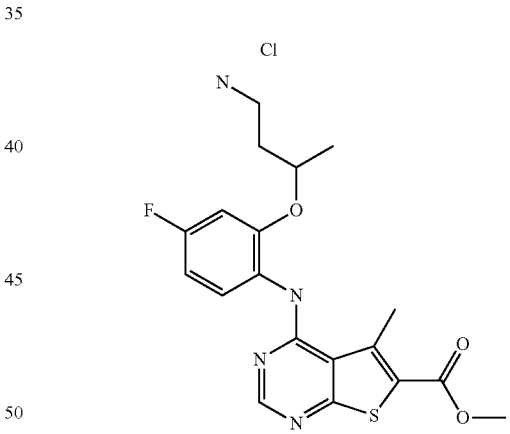

4-Chloro-5-methyl-thieno[2,3-d]pyrimidine-6-carboxylic acid methyl ester (1.25 g), tert-butyl 3-(2-amino-5-fluorophenoxy)butylcarbamate (1.7 g) and p-toloulsulfonic acid (175 mg) was dissolved in dioxane (30 ml) and the solution was heated under reflux overnight. Then the reaction mixture was concentrated in vacuo. The residue was treated with trifluoracetic acid 25% in dichloromethane and stirred at room temperature for 1 h. The solution was concentrated in vacuo and the residue was dissolved in dichloromethane and washed with sodium bicarbonate. The organic phase was separated, dried and concentrated in vacuo. The residue was triturated with Et$_2$O and the precipitate was filtered.
Yield: 2.14 g
ESI mass spectrum: m/z=405 (M+H)$^+$
Retention time HPLC: 1.36 min
HPLC method: A_9

Compound 13

Methyl 4-(4-fluoro-2-(4-(methylsulfonamido)butan-2yloxy)phenylamino)-5-methyl-thieno[2,3-d]pyrimidine-6-carboxylate

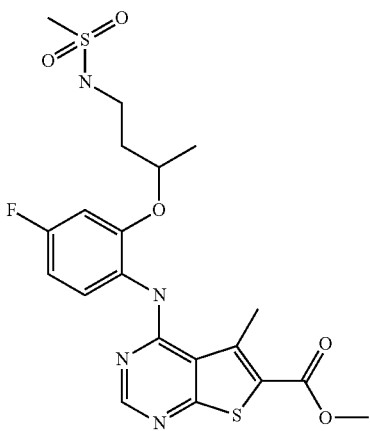 [SMILES: COC(=O)c1sc2ncnc(Nc3ccc(F)cc3OC(C)CCNS(C)(=O)=O)c2c1C]

Methyl 4-(2-(4-aminobutan-2yloxy)-4-fluorophenylamino)-5-methyl-thieno[2,3-d]pyrimidine-6-carboxylate hydrochloride (80 mg) and triethylamine (65 µl) were dissolved in dichloromethane (1.5 ml) and methansulfonyl chloride (18 µl) was added. The reaction mixture was stirred at room temperature overnight. Then the mixture was diluted with water and some methanol. The organic layer was separated and concentrated in vacuo. The residue was purified by RP-chromatography (water with 0.2% trifluoroacetic acid/methanol 59-100%)

Yield: 33 mg

ESI mass spectrum: m/z=483 (M+H)$^+$

Retention time HPLC: 1.94 min

HPLC method: A_9

Further Analogues of Compound 13:

The compounds listed in table 4 were synthesized analogously to example 13 using the appropriate amine and the corresponding chlorides or isocyanate.

| | Structure | Name | Yield | Mass | Retention time | HPLC method | Chloride/Isocyanats |
|---|---|---|---|---|---|---|---|
| 13.2 | 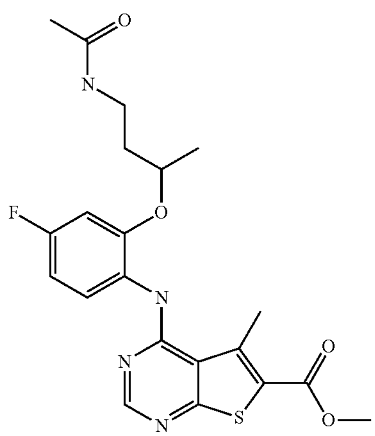 [SMILES: COC(=O)c1sc2ncnc(Nc3ccc(F)cc3OC(C)CCNC(C)=O)c2c1C] | Methyl 4-(2-(4-acetamidobutan-2-yloxy)-4-fluorophenylamino)-5-methyl-thieno[2,3-d]pyrimidine-6-carboxylate | 11 mg | 447 | 1.86 | A_9 | |
| 13.3 | 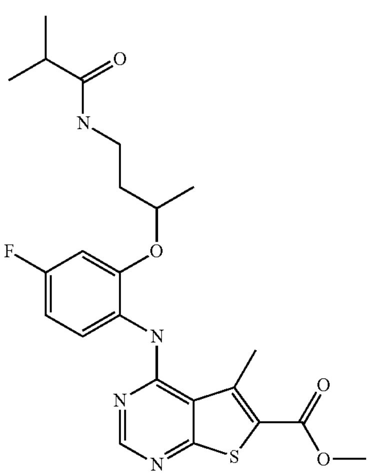 [SMILES: COC(=O)c1sc2ncnc(Nc3ccc(F)cc3OC(C)CCNC(=O)C(C)C)c2c1C] | Methyl 4-(4-fluoro-2-(4-isobutyramidobutan-2-yloxy)-phenylamino)-5-methylthieno[2,3-d]pyrimidine-6-carboxylate | 26 mg | 475 | 2.0 | A_9 | |

-continued

| | Structure | Name | Yield | Mass | Retention time | HPLC method | Chloride/ Isocyanats |
|---|---|---|---|---|---|---|---|
| 13.4 | 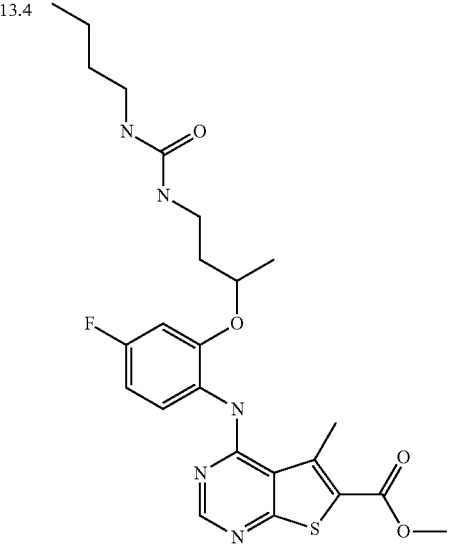 | Methyl 4-(2-(4-(3-butylureido)-butan-2-yloxy)-4-fluorophenyl-amino)-5-methylthieno[2,3-d]pyrimidine-6-carboxylate | 57 mg | 504 | 2.05 | A_9 | 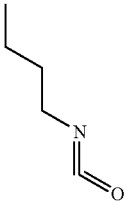 |

Compound 14

Methyl 4-(2-(dimethylamino)butan-2yloxy)-4-fluorophenylamino)-5-methyl-thieno[2,3-d]pyrimidine-6-carboxylate trifluoroacetate

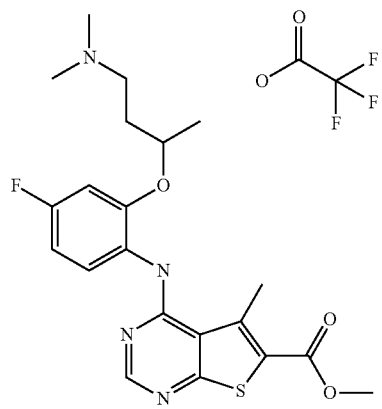 [SMILES: COC(=O)c1sc2ncnc(Nc3ccc(F)cc3OC(C)CCN(C)C)c2c1C ; O=C(O)C(F)(F)F]

Prepared analogously to example 4.1 using methyl 4-(2-(4-aminobutan-2yloxy)-4-fluorophenylamino)-5-methyl-thieno[2,3-d]pyrimidine-6-carboxylate hydrochloride Yield: 53 mg ESI mass spectrum: m/z=433 (M+H)$^+$ Retention time HPLC: 1.38 min HPLC method: A_9

Compound 15

Methyl 4-(2--((4-aminobutan-2yloxy)pyridin-3ylamino)-5-methyl-thieno[2,3-d]pyrimidine-6-carboxylate trifluoracetate 15.1 Methyl 4-(2-((4-tert-butoxycarbonyl)amino)butan-2yloxy)phyridin-3ylamino)-5-methylthieno[2,3-d]pyrimidine-6-carboxylate

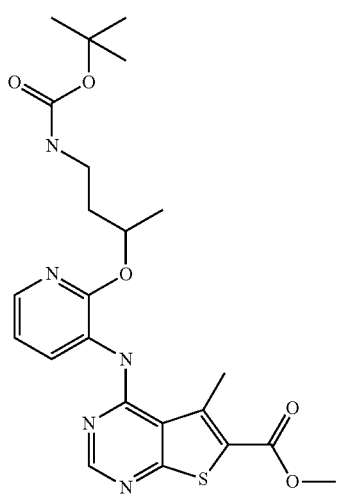 [SMILES: COC(=O)c1sc2ncnc(Nc3cccnc3OC(C)CCNC(=O)OC(C)(C)C)c2c1C]

Prepared analogously to example 1.1 using 4-Chloro-5-methyl-thieno[2,3-d]pyrimidine-6-carboxylic acid methyl ester and tert-butyl 3-(3-aminopyridin-2yloxy)butylcarbamate Yield: 1 g ESI mass spectrum: m/z=488 (M+H)$^+$

15.2 Methyl 4-(2-((4-aminobutan-2yloxy)pyridin-3ylamino)-5-methyl-thieno[2,3-d]pyrimidine-6-carboxylate trifluoroacetate

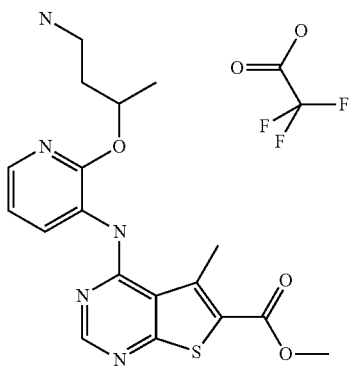 [SMILES: COC(=O)c1sc2ncnc(Nc3cccnc3OC(C)CCN)c2c1C ; O=C(O)C(F)(F)F]

Prepared analogously to example 1.2 from methyl 4-(2-((4aminobutan-2yloxy)pyridin-3ylamino)-5-methylthieno[2,3-d]pyrimidine-6-carboxylate trifluoroacetate
Yield: 100 mg
ESI mass spectrum: m/z=388 (M+H)⁺
Retention time HPLC: 1.26 min
HPLC method: A_10

Compound 16

4-(2-(4-Aminobutan-2yloxy)pyridin-3-ylamino)-N-(3-(dimethylamino)propyl)-5-methylthieno[2,3-d]pyrimidine-6-carboxamide bis-trifluoroacetate

16.1 4-(2-(4-(tert-Butoxycarbonylamino)butan-2yloxy)pyridin-3ylamino)-5-methyl-thieno[2,3-d]pyrimidine-6-carboxylic acid

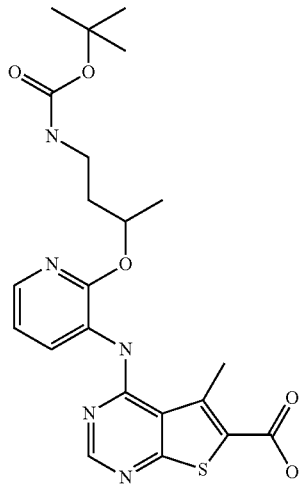 [SMILES: Cc1c(C(=O)O)sc2ncnc(Nc3cccnc3OC(C)CCNC(=O)OC(C)(C)C)c12]

Methyl 4-(2-(4-(tert-butoxycarbonylamino)butan-2yloxy)pyridin-3ylamino)-5-methyl-thieno[2,3-d]pyrimidine-6-carboxylate (600 mg) was dissolved in methanol (10 ml) and NaOH (1M; 2.5 ml) was added. The reaction mixture was heated at reflux for 15 minutes. Then it was cooled to room temperature and HCl (1M; 2.5 ml) was added. Methanol was evaporated and the residue was dissolved in dichloromethane. The mixture was washed with water, the organic layer was dried and concentrated in vacuo. The residue was triturated with Et₂O.
Yield: 390 mg
ESI mass spectrum: m/z=474 (M+H)⁺

16.2 4-(2-(4-aminobutan-2yloxy)pyridin-3ylamino)-5-methylthieno[2,3-d]pyrimidine-carboxylic acid trifluoroacetate

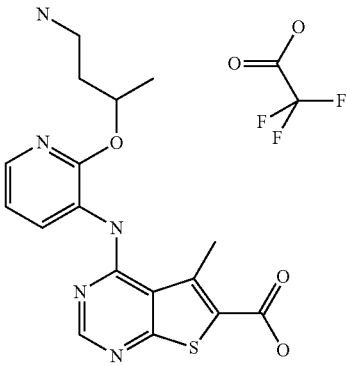 [SMILES: Cc1c(C(=O)O)sc2ncnc(Nc3cccnc3OC(C)CCN)c12 ; O=C(O)C(F)(F)F]

Prepared analogously to example 1.2 from 4-(2-(4-(tert-butoxycarbonylamino)butan-2yloxy)pyridin-3ylamino)-5-methylthieno[2,3-d]pyrimidine-6-carboxylic acid
Yield: 100 mg
ESI mass spectrum: m/z=374 (M+H)⁺
Retention time HPLC: 1.12 min
HPLC method: A_10

16.3 4-(2-(4-Aminobutan-2yloxy)pyridin-3-ylamino)-N-(3-(dimethylamino)propyl)-5-methylthieno[2,3-d]pyrimidine-6-carboxamide bis(2,2,2-trifluoroacetate)

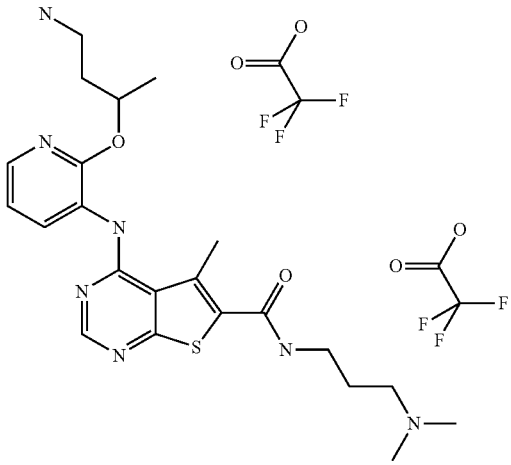 [SMILES: Cc1c(C(=O)NCCCN(C)C)sc2ncnc(Nc3cccnc3OC(C)CCN)c12 ; O=C(O)C(F)(F)F ; O=C(O)C(F)(F)F]

4-(2-(4-(t-Butoxycarbonylamino)butan-2yloxy)pyridin-3ylamino)-5-methylthieno[2,3-d]pyrimidine-6-carboxylic acid (200 mg) and Hünig's base (160 µl) was dissolved in THF (10 ml) and TBTU (148 mg) was added. To this mixture N,N-dimethyl-propandiamine (58 µl) was added and the mixture was stirred at room temperature for three days. The reaction mixture was concentrated in vacuo and the residue was dissolved in dichloromethane. The organic layer was washed with water, dried and 3 ml conc. TFA was added. The mixture was stirred at room temperature for 1 h. The mixture was concentrated in vacuo and the product was purified by RP-chromatography (Method amslpolar 1).
Yield: 190 mg
ESI mass spectrum: m/z=458 (M+H)⁺
Retention time HPLC: 0.86 min
HPLC method: A_10
Compound 16.4:
Prepared analogously to example 16.3 using 4-(2-(4-(tert-butoxycarbonylamino) butan-2yloxy)pyridin-3ylamino)-5-methylthieno[2,3-d]pyrimidine-6-carboxylic acid and ammonia.

| Structure | Name | Yield | Mass | Retention time | HPLC method |
|---|---|---|---|---|---|
| 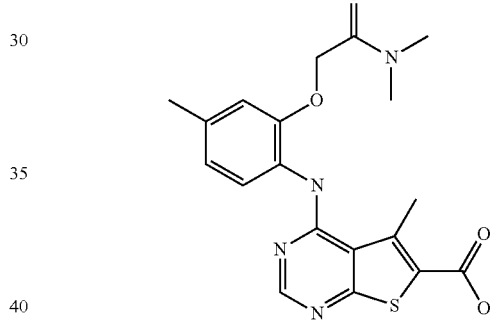 | 4-(2-(4-Aminobutan-2-yloxy)pyridin-3-ylamino)-5-methylthieno-[2,3-d]-pyrimidine-6-carboxamide 2,2,2-trifluoroacetate | 130 mg | 373 | 1.2 | A_10 |

Compound 17

4-(2-(2-(Dimethylamino)-2-oxoethoxy)-4-methylphenylamino)-5-methylthieno[2,3-d]pyrimidine-6-carboxylic acid 17.1 Ethyl 4-(2-(2-dimethylamino)-2-oxoethoxy)-4-methylphenylamino)-5-methyl-thieno[2,3-d]pyrimidine-6-carboxylate

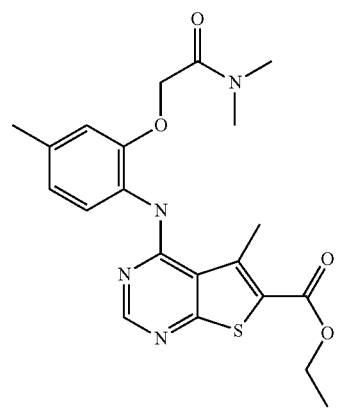 [SMILES: CCOC(=O)c1sc2ncnc(Nc3ccc(C)cc3OCC(=O)N(C)C)c2c1C]

2-(2-Amino-5-methylphenoxy)-N,N-dimethylacetamide (300 mg) and ethyl 4-chloro-5-methyl-thieno[2,3-d]pyrimidine-6-carboxylate (447 mg) were dissolved in dioxane (5 ml) and p-toluenesulfonic acid monohydrate (44 mg) was added. The mixture was heated at 100° C. for 1.5 h. The reaction was allowed to cool to room temperature, the residue was dissolved in dichloromethane and extracted with water. The organic layer was dried and concentrated in vacuo. The residue was purified by chromatography (silica/dichloromethane: methanol 100-95:5).

Yield: 114 mg

ESI mass spectrum: m/z=377 (M+H)$^+$ 17.2 4-(2-(2-(Dimethylamino)-2-oxoethoxy)-4-methylphenylamino)-5-methyl-thieno[2,3-d]pyrimidine-6-carboxlic acid Ethyl 4-(2-(2-dimethylamino)-2-oxoethoxy)-4-methylphenylamino)-5-methyl-thieno[2,3-d]pyrimidine-6-carboxylate (114 mg) was dissolved in methanol (5 ml) and aqueous NaOH (2M; 0.66 ml) was added. The reaction was stirred at room temperature for 4 h. Then the reaction mixture was concentrated in vacuo and neutralisied with aqueous HCl (2M; 5 ml). The precipitate was filtered and the residue was dissolved in DMF and purified by RP-chromatography (water with 0.2% trifluoroacetic acid/methanol 72-100%)

Yield: 26 mg

ESI mass spectrum: m/z=401 (M+H)$^+$

Retention time HPLC: 1.69 min

HPLC method: A_10

Compound 18

Methyl 4-(2-(1,3-diaminopropan-2-yloxy)-4-fluorophenylamino)-5-methylthieno[2,3-d]pyrimidine-6-carboxylate bis(2,2,2-trifluoroacetate)

18.1 4-{2-[2-tert-Butoxycarbonylamino-1-(tert-butoxycarbonylamino-methyl)-ethoxy]-4-fluoro-phenylamino}-5-methyl-thieno[2,3-d]pyrimidine-6-carboxylic acid methyl ester

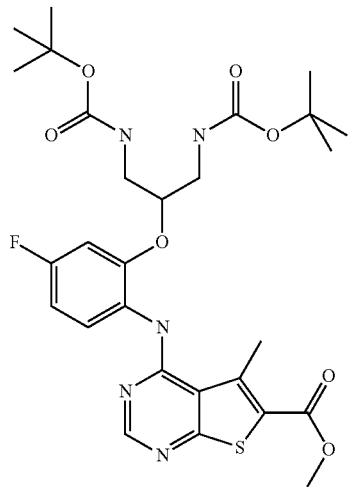 [SMILES: COC(=O)c1sc2ncnc(Nc3ccc(F)cc3OC(CNC(=O)OC(C)(C)C)CNC(=O)OC(C)(C)C)c2c1C]

4-Chloro-5-methyl-thieno[2,3-d]pyrimidine-6-carboxylic acid methyl ester (2 g) and [2-(2-Amino-5-fluoro-phenoxy)-3-tert-butoxycarbonylamino-propyl]-carbamic acid t-butyl (3.3 g) were dissolved in 20 ml isopropanol and 4.3 ml Hünig's base was added. The reaction was heated to 140° C. under microwave irradiation for 45 min. The reaction mixture was allowed to stand over the weekend and the resulting precipitate was filtered. The filter cake was purified by chromatography (silica/dichloromethane: methanol 50:1).

Yield: 2 g
ESI mass spectrum: m/z=606 (M+H)⁺
Retention time HPLC: 2.34 min
HPLC method: A_10

18.2 Methyl 4-(2-(1,3-diaminopropan-2-yloxy)-4-fluorophenylamino)-5-methylthieno[2,3-d]pyrimidine-6-carboxylate bis(trifluoroacetate)

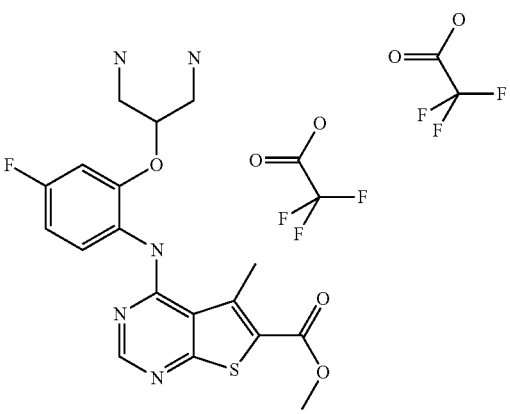

Prepared analogously to example 2.1 using 4-{2-[2-tert-Butoxycarbonylamino-1-(tert-butoxycarbonylamino-methyl)-ethoxy]-4-fluoro-phenylamino}-5-methyl-thieno[2,3-d]pyrimidine-6-carboxylic acid methyl ester Yield: 2 g
ESI mass spectrum: m/z=406 (M+H)⁺
Retention time HPLC: 0.87 min
HPLC method: A_10

Compound 19

Methyl 4-(2-(1-acetamido-3aminopropan-2yloxy)-4-fluorophenylamino)-5-methylthieno[2,3-d]pyrimidine-6-carboxylate (trifluoroacetate)

19.1 Methyl 4-(2-(1-acetamido-3-aminopropan-2-yloxy)-4-fluorophenylamino)-5-methylthieno[2,3-d]pyrimidine-6-carboxylate trifluoroacetate

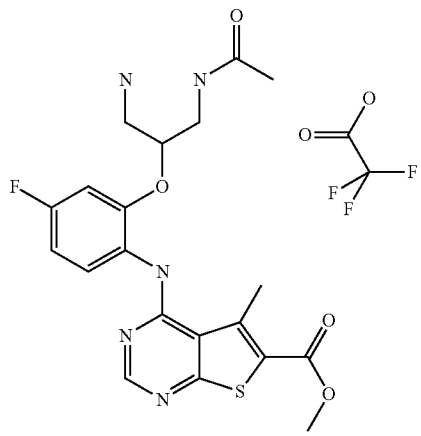 [SMILES: COC(=O)c1sc2ncnc(Nc3ccc(F)cc3OC(CN)CNC(C)=O)c2c1C ; O=C(O)C(F)(F)F]

Methyl 4-(2-(1,3-diaminopropan-2-yloxy)-4-fluorophenylamino)-5-methylthieno[2,3-d]pyrimidine-6-carboxylate bis(trifluoroacetate) (150 mg) and triethylamine (0.1 ml) were dissolved in dichloromethane, acetylchloride (15 μl) was added. The reaction mixture was stirred at room temperature overnight. The reaction was diluted with dichloromethane and methanol and then extracted with aqueous HCl (1M). The organic layer was dried and concentrated in vacuo. The residue was purified by chromatography. The fractions were collected, concentrated in vacuo and triturated with Et₂O.

Yield: 22 mg
ESI mass spectrum: m/z=448 (M+H)⁺
Retention time HPLC: 1.35 min
HPLC method: A_10

Further Analogues of Compound 19:

The compounds listed in table 5 were synthesized analogously to example 19.1 using the appropriate amines and the corresponding chlorides.

TABLE 5

| | Structure | Name | Yield | Mass | Retention time | HPLC method | Chlorides |
|---|---|---|---|---|---|---|---|
| 19.2 | 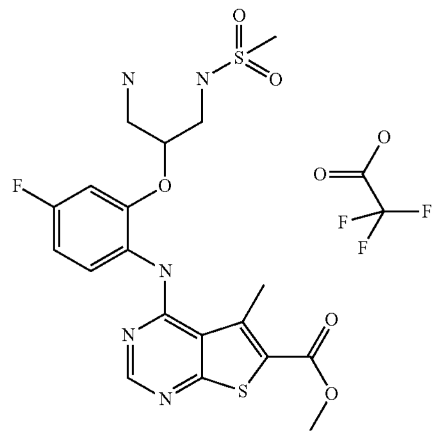 [SMILES: COC(=O)c1sc2ncnc(Nc3ccc(F)cc3OC(CN)CNS(C)(=O)=O)c2c1C ; O=C(O)C(F)(F)F] | Methyl 4-(2-(1-amino-3-(methyl-sulfonamido)-propan-2-yloxy)-4-fluoro-phenylamino)-5-methylthieno[2,3-d]pyrimidine-6-carboxylate trifluoroacetate | 50 mg | 484 | 1.22 | A_10 | |
| 19.3 | 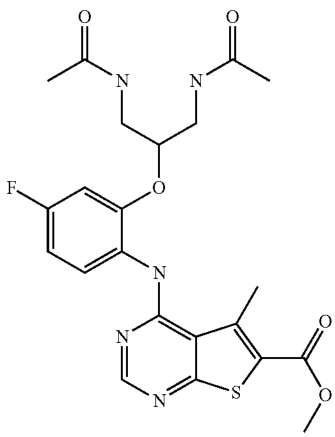 [SMILES: COC(=O)c1sc2ncnc(Nc3ccc(F)cc3OC(CNC(C)=O)CNC(C)=O)c2c1C] | Methyl 4-(2-(1,3-diacetamido-propan-2-yloxy)4-fluoro-phenylamino)-5-methylthieno[2,3-d]pyrimidine-6-carboxylate | 11 mg | 490 | 1.51 | A_10 | |

Compound 20

N-(3-(Dimethylamino)propyl)-4-(4-fluoro-2-(4-hydroxy-4-methylpentan-2-yloxy)phenylamino)-5-methyl-thieno[2,3-d]pyrimidine-6-carboxamide trifluoroacetate 20.1 Methyl 4-(4-fluoro-2-(4-hydroxy-4-methylpentan-2-yloxy)phenylamino)-5-methyl-thieno[2,3-d]pyrimidine-6-carboxylate

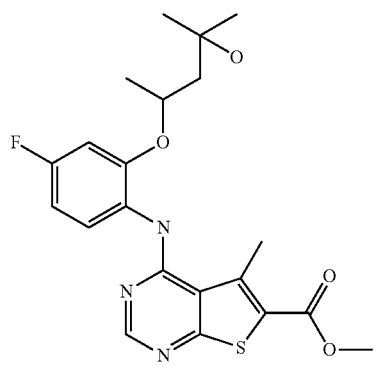 [SMILES: COC(=O)c1sc2ncnc(Nc3ccc(F)cc3OC(C)CC(C)(C)O)c2c1C]

4-Chloro-5-methyl-thieno[2,3-d]pyrimidine-6-carboxylic acid methyl ester (540 mg) and 4-(2-amino-5-fluorophenoxy)-2-methylpentan-2-ol (500 mg) were dissolved in dioxane (20 ml) and p-toluenesulfonic acid monohydrate (70 mg) was added. The reaction was heated under reflux for 2 h. Then the reaction mixture was allowed to cool to room temperature and concentrated in vacuo. The residue was dissolved in dichloromethane and washed with water. The organic layer was separated, dried, filtered and evaporated. The residue triturated with methanol and the precipitate was filtered to give the intended product.

Yield: 710 mg
ESI mass spectrum: m/z=434 (M+H)$^+$
Retention time HPLC: 2.02 min
HPLC method: A_9

20.2 4-(4-fluoro-2-(4-hydroxy-4-methylpentan-2-yloxy)phenylamino)-5-methyl-thieno[2,3-d]pyrimidine-6-carboxylic acid

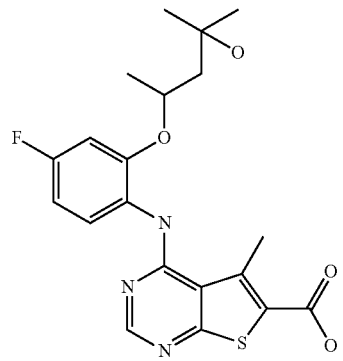 [SMILES: Cc1c(C(=O)O)sc2ncnc(Nc3ccc(F)cc3OC(C)CC(C)(C)O)c12]

Methyl 4-(4-fluoro-2-(4-hydroxy-4-methylpentan-2-yloxy)phenylamino)-5-methyl-thieno[2,3-d]pyrimidine-6-carboxylate (710 mg) was dissolved in methanol (50 ml) and aqueous NaOH (4M; 5 ml) was added. The reaction was stirred at room temperature overnight and then heated at 60° C. for 2 h. Finally the solution was neutralised and concentrated in vacuo. The residue was triturated with water. The resultant precipitate was filtered and dried.

Yield: 600 mg

ESI mass spectrum: m/z=420 (M+H)+

Retention time HPLC: 1.75 min

HPLC method: A_9

20.3 N-(3-(Dimethylamino)propyl)-4-(4-fluoro-2-(4-hydroxy-4-methylpentan-2-yloxy)phenylamino)-5-methyl-thieno[2,3-d]pyrimidine-6-carboxamide trifluoroacetate

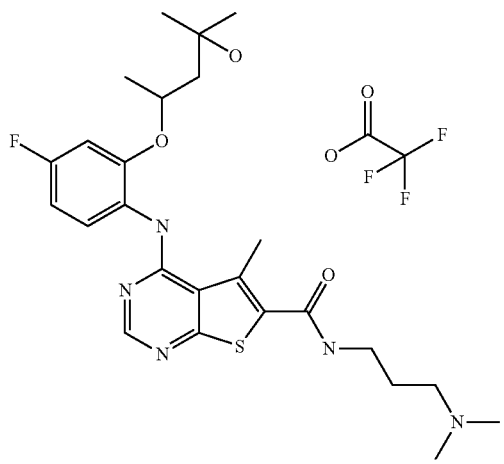 [SMILES: Cc1c(C(=O)NCCCN(C)C)sc2ncnc(Nc3ccc(F)cc3OC(C)CC(C)(C)O)c12 ; O=C(O)C(F)(F)F]

4-(4-Fluoro-2-(4-hydroxy-4-methylpentan-2-yloxy)phenylamino)-5-methyl-thieno[2,3-d]pyrimidine-6-carboxylic acid (100 mg) was dissolved in DMF (5 ml) and triethylamine (75 µl) was added. Then TBTU (80 mg) was added and the reaction was stirred for 5 minutes. Followed by N,N-dimethyl-1,3-propanediamine (35 µA the reaction mixture was stirred at room temperature for 2 h. An further aliquot of N,N-dimethyl-1,3-propanediamine and TBTU (40 mg) was added. The mixture was heated at 60° C. and stirred for 2 h. Then the reaction was concentrated in vacuo. The residue was dissolved in dichloromethane and washed with soda solution. The organic phase was purified by RP-chromatography (water with 0.2% trifluoroacetic acid/methanol 72-100%).

Yield: 132 mg

ESI mass spectrum: m/z=504 (M+H)+

Retention time HPLC: 1.18 min

HPLC method: A_9

Compound 21

5-Methyl-4-(2-(1,1,1-trifluoroproban-2yloxy)pyridin-3-ylamino)thieno[2,3-d]pyrimidine-6-carboxamide

21.1 Methyl 5-methyl-4-(2-(1,1,1-trifluoropropan-2yloxy)pyridin-3-ylamino)thieno[2,3-d]pyrimidine-6-carboxylate

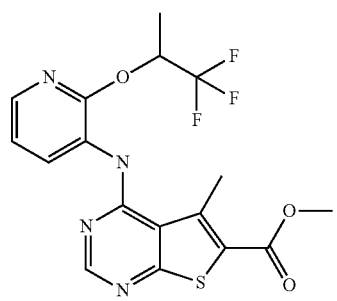 [SMILES: COC(=O)c1sc2ncnc(Nc3cccnc3OC(C)C(F)(F)F)c2c1C]

Prepared analogously to example 1.1 by heating under microwave irradiation at 110° C. using 2-(1,1,1-trifluoropropan-2-yloxy)pyridin-3-amine and 4-Chloro-5-methyl-thieno[2,3-d]pyrimidine-6-carboxylic acid methyl ester Yield: 270 mg ESI mass spectrum: m/z=413 (M+H)+

Retention time HPLC: 3.37 min

HPLC method: AC 1

21.2 5-Methyl-4-(2-(1,1,1-trifluoropropan-2-yloxy)pyridin-3-ylamino)thieno[2,3-d]pyrimidine-6-carboxylic acid

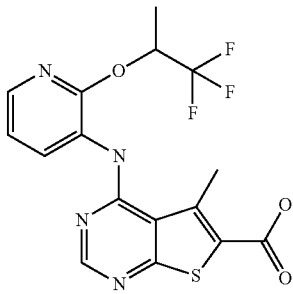 [SMILES: Cc1c(C(=O)O)sc2ncnc(Nc3cccnc3OC(C)C(F)(F)F)c12]

Prepared analogously to example 1.2 using Methyl 5-methyl-4-(2-(1,1,1-trifluoropropan-2yloxy)pyridin-3-ylamino)thieno[2,3-d]pyrimidine-6-carboxylate Yield: 278 mg ESI mass spectrum: m/z=399 (M+H)+

Retention time HPLC: 3.25 min

HPLC method: AC 1

21.3 5-Methyl-4-(2-(1,1,1-trifluoropropan-2-yloxy)pyridin-3-ylamino)thieno[2,3-d]pyrimidine-6-carboxamide

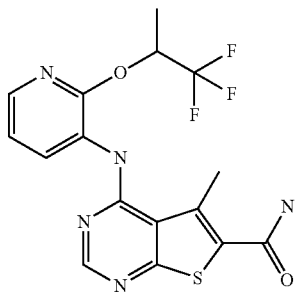 [SMILES: Cc1c(C(N)=O)sc2ncnc(Nc3cccnc3OC(C)C(F)(F)F)c12]

5-Methyl-4-(2-(1,1,1-trifluoropropan-2yloxy)pyridin-3-ylamino)thieno[2,3-d]pyrimidine-6-carboxylic acid (278 mg), HATU (320 mg) and Hünig's Base (144 μl) were dissolved in DMF (6.5 ml) at 0° C. The reaction was stirred for 30 minutes after this time NH₃ in dioxane (0.5 M; 5.3 ml) was added. The reaction was allowed to warm to room temperature overnight. The reaction mixture was concentrated in vacuo. The residue was extracted with dichloromethane and water. The organic layer was separated, dried and evaporated. The crude product was purified by chromatography (silica/dichloromethane: methanol: NH₃ 90:10:1).

Yield: 124 mg

ESI mass spectrum: m/z=398 (M+H)⁺

Retention time HPLC: 3.93 min

HPLC method: AC 1

Further Analogues of Example 21:

Prepared analogously to example 21.3 using 5-methyl-4-(2-(1,1,1-trifluoropropan 2yloxy)pyridin-3-ylamino)thieno[2,3-d]pyrimidine-6-carboxylic acid and the corresponding amine

| | Structure | Name | Yield | Mass | Retention time | HPLC method | Amine |
|---|---|---|---|---|---|---|---|
| 21.4 | 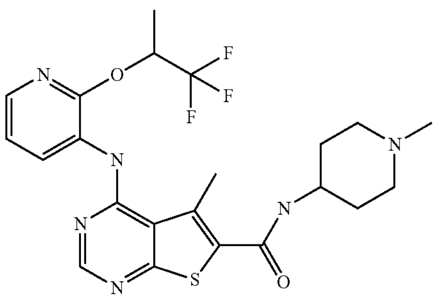 [SMILES: Cc1c(C(=O)NC2CCN(C)CC2)sc2ncnc(Nc3cccnc3OC(C)C(F)(F)F)c12] | 5-methyl-N-(1-methylpiperidin-4-yl)-4-(2-(1,1,1-trifluoropropan-2-yloxy)pyridin-3-ylamino)thieno[2,3-d]pyrrimidine-6-carboxamide | 134 mg | 495 | 2.23 | A_1 | |
| 21.5 | 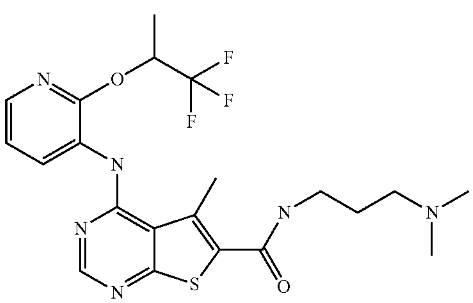 [SMILES: Cc1c(C(=O)NCCCN(C)C)sc2ncnc(Nc3cccnc3OC(C)C(F)(F)F)c12] | N-(3-(dimethylamino)propyl)-5-methyl-4-(2-(1,1,1-trifluoro-propan-2-yloxy)-pyridin-3-yl-amino)thieno[2,3-d]pyrimidine-6-carboxamide | 100 mg | 483 | 2.25 | A_1 | |
| 21.6 | 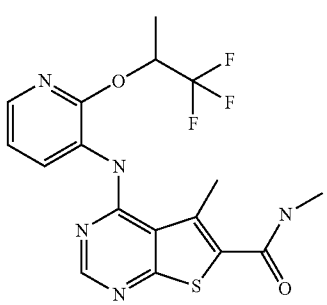 [SMILES: CNC(=O)c1sc2ncnc(Nc3cccnc3OC(C)C(F)(F)F)c2c1C] | N-Methyl-5-methyl-4-(2-(1,1,1-trifluoro-propan-2-yloxy)-pyridin-3-yl-amino)thieno[2,3-d]pyrimidine-6-N-methylcarboxamide | 150 mg | 412 | 3.05 | A_1 | |

| | Structure | Name | Yield | Mass | Retention time | HPLC method | Amine |
|---|---|---|---|---|---|---|---|
| 21.7 | 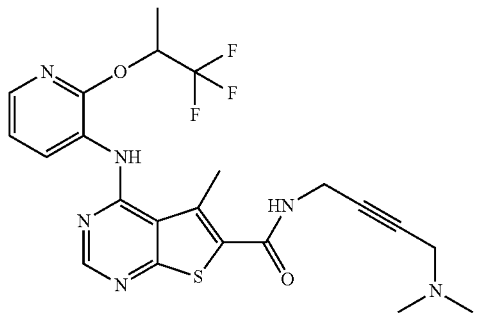 [SMILES: Cc1c(C(=O)NCC#CCN(C)C)sc2ncnc(Nc3cccnc3OC(C)C(F)(F)F)c12] | 5-Methyl-4-[2-(2,2,2-trifluoro-1-methyl-ethoxy)-pyridin-3-ylamino]-thieno[2,3-d]pyrimidine-6-carboxylic acid (4-dimethylamino-but-2-ynyl)-amide | 207 mg | 493 | 2.25 | AC 1 | |
| 21.8 | 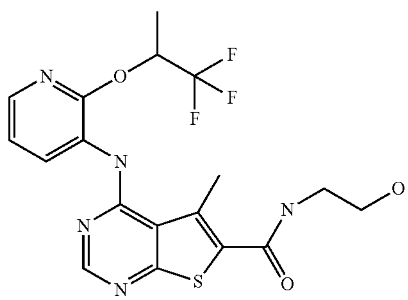 [SMILES: Cc1c(C(=O)NCCO)sc2ncnc(Nc3cccnc3OC(C)C(F)(F)F)c12] | 5-Methyl-4-[2-(2,2,2-trifluoro-1-methyl-ethoxy)-pyridin-3-ylamino]-thieno[2,3-d]pyrimidine-6-carboxylic acid (4-hydroxy-ethyl)-amide | 150 mg | 442 | 2.78 | AC 1 | |

Compound 22

4-(2-(1,3-Diethoxypropan-2-yloxy)-4-fluorophenylamino)-5-methyl-thieno[2,3-d]pyrimidine-6-carboxamide 22.1 Methyl 4-(2-(1,3-diethoxypropan-2-yloxy)-4-fluorophenylamino)-5-methyl-thieno[2,3-d]pyrimidine-6-carboxylate

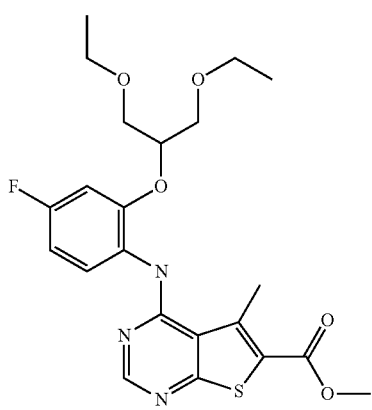 [SMILES: CCOCC(COCC)Oc1cc(F)ccc1Nc1ncnc2sc(C(=O)OC)c(C)c12]

Prepared analogously to example 18.1 using 4-Chloro-5-methyl-thieno[2,3-d]pyrimidine-6-carboxylic acid methyl ester and 2-(1,3-diethoxypropan-2-yloxy)-4-fluoroaniline.

The solvent dioxane was used instead of isopropanol and p-toluonesulfonic acid monohydrate was added.

Yield: 590 mg

ESI mass spectrum: m/z=464 (M+H)$^+$

Retention time HPLC: 3.75 min

HPLC method: A__10

22.2 4-(2-(1,3-Diethoxypropan-2-yloxy)-4-fluorophenylamino)-5-methyl-thieno[2,3-d]pyrimidine-6-carboxylic acid

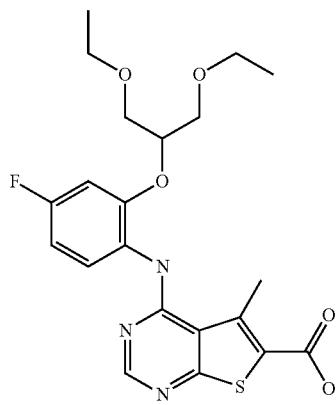

Prepared analogously to example 1.2 using methyl 4-(2-(1,3-diethoxypropan-2-yloxy)-4-fluorophenylamino)-5-methylthieno[2,3-d]pyrimidine-6-carboxylic acid. The reaction was performed at 80° C.

Yield: 390 mg

ESI mass spectrum: m/z=450 (M+H)$^+$

Retention time HPLC: 1.91 min

HPLC method: A__10

22.3 4-(2-(1,3-Diethoxypropan-2-yloxy)-4-fluorophenylamino)-5-methylthieno[2,3-d]pyrimidine-6-carboxamide

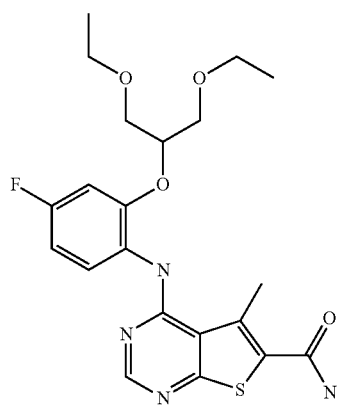 [SMILES: CCOCC(COCC)Oc1cc(F)ccc1Nc1ncnc2sc(C(N)=O)c(C)c12]

4-(2-(1,3-Diethoxypropan-2-yloxy)-4-fluorophenylamino)-5-methyl-thieno[2,3-d]pyrimidine-6-carboxylic acid (150 mg), TBTU (107, 2 mg) and Hünig's base (122 μl) were dissolved in THF (10 ml), ammonia (0.5M; 700 μl) was added and the mixture was stirred at room temperature overnight. Then it was evaporated and the residue dissolved in dichloromethane. The mixture was extracted with water and aqueous NaOH (0.5M). The organic layer was dried and concentrated in vacuo. The residue was triturated with Et$_2$O and a few drops of ethanol.

Yield: 105 mg
ESI mass spectrum: m/z=449 (M+H)$^+$
Retention time HPLC: 2.02 min
HPLC method: A_10

Compound 23

4-(2-(1,3-Difluoropropan-2-yloxy)-4-fluorophenylamino)-5-methyl-thieno[2,3-d]m/pryimidine-6-carboxamide

23.1 Methyl 4-(2-(1,3-difluoropropan-2-yloxy)-4-fluorophenylamino)-5-methyl-thieno[2,3-d]pyrimidine-6-carboxylate

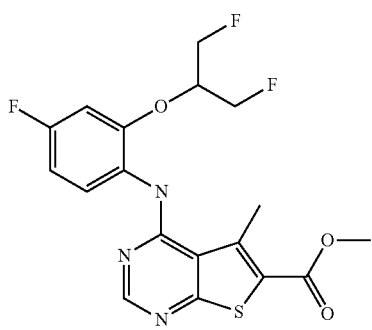

Prepared analogously to example 21.1 using 2-(1,3-difluoropropan-2-yloxy)-4-fluoroaniline and 4-Chloro-5-methyl-thieno[2,3-d]pyrimidine-6-carboxylic acid methyl ester.

Yield: 3.7 g
ESI mass spectrum: m/z=412 (M+H)$^+$
Retention time HPLC: 3.37 min
HPLC method: AC 1

23.2 4-(2-(1,3-Difluoropropan-2-yloxy)-4-fluorophenylamino)-5-methyl-thieno[2,3-d]pyrimidine-6-carboxylic acid

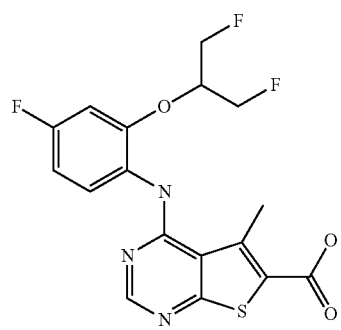 [SMILES: Cc1c(C(N)=O)sc2ncnc(Nc3ccc(F)cc3OC(CF)CF)c12]

Prepared analogously to example 1.2 using methyl 4-(2-(1,3-difluoropropan-2-yloxy)-4-fluorophenylamino)-5-methyl-thieno[2,3-d]pyrimidine-6-carboxylate Yield: 1.93 g
ESI mass spectrum: m/z=398 (M+H)$^+$
Retention time HPLC: 2.93 min
HPLC method: AC 1

23.3 4-(2-(1,3-Difluoropropan-2-yloxy)-4-fluorophenylamino)-5-methyl-thieno[2,3-d]pyrimidine-6-carboxamide

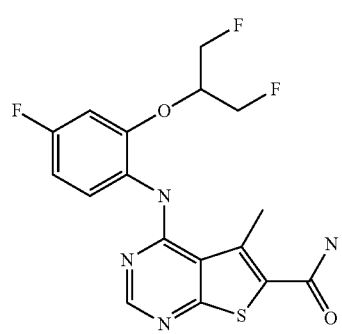

Prepared analogously to example 21.3 using 4-(2-(1,3-Difluoropropan-2-yloxy)-4-fluorophenylamino)-5-methyl-thieno[2,3-d]pyrimidine-6-carboxylic acid Yield: 180 mg
ESI mass spectrum: m/z=397 (M+H)$^+$
Retention time HPLC: 2.70 min
HPLC method: AC 1

Further Analogues of Compound 23:

The compounds listed in Table 6 were synthesized analogously to example 23.3 using 4-(2-(1,3-Difluoropropan-2-yloxy)-4-fluorophenylamino)-5-methylthieno[2,3-d]pyrimidine-6-carboxylic acid and the corresponding amine.

TABLE 6

| | Structure | Name | yield | Mass | Retention time | HPLC method |
|---|---|---|---|---|---|---|
| 23.4 | 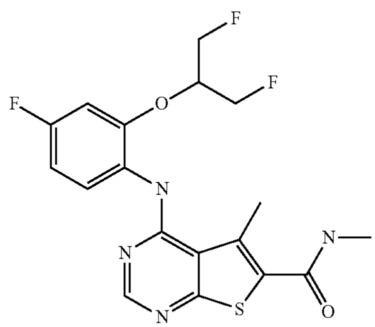 [SMILES: CNC(=O)c1sc2ncnc(Nc3ccc(F)cc3OC(CF)CF)c2c1C] | 4-(2-(1,3-difluoro-propan-2-yloxy)-4-fluorophenylamino)-N,5-dimethylthieno[2,3d]pyrimidine-6-carboxamide | 50 mg | 411 | 2.77 | AC1 |
| 23.5 | 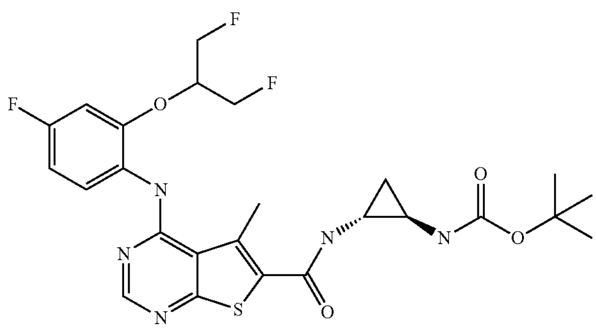 [SMILES: Cc1c(C(=O)N[C@@H]2C[C@H]2NC(=O)OC(C)(C)C)sc2ncnc(Nc3ccc(F)cc3OC(CF)CF)c12] | Tert-butyl (1R,2R)-2-(4-2(1,3-difluoro-propan-[2,3-d] pyrimidine-6-carboxamido) cyclopropyl carbamate | 134 mg | 522 | 3.05 | AC1 |
| 23.6 | 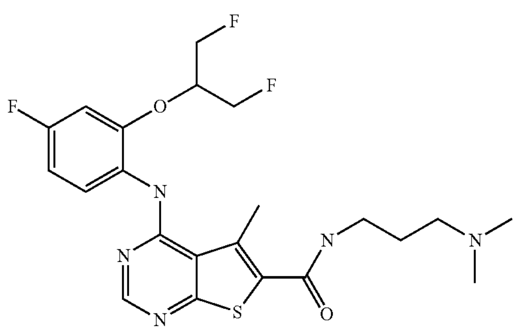 [SMILES: Cc1c(C(=O)NCCCN(C)C)sc2ncnc(Nc3ccc(F)cc3OC(CF)CF)c12] | 4-(2-(1,3-difluoro-propan-2-yloxy)-4-fluorophenylamino)-N-(3-(dimethylamino)-propyl)-5-methyl-thieno[2,3-d]-pyrimidine-6-carboxamide | 78 mg | 482 | 2.10 | AC1 |
| 23.7 | 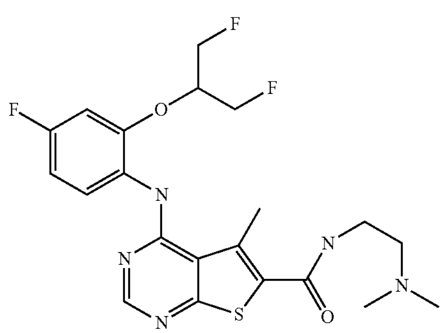 [SMILES: Cc1c(C(=O)NCCN(C)C)sc2ncnc(Nc3ccc(F)cc3OC(CF)CF)c12] | 4-(2-(1,3-difluoro-propan-2-yloxy)-4-fluorophenylamino)-N-(2-(dimethylamino)-ethyl)-5-methylthieno-[2,3-d]-pyrimidine-6-carboxamide | 102 mg | 468 | 2.14 | AC1 |

TABLE 6-continued

| | Structure | Name | yield | Mass | Retention time | HPLC method |
|---|---|---|---|---|---|---|
| 23.8 | 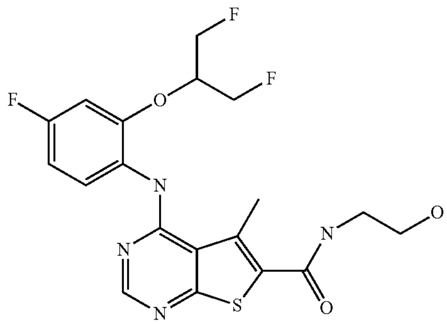 [SMILES: Cc1c(C(=O)NCCO)sc2ncnc(Nc3ccc(F)cc3OC(CF)CF)c12] | 4-(2-(1,3-difluoropropan-2-yloxy)-4-fluorophenylamino)-N-(2-(hydroxyethyl)-5-methylthieno[2,3-d]pyrimidine-6-carboxamide | 75 mg | 441 | 2.60 | AC1 |
| 23.9 | 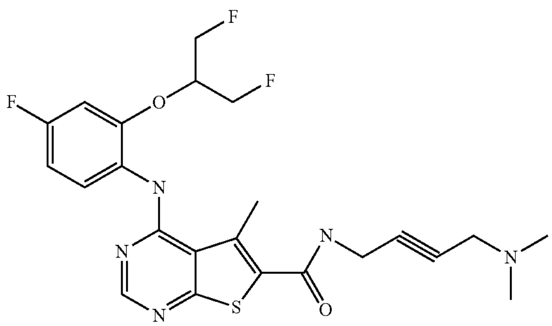 [SMILES: Cc1c(C(=O)NCC#CCN(C)C)sc2ncnc(Nc3ccc(F)cc3OC(CF)CF)c12] | 4-(2-(1,3-difluoropropan-2-yloxy)-4-fluorophenylamino)-N-(4-(dimethylamino)-but-2ynyl)-5-methyl-thieno[2,3-d]pyrimidine-6-carboxamide | 56 mg | 492 | 2.16 | AC1 |
| 23.10 | 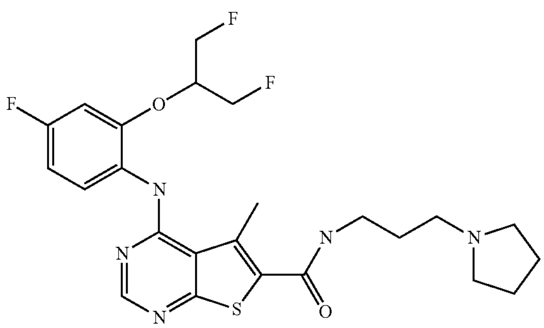 [SMILES: Cc1c(C(=O)NCCCN2CCCC2)sc2ncnc(Nc3ccc(F)cc3OC(CF)CF)c12] | 4-(2-(1,3-difluoropropan-2-yloxy)-4-fluorophenylamino)-5-methyl-N-(3-(pyrrolidin-1-yl)propyl)thieno[2,3-d]pyrimidine-6-carboxamide | 92 mg | 508 | 2.17 | AC1 |

Compound 24

4-(2-(1,3-Difluoropropan-2-yloxy)-4-fluorophenylamino)-5-methyl-N-(methylsulfonyl)thieno[2,3-d]pyrimidine-6-carboxamide

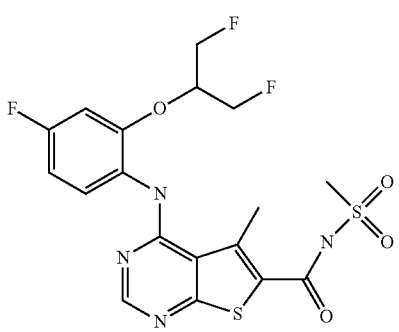 [SMILES: Cc1c(C(=O)NS(C)(=O)=O)sc2ncnc(Nc3ccc(F)cc3OC(CF)CF)c12]

4-(2-(1,3-Difluoropropan-2-yloxy)-4-fluorophenylamino)-5-methylthieno[2,3-d]pyrimidine-6-carboxylic acid (197 mg), 4-dimethylaminopyridine (76 mg) and 1-ethyl-3-(3-dimethylaminopropyl)carbodiimide hydrochloride (125 mg) was dissolved in dichloromethane (20 ml). Methanesulfonamide (59.5 mg) was added and the reaction was stirred at room temperature for about 24 h. The mixture was washed with a KHSO$_4$ solution. The organic layer was separated, dried and concentrated in vacuo. The residue was purified by chromatography (dichloromethane: methanol: NH$_3$ 80:20:1). The fractions were collected and triturated with diisopropyl ether.

Yield: 57 mg

ESI mass spectrum: m/z=475 (M+H)$^+$

Retention time HPLC: 3.11 min

HPLC method: AC 1

Compound 25

N-((trans)-2-Aminocyclopropyl)-4-(2-(1,3-difluoropropan-2-yloxy)-4-fluorophenylamino)-5-methylthieno[2,3-d]pyrimidine-6-carboxamide hydrochloride

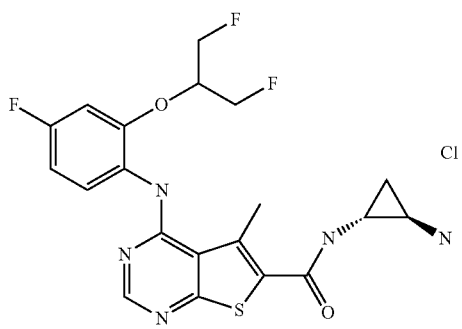 [SMILES: Cc1c(C(=O)N[C@@H]2C[C@H]2N)sc2ncnc(Nc3ccc(F)cc3OC(CF)CF)c12 ; Cl]

tert-Butyl (trans)-2-(4-(2-(1,3-difluoropropan[2,3-d]pyrimidine-6-carboxamido)cyclo propyl carbamate (130 mg) was dissolved in dioxane (8 ml) and a solution of HCl in dioxane (4M; 1.34 ml) was added. The reaction was stirred at room temperature overnight. Diethyl ether was added and the precipitate was filtered and washed with Et$_2$O to give the title compound.
Yield: 97 mg
ESI mass spectrum: m/z=452 (M+H)$^+$
Retention time HPLC: 2.10 min
HPLC method: AC 1

Compound 26

N-(3-(Dimethylamino)propyl-4-(4-fluoro-2-((tetrahydro-2-H-pyran-4-yl)methoxy)phenylamino)-5-methyl-thieno[2,3-d]pyrimidine-6-carboxamide

26. 1 Methyl-4-(4-fluoro-2-((tetrahydro-2-H-pyran-4-yl)methoxy)phenylamino)-5-methyl-thieno[2,3-d]pyrimidine-6-carboxylate

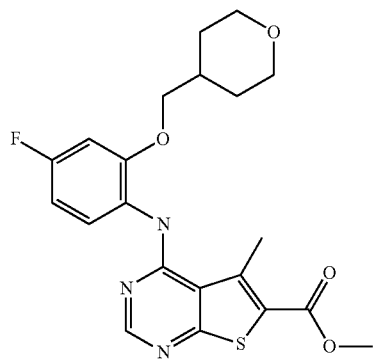 [SMILES: COC(=O)c1sc2ncnc(Nc3ccc(F)cc3OCC3CCOCC3)c2c1C]

Methyl 4-(4-fluoro-2-hydroxyphenylamino)-5-methyl-thieno[2,3-d]pyrimidine-6-carboxylate (100 mg) was dissolved in DMF (2 ml), 4-bromomethyltetrahydropyran (107 mg) and potassium carbonate (83 mg) were added. The reaction was stirred at 60° C. overnight. Then the reaction mixture was diluted with EtOAc and washed with water and brine. The solvent was removed in vacuo and the residue triturated with Et$_2$O.
Yield: 130 mg
ESI mass spectrum: m/z=432 (M+H)$^+$

26. 2 4-(4-Fluoro-2-((tetrahydro-2-H-pyran-4-yl)methoxy)phenylamino)-5-methyl-thieno[2,3-d]pyrimidine-6-carboxylic acid

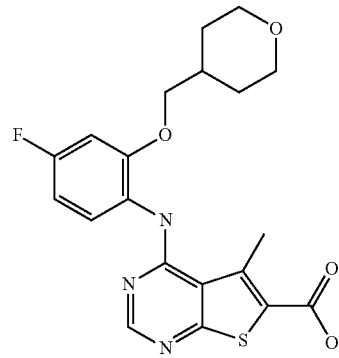 [SMILES: Cc1c(C(=O)O)sc2ncnc(Nc3ccc(F)cc3OCC3CCOCC3)c12]

Methyl-4-(4-fluoro-2-((tetrahydro-2-H-pyran-4-yl)methoxy)phenylamino)-5-methylthieno[2,3-d]pyrimidine-6-carboxylate (82 mg) and NaOH (2M; 0.5 ml) was dissolved in ethanol (2 ml). The reaction was stirred at room temperature overnight. Then the reaction mixture was diluted with dichloromethane and HCl (2M). The suspension was filtered, washed with brine and ether. The residue was dried in vacuo over P$_2$O$_5$.
Yield: 41 mg

26.3 N-(3-(Dimethylamino)propyl-4-(4-fluoro-2-((tetrahydro-2-H-pyran-4-yl)methoxy)phenylamino)-5-methyl-thieno[2,3-d]pyrimidine-6-carboxamide

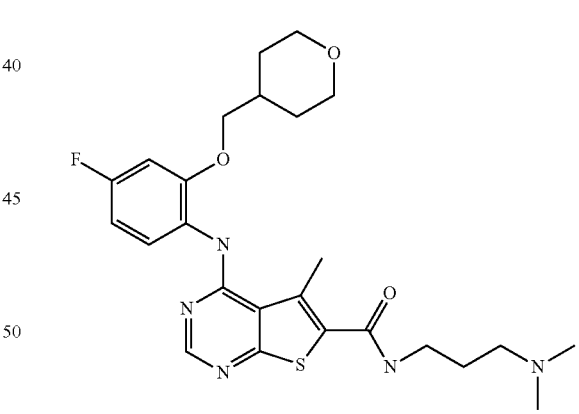

HATU (36 mg) was added to a solution of 4-(4-fluoro-2-((tetrahydro-2-H-pyran-4-yl)methoxy)phenylamino)-5-methylthieno[2,3-d]pyrimidine-6-carboxylic acid (36 mg) and DIPEA (17 µl) in DMF (1 ml). The reaction mixture was stirred for 40 min at room temperature. Then 3-(dimethylamino)propylamine (49 µl) was added. The reaction mixture was stirred at room temparture overnight. It was diluted with EtOAc and washed with water and brine. The organic phase was concentrated in vacuo. The residue was suspended in Et$_2$O and filtered and dried.
Yield: 40 mg
ESI mass spectrum: m/z=502 (M+H)$^+$

Example 27

4-(2-(2-Fluoropropoxy)pyridin-3-ylamino)-N-(2-hydroxyethyl)-5-methylthieno[2,3-d]pyrimidine-6-carboxamide

27.1 Methyl-4-(2-(2-fluoropropoxy)pyridin-3-ylamino)-5-methyl-thieno[2,3-d]pyrimidine-6-carboxylate

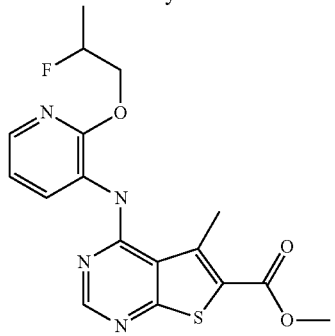

2-(2-Fluoropropoxy)pyridin-3-amine (153 mg) was dissolved in dioxane (30 ml), 4-Chloro-5-methyl-thieno[2,3-d]pyrimidine-6-carboxylic acid methyl ester (174.54 mg) and HCl in dioxane (4M; 25 µl) was added. The reactin was stirred at 60° C. for three days. The reaction was concentrated in vacuo.

Yield: 333 mg
Retention time HPLC: 2.37 min
HPLC method: 002_CC_ZQ4

27.2 4-(2-(2-Fluoropropoxy)pyridin-3-ylamino)-5-methyl-thieno[2,3-d]pyrimidine-6-carboxylic acid

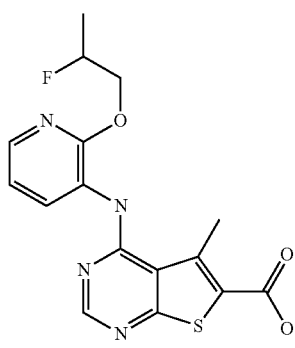 [SMILES: Cc1c(C(=O)O)sc2ncnc(Nc3cccnc3OCC(C)F)c12]

To a solution of methyl-4-(2-(2-fluoropropoxy)pyridin-3-ylamino)-5-methyl-thieno[2,3-d]pyrimidine-6-carboxylate (333 mg) in THF (10 ml) was added lithium hydroxide (1M; 8 ml) and the reaction stirred at room temperature overnight. The mixture was neutralized with HCl (1M; 8 ml) and concentrated in vacuo. The crude product was purified by chromatography.

Yield: 196 mg
ESI mass spectrum: m/z=363 (M+H)$^+$
Retention time HPLC: 1.91 min
HPLC method: 003_CC_ZQ7

27.3 4-(2-(2-Fluoropropoxy)pyridin-3-ylamino)-N-(2-hydroxyethyl)-5-methyl-thieno[2,3-d]pyrimidine-6-carboxamide

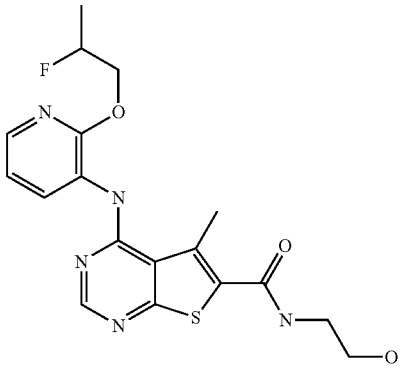 [SMILES: Cc1c(C(=O)NCCO)sc2ncnc(Nc3cccnc3OCC(C)F)c12]

4-(2-(2-Fluoropropoxy)pyridin-3-ylamino)-5-methylthieno[2,3-d]pyrimidine-6-carboxylic acid (36.2 mg), HATU (42 mg) and Hünig's base (34 µl) were dissolved in DMF (2 ml) and ethanolamine (9 µl) was added. The reaction was stirred at room temperature for 2 h. The reaction mixture was purified directly by chromatography.

Yield: 31 mg
ESI mass spectrum: m/z=406 (M+H)$^+$
Retention time HPLC: 2.09 min
HPLC method: 004_CC_ZQ6

Compound 77.4

Prepared analogously to example 27.3 using 4-(2-(2-Fluoropropoxy)pyridin-3-ylamino)-5-methyl-thieno[2,3-d]pyrimidine-6-carboxylic acid and the corresponding amine.

| Structure | Name | Yield | Mass | Retention time | HPLC method | amine |
|---|---|---|---|---|---|---|
| 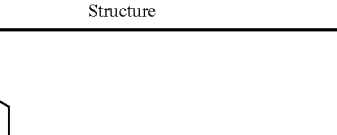 | N-(3-(dimethylamino)-propyl)-4-(2-(2-fluoropropoxy)pyridin-3-ylamino)-5-methyl-thieno[2,3-d]pyrimidine-6-carboxamide hydrochloride | 26 mg | 447 | 1.75 | 004_CC_ZQ6 | 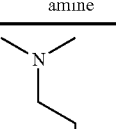 |

83

Compound 28

4-(2-(2-Methoxypropan-2-yloxy)pyridin-3-ylamino)-5-methylthieno[2,3-d]pyrimidine-6-carboxamide 28. 1 Methyl-4-(2-(1-methoxypropan-2-yloxy)pyridin-3-ylamino)-5-methyl-thieno[2,3-d]pyrimidine-6-carboxylate

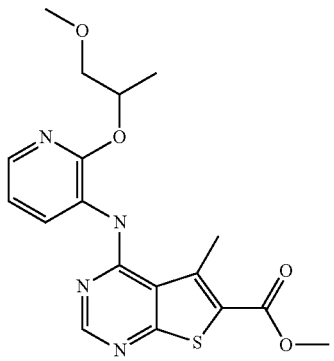 [SMILES: COCC(C)Oc1ncccc1Nc1ncnc2sc(C(=O)OC)c(C)c12]

Prepared analogously to example 27.1
Yield: 344 mg
Retention time HPLC: 2.40 min
HPLC method: 002_CC_ZQ4

28. 2 4-(2-(1-Methoxypropan-2-yloxy)pyridin-3-ylamino)-5-methylthieno[2,3-d]pyrimidine-6-carboxylic acid

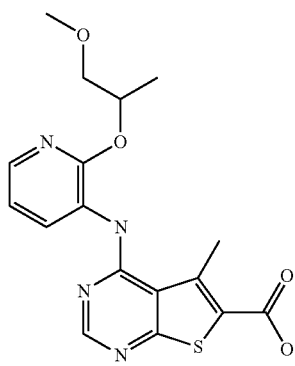 [SMILES: COCC(C)Oc1ncccc1Nc1ncnc2sc(C(N)=O)c(C)c12]

84

Prepared analogously to example 27.2 using methyl-4-(2-(1-methoxypropan-2-yloxy)pyridin-3-ylamino)-5-methylthieno[2,3-d]pyrimidine-6-carboxylate Yield: 119 mg
ESI mass spectrum: m/z=375 (M+H)$^+$
Retention time HPLC: 1.90 min
HPLC method: 003_CC_ZQ7

28. 3 4-(2-(1-Methoxygrogan-2-yloxy)gyridin-3-ylamino)-5-methyl-thieno[2,3-d]gyrimidine-6-carboxamide

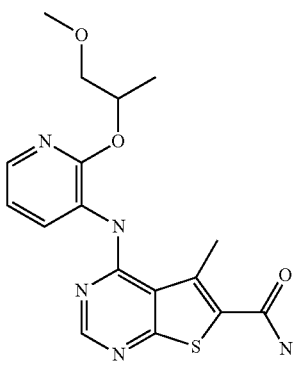

Prepared analogously to example 27.3 using 4-(2-(1-methoxypropan-2-yloxy)pyridin-3-ylamino)-5-methyl-thieno[2,3-d]pyrimidine-6-carboxylic acid (37 mg) and ammonia in dioxane (0.5M; 2 ml)

Yield: 23 mg
ESI mass spectrum: m/z=374 (M+H)$^+$
Retention time HPLC: 2.13 min
HPLC method: 004_CC_ZQ6

Further Analogues of 28:

Prepared analogously to example 29.3 using 4-(2-(1-methoxypropan-2-yloxy)pyridin-3-ylamino)-5-methylthieno[2,3-d]pyrimidine-6-carboxylic acid and the corresponding amine

| | Structure | Name | Yield | Mass | Retention time | HPLC method | Amine |
|---|---|---|---|---|---|---|---|
| 28.4 | 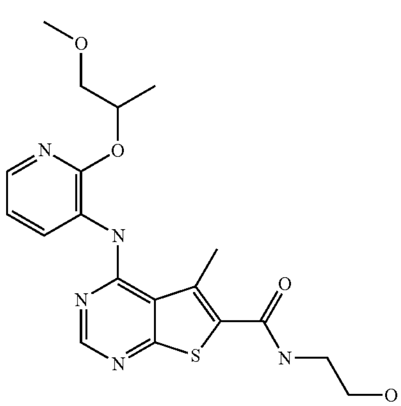 [SMILES: COCC(C)Oc1ncccc1Nc1ncnc2sc(C(=O)NCCO)c(C)c12] | N-(2-hydroxy-ethyl)-4-(2-(1-methoxy-propan-2-yloxy)pyridin-3-ylamino)-5-methylthieno-[2,3-d]-pyrimidine-6-carbox-amide | 16 mg | 418 | 2.11 | 004_CC_ZQ6 | HO-CH₂CH₂-NH₂ |

| Structure | Name | Yield | Mass | Retention time | HPLC method | Amine |
|---|---|---|---|---|---|---|
| 28.5 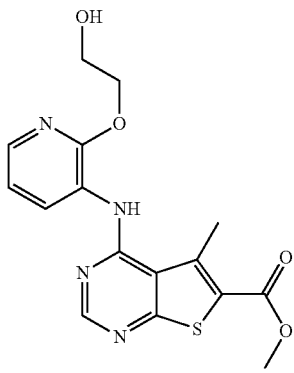 [SMILES: COC(=O)c1sc2ncnc(Nc3cccnc3OCCO)c2c1C] | N-(3-(di-methylamino)propyl)-4-(2-(1-methoxy-propan-2-yloxy)pyridin-3-ylamino)-5-methlthieno-[2,3-d]pyrimi-dine-6-carboxamide hydrochloride | 30 mg | 459 | 1.75 | 004_CC_ZQ6 | 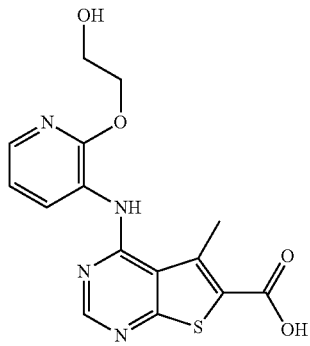 [SMILES: Cc1c(C(=O)O)sc2ncnc(Nc3cccnc3OCCO)c12] |

Compound 29

4-(2-(2-Hydroxyethoxy)pyridin-3-ylamino)-5-methyl-thieno[2,3-d]pyrimidine-6-carboxamide 29. 1 Methyl-4-(2-(2-hydroxyethoxy)pyridin-3-ylamino)-5-methyl-thieno[2,3-d]pyrimidine-6-carboxylate

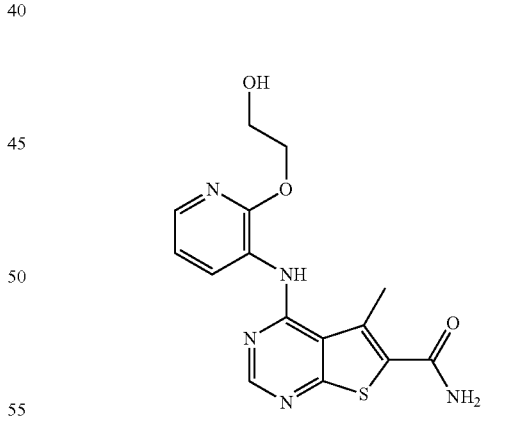

Prepared analogously to example 28.1 from 2-(3-aminopyridin-2-yloxy)ethanol (175 mg) and chloro-5-methyl-thieno[2,3-d]pyrimidine-6-carboxylic acid methyl ester (121 mg)
Yield: 475 mg
Retention time HPLC: 2.18 min
HPLC method: 002_CC_ZQ4

29. 2 4-(2-(2-Hydroxyethoxy)pyridin-3-ylamino)-5-methyl-thieno[2,3-d]pyrimidine-6-carboxylic acid Prepared analogously to example 28.1 from methyl-4-(2-(2-hydroxyethoxy)pyridin-3-ylamino)-5-methyl-thieno[2,3-d]pyrimidine-6-carboxylate Yield: 61 mg Retention time HPLC: 2.14 min HPLC method: 003_CC_ZQ7

29. 3 4-(2-(2-Hydroxyethoxy)pyridin-3-ylamino)-5-methylthieno[2,3-d]pyrimidine-6-carboxamide Prepared analogously to example 28.3 using 4-(2-(2-hydroxyethoxy)pyridin-3-ylamino)-5-methylthieno[2,3-d]pyrimidine-6-carboxylic acid (30.5 mg) and ammonia in dioxane (0.5M; 1.6 ml)

Yield: 13 mg

ESI mass spectrum: m/z=346 (M+H)$^+$

Retention time HPLC: 1.87 min

HPLC method: 004_CC_ZQ6

Compound 29.4

Prepared analogously to example 29.3 using 4-(2-(2-hydroxyethoxy)pyridin-3-ylamino)-5-methylthieno[2,3-d]pyrimidine-6-carboxylic acid and the corresponding amine

| Structure | Name | Yield | Mass | Retention time | HPLC method | amin |
|---|---|---|---|---|---|---|
| 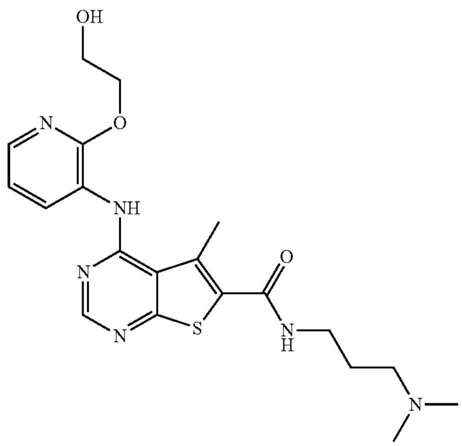 [SMILES: Cc1c(C(=O)NCCCN(C)C)sc2ncnc(Nc3cccnc3OCCO)c12] | N-(3-(dimethylamino)propyl)-4-(2-(2-hydroxyethoxy)pyridin-3-ylamino)-5-methylthieno[2,3-d]pyrimidine-6-carboxamide hydrochloride | 26 mg | 431 | 1.54 | 004_CC_ZQ6 |  |

Compound 30

4-(2-(2,2-Difluoroethoxy)pyridin-3-ylamino)-5-methyl-thieno[2,3-d]pyrimidine-6-carboxamide

30.1 Methyl-4-(2-(2,2-difluoroethoxy)pyridin-3-ylamino)-5-methyl-thieno[2,3-d]pyrimidine-6-carboxylate

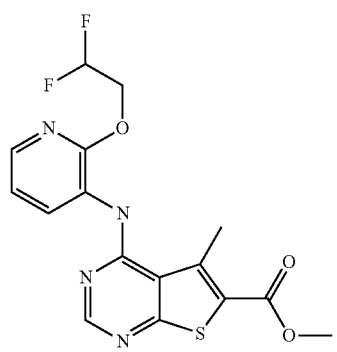 [SMILES: COC(=O)c1sc2ncnc(Nc3cccnc3OCC(F)F)c2c1C]

Prepared analogously to example 28.1 from 2-(2,2-Difluoroethoxy)pyridin-3-amine (171 mg) and Chloro-5-methyl-thieno[2,3-d]pyrimidine-6-carboxylic acid methyl ester (190 mg)

Yield: 376 mg

Retention time HPLC: 2.35 min

HPLC method: 002_CC_ZQ4

30.2 4-(2-(2,2-Difluoroethoxy)pyridin-3-ylamino)-5-methylthieno[2,3-d]pyrimidine-6-carboxylic acid

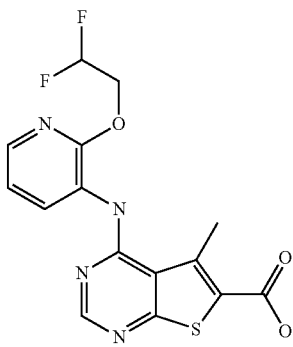 [SMILES: Cc1c(C(=O)O)sc2ncnc(Nc3cccnc3OCC(F)F)c12]

Prepared analogously to example 28.2 using methyl-4-(2-(2,2-difluoroethoxy)pyridin-3-ylamino)-5-methylthieno[2,3-d]pyrimidine-6-carboxylate (376 mg).

Yield: 220 mg

ESI mass spectrum: m/z=367 (M+H)$^+$

Retention time HPLC: 1.91 min

HPLC method: 007_CC_ZQ7

30. 3 4-(2-(2,2-Difluoroethoxy)pyridin-3-ylamino)-5-methyl-thieno[2,3-d]pyrimidine-6-carboxamide

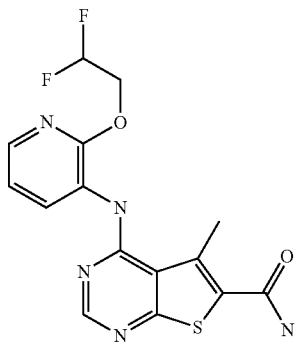 [SMILES: Cc1c(C(N)=O)sc2ncnc(Nc3cccnc3OCC(F)F)c12]

Prepared analogously to example 28.3 from 4-(2-(2,2-difluoroethoxy)pyridin-3-ylamino)-5-methyl-thieno[2,3-d]pyrimidine-6-carboxylic acid (36.6 mg) and ammonia in dioxane (0.5M; 2 ml).

Yield: 18 mg

ESI mass spectrum: m/z=366 (M+H)$^+$

Retention time HPLC: 2.09 min

HPLC method: 004_CC_ZQ6

Further Analogues of 30:

Prepared analogously to example 30.3 from 4-(2-(2,2-Difluoroethoxy)pyridin-3-ylamino)-5-methylthieno[2,3-d]pyrimidine-6-carboxylic acid and the corresponding amine

| | Structure | Name | Yield | Mass | Retention time | HPLC method | amine |
|---|---|---|---|---|---|---|---|
| 30.4 | 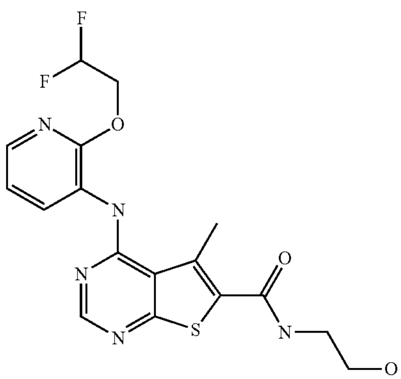 [SMILES: Cc1c(C(=O)NCCO)sc2ncnc(Nc3cccnc3OCC(F)F)c12] | 4-(2-(2,2-difluoroethoxy)-pyridin-3-ylamino)-N-(2-hydroxyethyl)-5-methylthieno[2,3-d]pyrimidine-6-carboxamide | 29 mg | 410 | 2.06 | 004_CC_ZQ6 | NH$_2$-CH$_2$CH$_2$-OH |
| 30.5 | 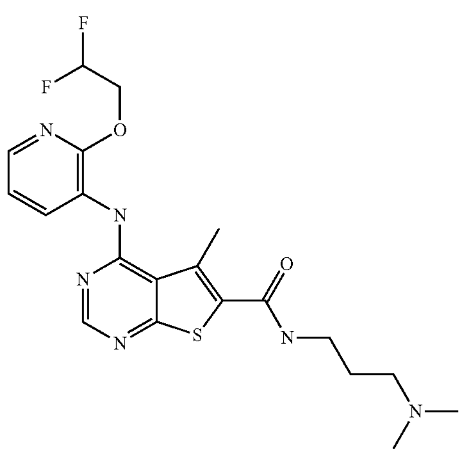 [SMILES: Cc1c(C(=O)NCCCN(C)C)sc2ncnc(Nc3cccnc3OCC(F)F)c12] | 4-(2-(2,2-difluoroethoxy)-pyridin-3-ylamino)-N-(3-(dimethylamino)propyl)-5-methyl-thieno[2,3-d]pyrimidine-6-carboxamide hydrochloride | 12 mg | 451 | 1.71 | 004_CC_ZQ6 | |

Compound 31

4-(2-(1-(Ethylamino)-1-oxopropan-2-yloxy)-4-fluorophenylamino)-5-methyl-thieno[2,3-d]pyrimidine-6-carboxamide

31.1 Methyl-4-(2-(1-tert-butoxy-1-oxopropan-2-yloxy)-4-fluorophenylamino)-5-methyl-thieno[2,3-d]pyrimidine-6-carboxylate

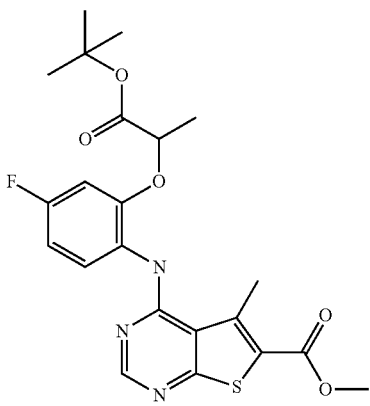 [SMILES: COC(=O)c1sc2ncnc(Nc3ccc(F)cc3OC(C)C(=O)OC(C)(C)C)c2c1C]

Methyl 4-(4-fluoro-2-hydroxyphenylamino)-5-methyl-thieno[2,3-d]pyrimidine-6-carboxylate (100 mg) and Caesium carbonate (240 mg) was dissolved in acetonitrile (2 ml) and 2-bromopropionic acid tert-butylester (70 mg) was added. The reaction mixture was stirred at 60° C. for 2 h. Then the reaction was quenched with water and the precipitate was collected by filtration. The residue cake was washed with water and a few drops of methanol.

Yield: 103 mg
ESI mass spectrum: m/z=462 (M+H)$^+$

31.2 2-(5-Fluoro-2-(6-(methoxycarbonyl)-5-methylthieno[2,3-d]pyrimidin-4-ylamino)phenoxy)propanoic acid

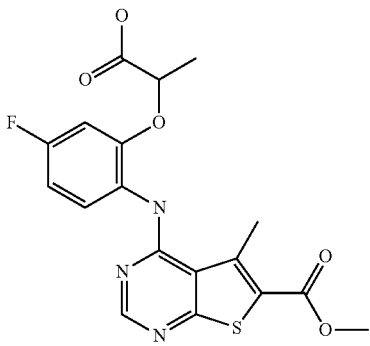 [SMILES: COC(=O)c1sc2ncnc(Nc3ccc(F)cc3OC(C)C(=O)O)c2c1C]

Prepared analogously to example 8.1 using methyl-4-(2-(1-tert-butoxy-1-oxopropan-2-yloxy)-4-fluorophenylamino)-5-methyl-thieno[2,3-d]pyrimidine-6-carboxylate (2.1 g) and 50% trifluoroacetic acid in dichloromethane (20 ml).

Yield: 1.9 g
ESI mass spectrum: m/z=406 (M+H)$^+$
Retention time HPLC: 1.96 min
HPLC method: A_9

31.3 Methyl 4-(2-(1-(ethylamino)-1-oxoproban-2-yloxy)-4-fluorophenylamino)-5-methylthieno[2,3-d]pyrimidine-6-carboxylate

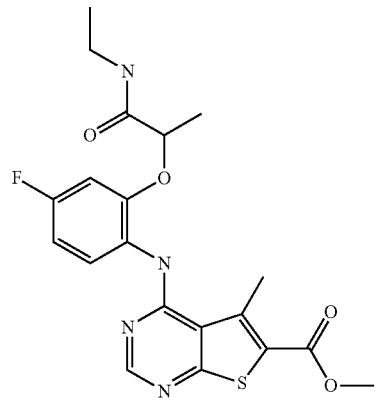

To a solution of 2-(5-fluoro-2-(6-(methoxycarbonyl)-5-methyl-thieno[2,3-d]pyrimidin-4-ylamino)phenoxy)propanoic acid (500 mg) and TBTU (400 mg) in acetonitrile (10 ml) was added triethylamine (430 μl). The mixture was stirred for 20 min. Then ethylamine (2M; 1.5 ml) was added and the mixture was stirred at room temperature overnight. Then the reaction mixture was diluted with methanol and purified by chromatography.

Yield: 360 mg
ESI mass spectrum: m/z=433 (M+H)$^+$
Retention time HPLC: 1.89 min
HPLC method: A_9

31.4 4-(2-(1-(Ethylamino)-1-oxoproban-2-yloxy)-4-fluorophenylamino)-5-methyl-thieno[2,3-d]pyrimidine-6-carboxylic acid

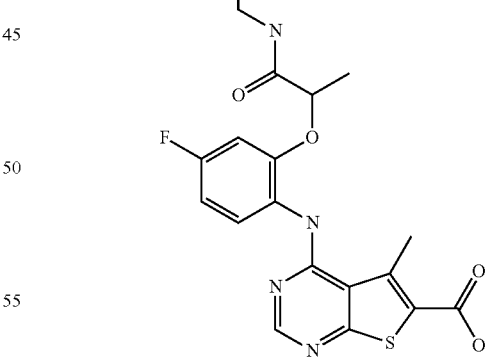

Prepared analogously to example 1.2 from methyl 4-(2-(1-(ethylamino)-1-oxopropan-2-yloxy)-4-fluorophenylamino)-5-methyl-thieno[2,3-d]pyrimidine-6-carboxylate (360 mg).

The reaction stirred at 50° C. overnight.
Yield: 299 mg
ESI mass spectrum: m/z=419 (M+H)$^+$
Retention time HPLC: 2.65 min
HPLC method: A_4

31.5 4-(2-(1-(Ethylamino)-1-oxopropan-2-yloxy)-4-fluorophenylamino)-5-methyl-tieno[2,3-d]pyrimidine-6-carboxamide

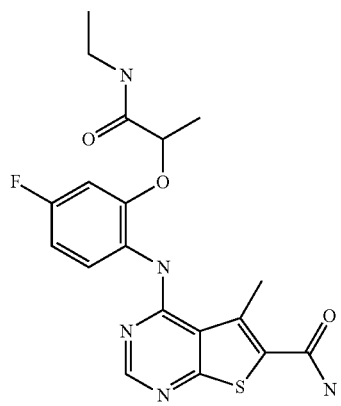 [SMILES: CCNC(=O)C(C)Oc1cc(F)ccc1Nc1ncnc2sc(C(N)=O)c(C)c12]

Prepared analogously to example 1.3 using 4-(2-(1-(ethylamino)-1-oxopropan-2-yloxy)-4-fluorophenylamino)-5-methylthieno[2,3-d]pyrimidine-6-carboxylic acid (60 mg) and ammonia in THF (0.5 M; 600 µl).

Yield: 25 mg

ESI mass spectrum: m/z=418 (M+H)$^+$

Retention time HPLC: 1.41 min

HPLC method: A_9

Further Analogues to 31:

Prepared analogously to example 32.5 from the corresponding amine and 4-(2-(1-(ethylamino)-1-oxopropan-2-yloxy)-4-fluorophenylamino)-5-methylthieno[2,3-d]pyrimidine-6-carboxylic acid

| | Structure | Name | Yield | Mass | Retention time | HPLC method | amine |
|---|---|---|---|---|---|---|---|
| 31.6 | 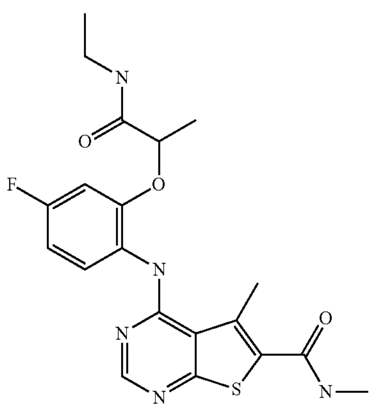 [SMILES: CCNC(=O)C(C)Oc1cc(F)ccc1Nc1ncnc2sc(C(=O)NC)c(C)c12] | 4-(2-(1-(ethylamino)-1-oxo-propan-2-yloxy)-4-fluorophenyl-amino)-N,5-dimethyl-thieno[2,3-d]pyrimidine-6-carbox-amide | 30 mg | 432 | 1.65 | A_9 | |
| 31.7 | 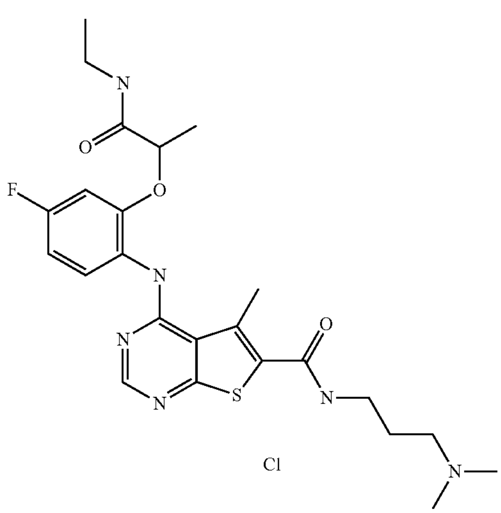 [SMILES: CCNC(=O)C(C)Oc1cc(F)ccc1Nc1ncnc2sc(C(=O)NCCCN(C)C)c(C)c12 ; Cl] | N-(3-(di-methylamino)propyl)-4-(2-(1-(ethyl-amino)-1-oxo-propan-2-yloxy)-4-fluorophenyl-amino)-5-methythieno-[2,3-d]pyrimi-dine-6-carboxamide hydrochloride | 32 mg | 503 | 1.97 | A_9 | |

Compound 32

Methyl 4-(2-(1-(2-(dimethylamino)ethylamino)-1-oxopropan-2-yloxy)-4-fluorophenylamino)-5-methyl-thieno[2,3-d]pyrimidine-6-carboxylate 32. 1 Methyl 4-(2-(1-(2-(dimethylamino)ethylamino)-1-oxopropan-2-yloxy)-4-fluorophenylamino)-5-methyl-thieno[2,3-d]pyrimidine-6-carboxylate

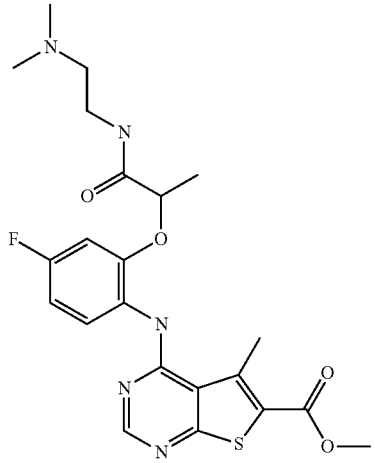 [SMILES: COC(=O)c1sc2ncnc(Nc3ccc(F)cc3OC(C)C(=O)NCCN(C)C)c2c1C]

Prepared analogously to example 32.3 from 2-(5-fluoro-2-(6-(methoxycarbonyl)-5-methylthieno[2,3-d]pyrimidin-4-ylamino)phenoxy)propanoic acid (200 mg) and 2-dimethylaminoethylamine (70 μl)

Yield: 136 mg
ESI mass spectrum: m/z=476 (M+H)+
Retention time HPLC: 2.17 min
HPLC method: A_4

Compounds 32.2-32.35

Step 1

Methyl 4-(4-fluoro-2-hydroxyphenylamino)-5-methylthieno[2,3-d]pyrimidine-6-carboxylate (667 mg) and the corresponding alcohol (e.g ethylen glycol 3 eq=372 mg) were dissolved in THF (30 ml). Under a nitrogen atmosphere triphenylphosphine (1.1 g) and diisopropyl azodicarboxylate (844 μl) were added and the reaction was stirred at room temperature for three days. An additional aliqout of the alcohol, diisopropyl azodicarboxylate and triphenylphosphine was added and the reaction was stirred overnight. Then the reaction mixture was filtered and washed with dichloromethane:methanol 9:1. The filtrate was concentrated in vacuo and the residue was purified by chromatography to give the intermediate esters

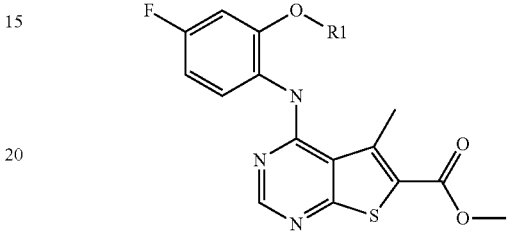

Step 2:

The intermediate esters (step 1) were dissolved in a mixture of methanol (10 ml)/THF (5 ml) and NaOH (1M; 5 ml) was added. The reaction was stirred at room temperature for three days. The solvent was concentrated in vacuo and the residue was neutralized with HCl (1M; 5 ml) and the precipitate was collected by filtration. The residue cake was dried, suspended in acetonitrile, acidified with HCl and concentrated in vacuo to give the intermediate acids (a-l)

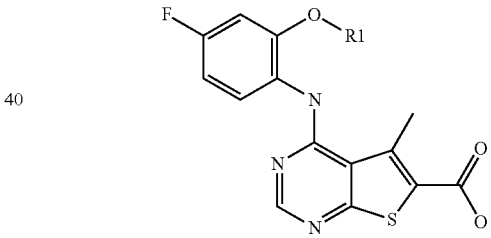

| Final compound | Intermediate product | R1 | Retention time | HPLC method |
|---|---|---|---|---|
| 32.2 | a | (cyclopropyl-CH2-C≡N group) | 2.69 | 004_CC_ZQ7 |
| 32.3 | b | (CH2CF3 with F) | 2.42 | 004_CC_ZQ6 |
| 32.4 | c | (CH2CHF2 group) | 2.76 | 004_CC_ZQ7 |

-continued

| Final compound | Intermediate product | R1 | Retention time | HPLC method |
|---|---|---|---|---|
| 32.5 | d | (cyclopropyl with 2 F, CH2, OC(CH3)2-) | 2.47 | 004_CC_ZQ7 |
| 32.6 | e | CH3O-CH2-CH(CH2F)-CH2-O- | 2.8 | 004_CC_ZQ7 |
| 32.7 | f | FCH2-CH(CH3)-O- | 2.82 | 004_CC_ZQ7 |
| 32.8 | g | CH3O-CH2-CH(CH2-OCH3)-... | 2.55 | 004_CC_ZQ7 |
| 32.9 | h | HOCH2CH2CH2-O- | 2.62 | 004_CC_ZQ7 |
| 32.10 | i | CH3O-CH2-CH(CH3)-O- | 2.86 | 004_CC_ZQ7 |
| 32.11 | j | CF3-CH2-CH2-CH2-O- | 2.79 | 004_CC_ZQ7 |
| 32.12 | k | CH3-CHF-CH2-CH2-O- | 2.82 | 004_CC_ZQ7 |

-continued

| Final compound | Intermediate product | R1 | Retention time | HPLC method |
|---|---|---|---|---|
| 32.13 | 1 | 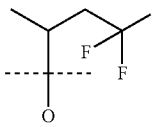 | 2.68 | 003_CC_ZQ7 |

Step 3

The acid a and Hünig's base (25 μl) was dissolved in DMF (3 ml). After a few minutes HATU (42 mg) was added. To this mixture N,N-dimethyl-1,3-propanediamine (19 μl) was added. The reaction mixture was stirred at room temperature overnight. The mixture was purified by chromatography to yield compound 35.

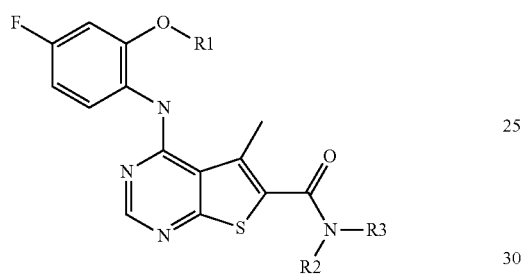

The following compounds were synthesized in an analogue manner:

| Final compound | Intermediate product | NR2R3 | Mass | Retention time | HPLC method |
|---|---|---|---|---|---|
| 32.14 | a | 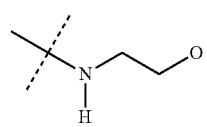 | 456 | 1.98 | 002_CC_ZQ4 |
| 32.15 | a | 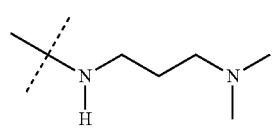 | 497 | 1.76 | 002_CC_ZQ4 |
| 32.16 | b | 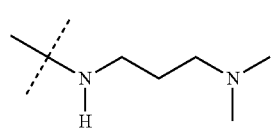 | 486 | 1.78 | 002_CC_ZQ4 |
| 32.17 | c | 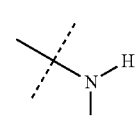 | 383 | 2.01 | 002_CC_ZQ4 |
| 32.18 | c | 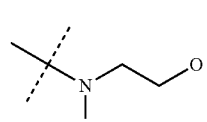 | 427 | 2.00 | 002_CC_ZQ4 |

-continued

| Final compound | Intermediate product | NR2R3 | Mass | Retention time | HPLC method |
|---|---|---|---|---|---|
| 32.19 | c | ⋮N(H)CH₂CH₂CH₂N(CH₃)₂ | 468 | 1.77 | 002_CC_ZQ4 |
| 32.20 | d | ⋮N(H)CH₂CH₂OH | 453 | 2.07 | 002_CC_ZQ4 |
| 32.21 | d | ⋮N(H)H | 409 | 2.07 | 002_CC_ZQ4 |
| 32.22 | d | ⋮N(H)CH₂CH₂CH₂N(CH₃)₂ | 494 | 1.82 | 002_CC_ZQ4 |
| 32.23 | e | ⋮N(H)CH₂CH₂OH | 453 | 2.02 | 002_CC_ZQ4 |
| 32.24 | e | ⋮N(H)CH₂CH₂CH₂N(CH₃)₂ | 494 | 1.79 | 002_CC_ZQ4 |
| 32.25 | e | ⋮N(H)H | 408 | 2.04 | 002_CC_ZQ4 |
| 32.26 | f | ⋮N(H)CH₂CH₂CH₂N(CH₃)₂ | 464 | 1.80 | 002_CC_ZQ4 |
| 32.27 | f | ⋮N(H)CH₂CH₂OH | 422 | 2.03 | 002_CC_ZQ4 |
| 32.28 | f | ⋮N(H)H | 378 | 2.05 | 002_CC_ZQ4 |
| 32.29 | g | ⋮N(H)CH₂CH₂OH | 451 | 1.87 | 002_CC_ZQ4 |
| 32.30 | g | ⋮N(H)H | 407 | 1.89 | 002_CC_ZQ4 |

-continued

| Final compound | Intermediate product | NR2R3 | Mass | Retention time | HPLC method |
|---|---|---|---|---|---|
| 32.31 | g | (CH3)2C-NH-CH2CH2CH2-N(CH3)2 structure | 492 | 1.67 | 002_CC_ZQ4 |
| 32.32 | h | (CH3)2C-NH2 structure | 363 | 1.97 | 002_CC_ZQ4 |
| 32.33 | h | (CH3)2C-NH-CH2CH2-OH structure | 407 | 1.96 | 002_CC_ZQ4 |
| 32.34 | h | (CH3)2C-NH-CH2CH2CH2-N(CH3)2 structure | 448 | 1.73 | 002_CC_ZQ4 |
| 32.35 | i | (CH3)2C-NH-CH2CH2CH2-N(CH3)2 structure | 476 | 1.81 | 002_CC_ZQ4 |
| 32.36 | i | (CH3)2C-NH-CH2CH2-OH structure | 435 | 2.06 | 002_CC_ZQ4 |
| 32.37 | i | (CH3)2C-NH2 structure | 391 | 2.08 | 002_CC_ZQ4 |
| 32.38 | j | (CH3)2C-NH-CH2CH2CH2-N(CH3)2 structure | 500 | 1.80 | 002_CC_ZQ4 |
| 32.39 | k | (CH3)2C-NH-CH2CH2CH2-N(CH3)2 structure | 464 | 1.8 | 002_CC_ZQ4 |
| 32.40 | l | (CH3)2C-NH-CH2CH2CH2-N(CH3)2 structure | 514 | 2.71 | 003_CC_ZQ7 |
| 32.41 | l | N-methylpiperidin-4-yl amine structure | 526 | 2.68 | 003_CC_ZQ7 |

-continued

| Final compound | Intermediate product | NR2R3 | Mass | Retention time | HPLC method |
|---|---|---|---|---|---|
| 32.42 | 1 | (structure) | 540 | 2.81 | 003_CC_ZQ7 |

The acid f and Hünig's base (15 μl) was dissolved in DMF (2 ml). After a few minutes TBTU (21.2 mg) was added. To this mixture was added the amin (0.07 mmol). The reaction mixture was stirred at room temperature overnight. The mixture was purified by chromatography.

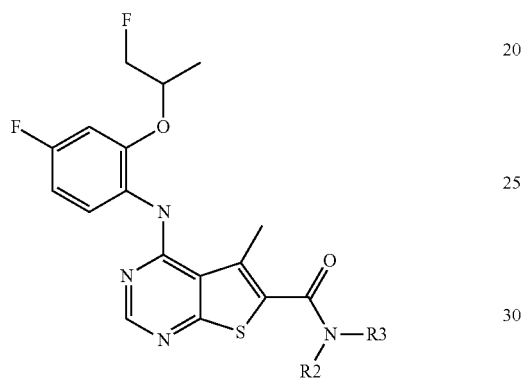

The following compounds were synthesized in an analogue manner:

| Final compound | Intermediate product | NR2R3 | Mass | Retention time | HPLC method |
|---|---|---|---|---|---|
| 32.43 | f | (structure) | 490 | | |
| 32.44 | f | (structure) | 490 | | |
| 32.45 | f | (structure) | 490 | | |

Compound 33

4-(2-((1-(Cyanomethyl)cyclopropyl)methoxy)pyridin-3-ylamino)-N-(3-(dimethylamino)propyl)-5-methylthieno[2,3-d]pyrimidine-6-carboxamide hydrochloride

33.1 Methyl 4-(2-((1-(cyanomethyl)cyclopropyl)methoxy)pyridin-3-ylamino)-5-methylthieno[2,3-d]pyrimidine-6-carboxylate

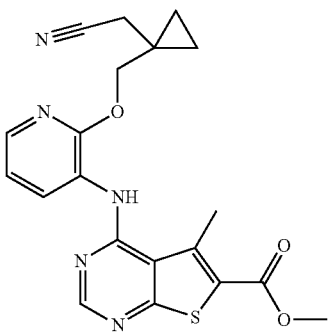 [SMILES: COC(=O)c1sc2ncnc(Nc3cccnc3OCC3(CC#N)CC3)c2c1C]

Prepared analogously to example 32.1 using 2-(1-(((3-aminopyridin-2-yloxy)methyl)cyclopropyl)acetonitrile (264 mg) and chloro-5-methyl-thieno[2,3-d]pyrimidine-6-carboxylic acid methyl ester (152 mg).

Retention time HPLC: 2.13 min
HPLC method: 007_CC_ZQ5

33.2 4-(2-((1-(Cyanomethyl)cyclopropyl)methoxy)pyridin-3-ylamino)-5-methylthieno[2,3-d]pyrimidine-6-carboxylic acid

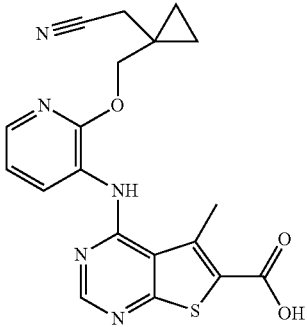 [SMILES: Cc1c(C(=O)O)sc2ncnc(Nc3cccnc3OCC3(CC#N)CC3)c12]

Prepared analogously to example 32 Step 2 using methyl 4-(2-((1-(cyanomethyl)cyclopropyl)methoxy)pyridin-3-ylamino)-5-methylthieno[2,3-d]pyrimidine-6-carboxylate Yield: 85 mg
Retention time HPLC: 2.23 min
HPLC method: 003_CC_ZQ6

33.3 4-(2-((1-(Cyanomethyl)cyclopropyl)methoxy)pyridin-3-ylamino)-N-(3-(dimethylamino)propyl)-5-methyl-thieno[2,3-d]pyrimidine-6-carboxamide hydrochloride

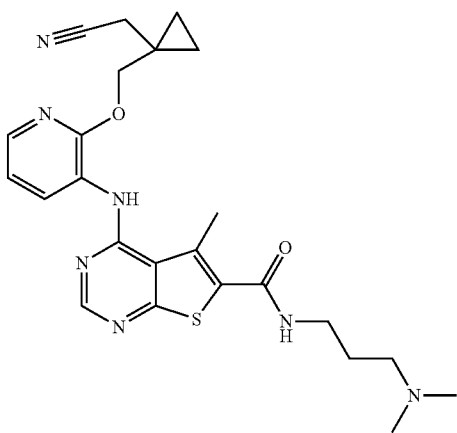 [SMILES: Cc1c(C(=O)NCCCN(C)C)sc2ncnc(Nc3cccnc3OCC3(CC#N)CC3)c12]

Prepared analogously to example 32.3 using 4-(2-((1-(cyanomethyl)cyclopropyl)methoxy)pyridin-3-ylamino)-5-methyl-thieno[2,3-d]pyrimidine-6-carboxylic acid (42.5 mg) and N,N-dimethyl-1,3-propanediamine (17 mg).

Yield: 42.7 mg
ESI mass spectrum: m/z=480 (M+H)$^+$
Retention time HPLC: 1.69 min
HPLC method: 004_CC_ZQ6

Compound 33.4

Prepared analogously to example 32.3 using 4-(2-((1-(cyanomethyl)cyclopropyl)-methoxy)pyridin-3-ylamino)-5-methylthieno[2,3-d]pyrimidine-6-carboxylic acid and ammonia.

| Structure | Name | Yield | Mass | Retention time | HPLC method |
|---|---|---|---|---|---|
|  | 4-(2-((1-(cyanomethyl)cyclopropyl)methoxy)pyridin-3-ylamino)-5-methylthieno[2,3-d]pyrimidine-6-carboxamide | 18.5 mg | 395 | 2.00 | 004_CC_ZQ6 |

Compound 34

4-(2-((2,2-Difluorocyclopropyl)methoxy)pyridin-3-ylamino)-N-(3-(dimethylamino)propyl)-5-methylthieno[2,3-d]pyrimidine-6-carboxamide hydrochloride

34.1 Methyl 4-(2-((2,2-difluorocyclopropyl)methoxy)pyridin-3-ylamino)-5-methylthieno[2,3-d]pyrimidine-6-carboxylate

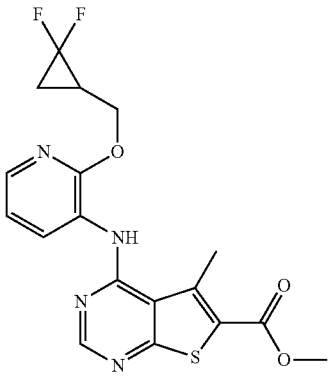 [SMILES: COC(=O)c1sc2ncnc(Nc3cccnc3OCC3CC3(F)F)c2c1C]

Prepared analogously to example 32.1 using 2-((2,2-Difluorocyclopropyl)methoxy)pyridin-3-amine (200 mg) and chloro-5-methyl-thieno[2,3-d]pyrimidine-6-carboxylic acid methyl ester (194 mg).

Yield: 57 mg
Retention time HPLC: 2.49 min
HPLC method: 004_CC_ZQ6

34.2 4-(2-((2,2-Difluorocyclopropyl)methoxy)pyridin-3-ylamino)-5-methyl-thieno[2,3-d]pyrimidine-6-carboxylic acid

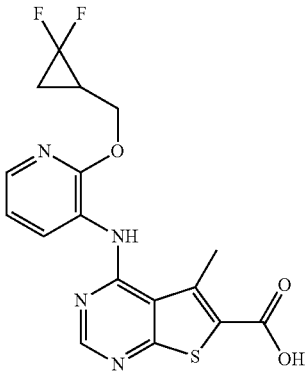 [SMILES: Cc1c(C(=O)O)sc2ncnc(Nc3cccnc3OCC3CC3(F)F)c12]

Prepared analogously to example 32 Step 2 using methyl 4-(2-((2,2-difluoro-cyclopropylmethoxy)pyridin-3-ylamino)-5-methylthieno[2,3-d]pyrimidine-6-carboxylate (56 mg)

Yield: 110 mg
Retention time HPLC: 2.37 min
HPLC method: 004_CC_ZQ6

34.3 4-(2-((2,2-Difluorocyclocrocyl)methoxy)pyridin-3-ylamino)-N-(3-(dimethylamino)propyl)-5-methyl-thieno[2,3-d]pyrimidine-6-carboxamide hydrochloride

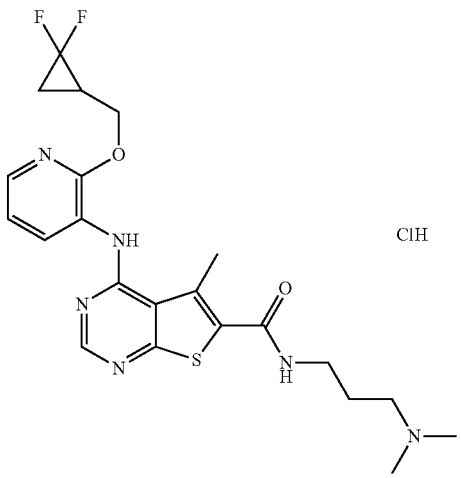 [SMILES: Cc1c(C(=O)NCCCN(C)C)sc2ncnc(Nc3cccnc3OCC3CC3(F)F)c12 ; Cl]

Prepared analogously to example 32.3 from 4-(2-(2,2)difluorocyclopropyl)-methoxy)pyridin-3-ylamino)-5-methylthieno[2,3-d]pyrimidine-6-carboxylic acid (27 mg) and N,N-dimethyl-1,3-propanediamine (11 mg).

Yield: 8.6 mg
ESI mass spectrum: m/z=477 (M+H)$^+$
Retention time HPLC: 1.83 min
HPLC method: 004_CC_ZQ6

Compound 34.4

Prepared analogously to example 32.3 using 4-(2-((2,2-difluorocyclopropyl)methoxy)pyridin-3-ylamino)-5-methylthieno[2,3-d]pyrimidine-6-carboxylic acid

| Structure | Name | Yield | Mass | Retention time | HPLC method |
|---|---|---|---|---|---|
|  | 4-(2-((2,2-difluorocyclopropyl)methoxy)-pyridin-3-ylamino)-5-methylthieno[2,3-d]pyrimidine-6-carboxamide | 4 mg | 392 | 2.19 | 004_CC_ZQ6 |

Compound 35

4-(2-Isopropoxypyridin-3-ylamino)-5-methylthieno[2,3-d]pyrimidine-6-carboxyamide

35.1 Methyl 4-(2-isopropoxypyridin-3-ylamino)-5-methyl-thieno[2,3-d]byrimidine-6-carboxylate

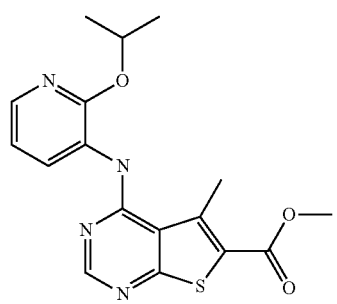 [SMILES: COC(=O)c1sc2ncnc(Nc3cccnc3OC(C)C)c2c1C]

2-Isopropoxypyridin-3-amine (1.3 g) was added to a solution of 4-Chloro-5-methyl-thieno[2,3-d]pyrimidine-6-carboxylic acid methyl ester (2.3 g), Xantphos (995.2 mg) and Cesium carbonate (3.9 g) in degassed dioxane (40 ml). The mixture was again degassed in a sonicator for 15 min before addition of $Pd_2(dba)_3$. The reaction mixture was then heated under a nitrogen atmosphere to 90° C. for 3 h. The mixture was cooled, filtered and the solid washed with dioxane. The residues were combined and poured into an ammonium hydroxide solution. The solid was filtered off to yield the desired product.

Yield: 2.05 g

35.2 4-(2-Isopropoxypyridin-3-ylamino)-5-methyl-thieno[2,3-d]pyrimidine-6-carboxylic acid

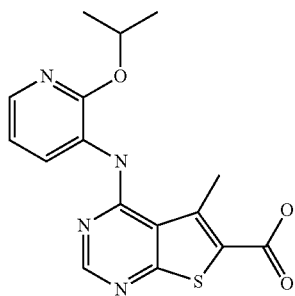 [SMILES: Cc1c(C(=O)O)sc2ncnc(Nc3cccnc3OC(C)C)c12]

Methyl 4-(2-isopropoxypyridin-3-ylamino)-5-methyl-thieno[2,3-d]pyrimidine-6-carboxylate (2.04 g) was dissolved in methanol (24.0 ml), NaOH (2M; 6.0 ml) was added and the mixture was stirred at 60° C. for 1 h. Then the reaction was cooled and washed with dichloromethane. The aqueous layer was acidified to pH 5 with conc. HCl and the precipitate was filtered and washed with water.

Yield: 1.5 g

ESI mass spectrum: m/z=345 (M+H)+

35.3 4-(2-Isopropoxypyridin-3-ylamino)-5-methyl-thieno[2,3-d]pyrimidine-6-carboxamide

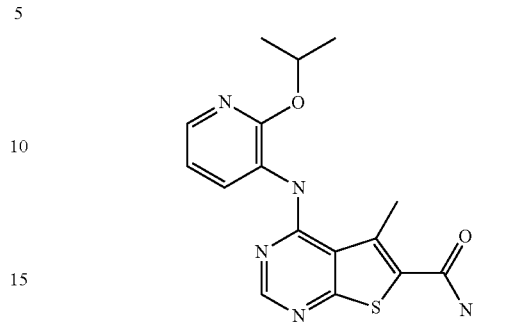

HATU (182.0 mg) was added to an ice cooled solution of 150 mg 4-(2-Isopropoxypyridin-3-ylamino)-5-methyl-thieno[2,3-d]pyrimidine-6-carboxylic acid and DIPEA (83.0 µl) in DMF (3.0 ml). The mixture was stirred at 0° C. for 20 min then ammonia/MeOH (7M; 1.5 ml) was added and it was allowed to warm to room temperature overnight. The mixture was diluted with EtOAc and washed with water, 2M NaOH and concentrated in vacuo. The residue was triturated with $Et_2O$ and filtered to give the title compound.

Yield: 90.0 mg

ESI mass spectrum: m/z=344 (M+H)+

Compound 36

N-(3-(Dimethylamino)propyl)-4-(2-isopropoxypyridin-3-ylamino)-5-methyl-thieno[2,3-d]pyrimidine-6-carboxamide

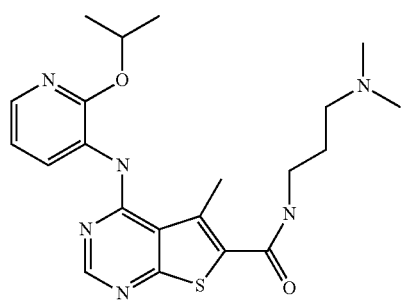 [SMILES: Cc1c(C(=O)NCCCN(C)C)sc2ncnc(Nc3cccnc3OC(C)C)c12]

Prepared analogously to example 1.3 using 4-(2-isopropoxypyridin-3-ylamino)-5-methylthieno[2,3-d]pyrimidine-6-carboxylic acid (descirbed in 1.2) and 3-dimethylaminopropylamine. The resultant product was purified by chromatography.

Yield: 68 mg

ESI mass spectrum: m/z=427 (M−H)

Further Analogues of 36

The compounds listed in the following table were synthesized analogously to example 1.3 using 4-(2-isopropoxypyridin-3-ylamino)-5-methylthieno[2,3-d]pyrimidine-6-carboxylic acid and the corresponding amine

TABLE 1

| | Structure | Name | Yield | Mass | Retention time | HPLC method |
|---|---|---|---|---|---|---|
| 36.1 | 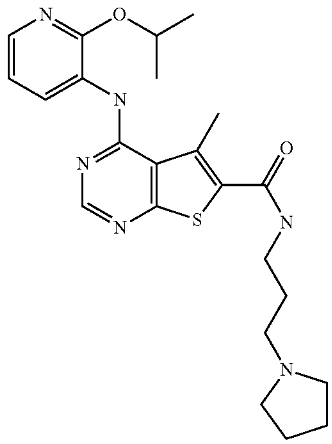 [SMILES: Cc1c(C(=O)NCCCN2CCCC2)sc2ncnc(Nc3cccnc3OC(C)C)c12] | 4-(2-Isopropoxypyridin-3-ylamino)-5-methyl-N-(3-(pyrrolidin-1-yl)propyl)thieno[2,3-d]pyrimidine-6-carboxamide | 15 mg | 455 | 1.52 | C_SF_TFA_MeOH_P30V#004_CC_ZQ1 |
| 36.2 | 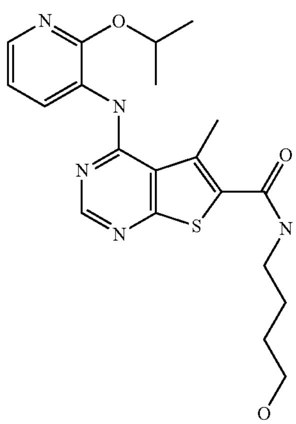 [SMILES: Cc1c(C(=O)NCCCCO)sc2ncnc(Nc3cccnc3OC(C)C)c12] | N-(4-Hydroxybutyl)-4-(2-isopropoxypyridin-3-ylamino)-5-methylthieno[2,3-d]pyrimidine-6-carboxamide | 11.4 mg | 416 | 1.92 | |
| 36.3 | 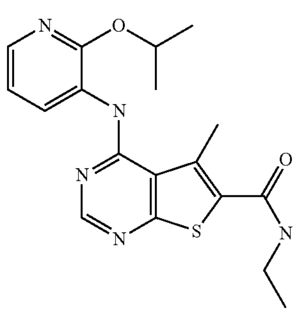 [SMILES: CCNC(=O)c1sc2ncnc(Nc3cccnc3OC(C)C)c2c1C] | N-Ethyl-4-(2-isopropoxypyridin-3-ylamino-5-methylthieno[2,3-d]pyrimidine-6-carboxamide | 14.8 mg | 372 | 1.99 | |

TABLE 1-continued

| | Structure | Name | Yield | Mass | Retention time | HPLC method |
|---|---|---|---|---|---|---|
| 36.4 | 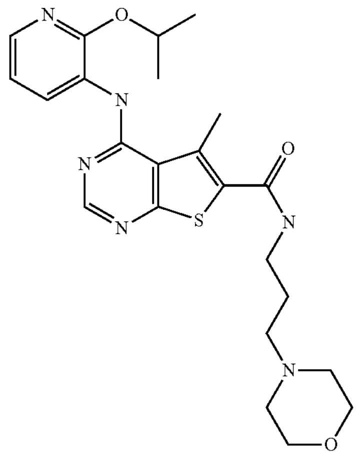 [SMILES: Cc1c(C(=O)NCCCN2CCOCC2)sc2ncnc(Nc3cccnc3OC(C)C)c12] | 4-(2-Isopropoxypyridin-3-ylamino)-5-methyl-N-morpholinopropyl)thieno[2,3-d]pyrimidine-6-carboxamide | 24.8 mg | 471 | 1.49 | |
| 36.5 | 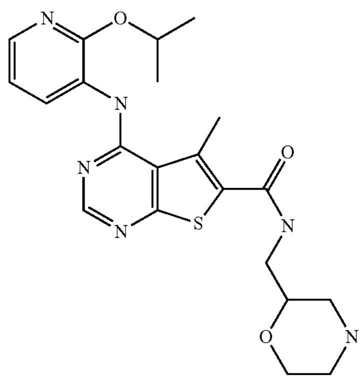 [SMILES: Cc1c(C(=O)NCC2CNCCO2)sc2ncnc(Nc3cccnc3OC(C)C)c12] | 4-(2-Isopropoxypyridin-3-ylamino)-5-methyl-N-(morpholin-2ylmethyl)thieno[2,3-d]pyrimidine-6-carboxamide | 31.4 mg | 433 | 1.5 | |
| 36.6 | 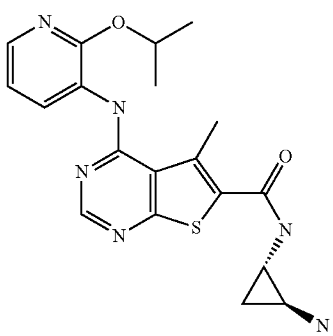 [SMILES: Cc1c(C(=O)N[C@H]2C[C@@H]2N)sc2ncnc(Nc3cccnc3OC(C)C)c12] | N-((1S,2S)-2-Aminocyclopropyl)-4-(2-isopropoxypyridin-3-ylamino)-5-methylthieno[2,3-d]pyrimidine-6-carboxamide | 18.4 mg | 399 | 1.5 | |
| 36.7 | 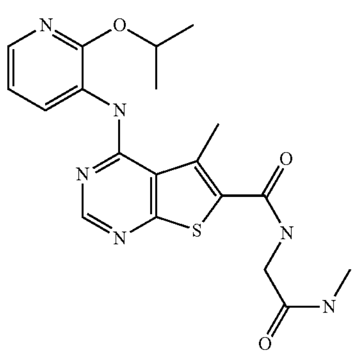 [SMILES: CNC(=O)CNC(=O)c1sc2ncnc(Nc3cccnc3OC(C)C)c2c1C] | 4-(2-Isopropoxypyridin-3ylamino)-5-methyl-N-(2-(methylamino)-2-oxoethyl)thieno[2,3-d]pyrimidine-6-carboxamide | 22.1 mg | 415 | 1.87 | |

TABLE 1-continued

| | Structure | Name | Yield | Mass | Retention time | HPLC method |
|---|---|---|---|---|---|---|
| 36.8 | 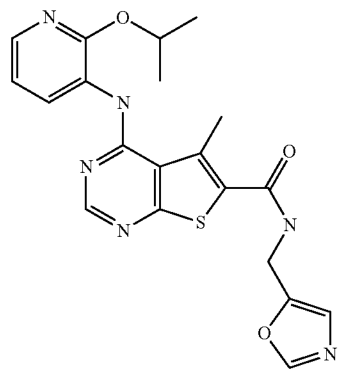 [SMILES: Cc1c(C(=O)NCc2cnco2)sc2ncnc(Nc3cccnc3OC(C)C)c12] | 4-(2-Isopropoxypyridin-3ylamino)-5-methyl-N-(oxazol-5-ylmethyl)thieno[2,3-d]pyrimidine-6-carboxamide | 16.4 mg | 425 | 1.93 | |
| 36.9 | 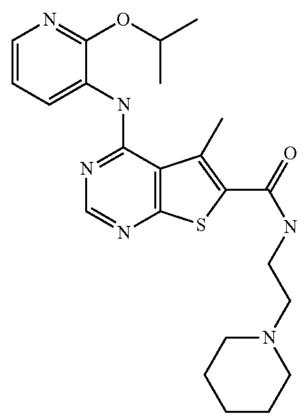 [SMILES: Cc1c(C(=O)NCCN2CCCCC2)sc2ncnc(Nc3cccnc3OC(C)C)c12] | 4-(2-Isopropoxypyridin-3ylamino)-5-methyl-N-(2-(piperidin-1-yl)ethyl)thieno[2,3-d]pyrimidine-6-carboxamide | 16.4 mg | 455 | 1.53 | |
| 36.10 | 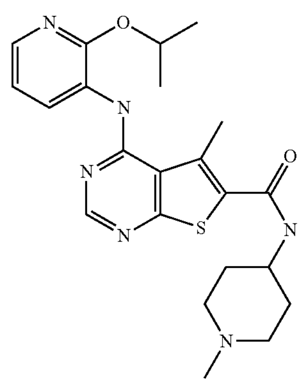 [SMILES: Cc1c(C(=O)NC2CCN(C)CC2)sc2ncnc(Nc3cccnc3OC(C)C)c12] | 4-(2-Isopropoxypyridin-3ylamino)-5-methyl-N-(1-methylpiperidin-4-yl)thieno[2,3-d]pyrimidine-6-carboxamide | 30.9 mg | 441 | 1.5 | |
| 36.11 | 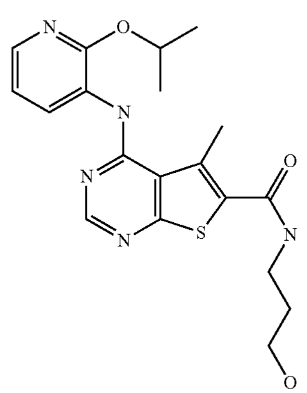 [SMILES: Cc1c(C(=O)NCCCO)sc2ncnc(Nc3cccnc3OC(C)C)c12] | N-(3-Hydroxypropyl)-4-(2-isopropoxypyridin-3ylamino)-5-methylthieno[2,3-d]pyrimidine-6-carboxamide | 13.7 mg | 402 | 1.9 | |

TABLE 1-continued

| | Structure | Name | Yield | Mass | Retention time | HPLC method |
|---|---|---|---|---|---|---|
| 36.12 | 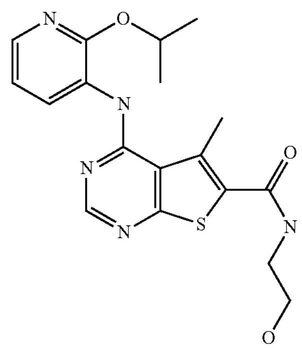 [SMILES: Cc1c(C(=O)NCCO)sc2ncnc(Nc3cccnc3OC(C)C)c12] | N-(2-Hydroxyethyl)-4-(2-isopropoxypyridin-3ylamino)-5-methylthieno[2,3-d]pyrimidine-6-carboxamide | 9 mg | 388 | 1.87 | |
| 36.13 | 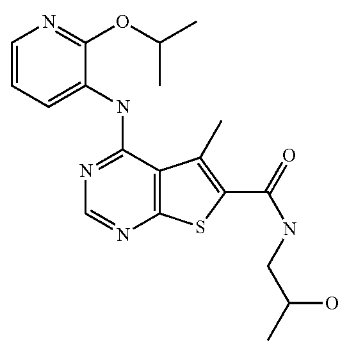 [SMILES: Cc1c(C(=O)NCC(C)O)sc2ncnc(Nc3cccnc3OC(C)C)c12] | N-(2-Hydroxypropyl)-4-(2-isopropoxypyridin-3ylamino)-5-methylthieno[2,3-d]pyrimidine-6-carboxamide | 19.1 mg | 402 | 1.92 | |
| 36.14 | 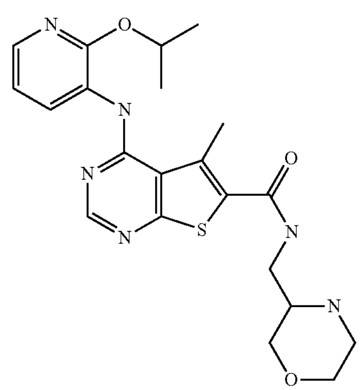 [SMILES: Cc1c(C(=O)NCC2COCCN2)sc2ncnc(Nc3cccnc3OC(C)C)c12] | 4-(2-Isopropoxypyridin-3ylamino)-5-methyl-N-(morpholin-3-ylmethyl)thieno[2,3-d]pyrimidine-6-carboxamide | 28.1 mg | 443 | 1.51 | |
| 36.15 | 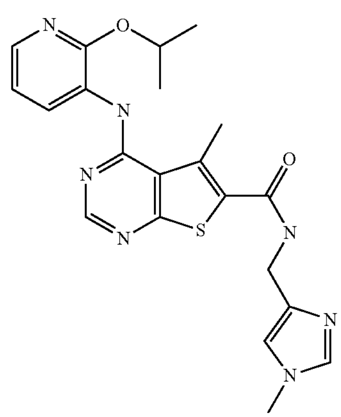 [SMILES: Cc1c(C(=O)NCc2cn(C)cn2)sc2ncnc(Nc3cccnc3OC(C)C)c12] | 4-(2-Isopropoxypyridin-3ylamino)-5-methyl-N-((1-methyl-1H-imidazol-4-yl)methyl)thieno[2,3-d]pyrimidine-6-carboxamide | 28.3 mg | 438 | 1.5 | |

TABLE 1-continued

| | Structure | Name | Yield | Mass | Retention time | HPLC method |
|---|---|---|---|---|---|---|
| 36.16 | 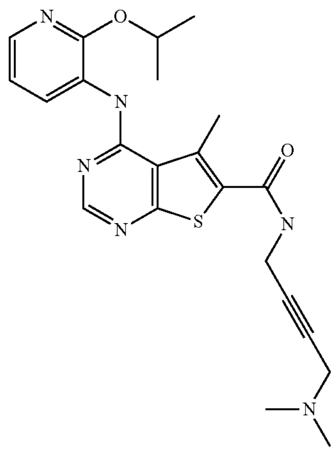 [SMILES: Cc1c(C(=O)NCC#CCN(C)C)sc2ncnc(Nc3cccnc3OC(C)C)c12] | N-(4-(Dimethylamino)-but-2-ynyl)-4-(2-isopropoxypyridin-3-ylamino)-5-methylthieno[]2,3-d]pyrimidine-6-carboxamide | 29.6 mg | 439 | 1.5 | |
| 36.17 | 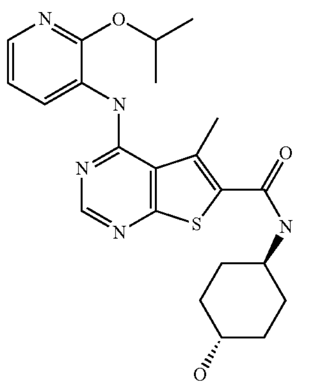 [SMILES: Cc1c(C(=O)N[C@H]2CC[C@H](O)CC2)sc2ncnc(Nc3cccnc3OC(C)C)c12] | N-((trans)-4-Hydroxycyclohexyl)-4-(2-isopropoxy-pyridin-3-ylamino)-5-methylthieno[2,3-d]pyrimidine-6-carboxyamide | 17.7 mg | 442 | 1.94 | |
| 36.18 | 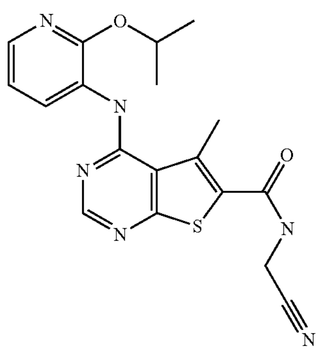 [SMILES: Cc1c(C(=O)NCC#N)sc2ncnc(Nc3cccnc3OC(C)C)c12] | N-(Cyanomethyl)-4-(2-isopropoxy-pyridin-3-ylamino)-5-methylthieno[2,3-d]pyrimidine-6-carboxyamide | 19.1 mg | 383 | 1.93 | |
| 36.19 | 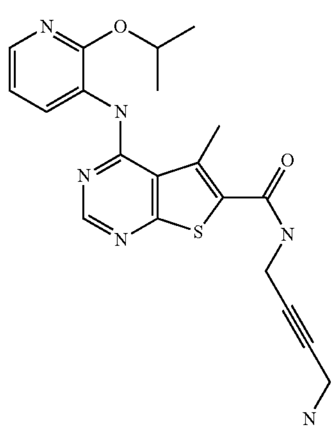 [SMILES: Cc1c(C(=O)NCC#CCN)sc2ncnc(Nc3cccnc3OC(C)C)c12] | N-(4-Aminobut-2-ynyl)-4-(2-isopropoxypyridin-3-ylamino)-5-methylthieno[2,3-d]pyrimidine-6-carboxyamide | 23.4 mg | 411 | 1.51 | |

Compound 37

4-(4-Fluoro-2-isopropoxyphenylamino)-5-methyl-thieno[2,3-d]pyrimidine-6-carboxylic acid

37.1 Methyl 4-(4-fluoro-2-isopropoxyphenylamino)-5-methyl-thieno[2,3-d]pyrimidine-6-carboxylate

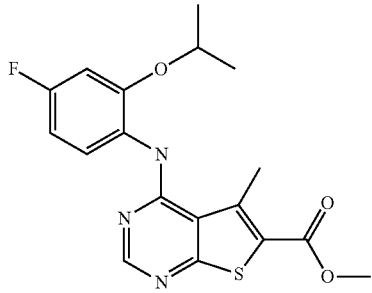 [SMILES: COC(=O)c1sc2ncnc(Nc3ccc(F)cc3OC(C)C)c2c1C]

4-Chloro-5-methyl-thieno[2,3-d]pyrimidine-6-carboxylic acid methyl ester (112 mg), 4-fluoro-2-isopropoxyaniline (77.9 mg) and p-toluenesulfonic acid monohydrate (15 mg) were dissolved in dioxane (3.0 ml). The reaction was heated at 110° C. under microwave irradiation. Then the reaction mixture was concentrated in vacuo and the residue was dissolved in dichloromethane and extracted with water. The organic phase was dried and concentrated in vacuo. The residue was triturated with diisopropyl ether and filtered.

Yield: 106 mg
ESI mass spectrum: m/z=376 (M+H)$^+$
Retention time HPLC: 4.22 min
HPLC method: AC 1

37.2 4-(4-Fluoro-2-isopropoxyphenylamino)-5-methyl-thieno[2,3-d]pyrimidine-6-carboxylic acid

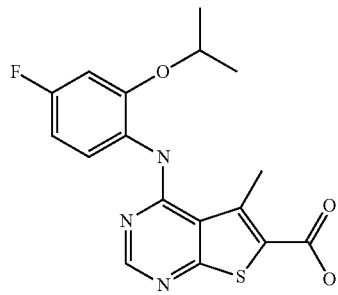 [SMILES: Cc1c(C(=O)O)sc2ncnc(Nc3ccc(F)cc3OC(C)C)c12]

Methyl 4-(4-fluoro-2-isopropoxyphenylamino)-5-methyl-thieno[2,3-d]pyrimidine-6-carboxylate (451 mg) and lithium hydroxide (865 mg) was dissolved in a mixture of THF:methanol:water (1:1:1; 100 ml) and was stirred at room temperatruer overnight. Then the mixture was acidified with conc. HCl, the resultant precipitate was filtered, dried and triturated with diisopropyl ether to afford the title compound.

Yield: 378 mg
ESI mass spectrum: m/z=362 (M+H)$^+$
Retention time HPLC: 2.72 min
HPLC method: AC 1

Compound 38

4-(4-Fluoro-2-isopropoxyphenylamino)-5-methyl-thieno[2,3-d]pyrimidine-6-carboxylic acid (3-dimethylamino-propyl)-amide

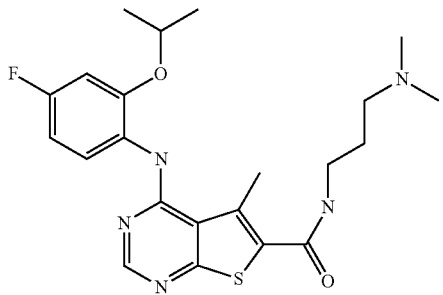 [SMILES: Cc1c(C(=O)NCCCN(C)C)sc2ncnc(Nc3ccc(F)cc3OC(C)C)c12]

Prepared analogously to example 35.3 using 4-(4-Fluoro-2 isopropoxyphenylamino) 5-methyl-thieno[2,3-d]pyrimidine-6-carboxylic acid (descirbed in 37.2) and N,N-Dimetyhl-1,3-propanediamine.

Yield: 355 mg
ESI mass spectrum: m/z=446 (M+H)$^+$
Retention time HPLC: 2.72 min
HPLC method: WO01 001

Compound 39

4-[2-(1-Ethylcarbamoyl-ethoxy)-4-fluoro-phenylamino]-5-methyl-thieno[2,3-d]pyrimidine-6-carboxylic acid

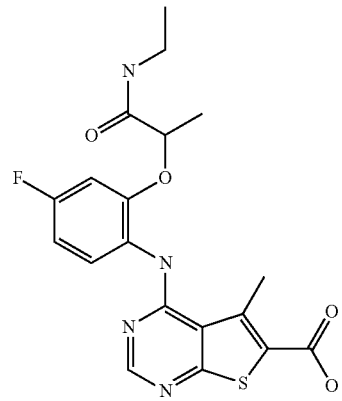 [SMILES: CCNC(=O)C(C)Oc1cc(F)ccc1Nc1ncnc2sc(C(=O)O)c(C)c12]

To the intermediate XVIII (0.36 g) in THF:methanol 1:1 (20 ml) was added sodium hydroxide 1M (2.00 ml) and stirred at 50° C. overnight. Then the mixture was acidified by addition of hydrochloric acid and concentrated. The residue was diluted with water, filtrated and the solid was washed with diethylether.

Yield: 0.30 g
ESI mass spectrum: m/z=419 (M+H)$^+$
Retention time HPLC: 2.65 min
HPLC method: A_4

125

Compound 40

4-[2-(1-Ethylcarbamoyl-ethoxy)-4-fluoro-phenylamino]-5-methyl-thieno[2,3-d]pyrimidine-6-carboxylic acid (3-dimethylamino-propyl)-amide

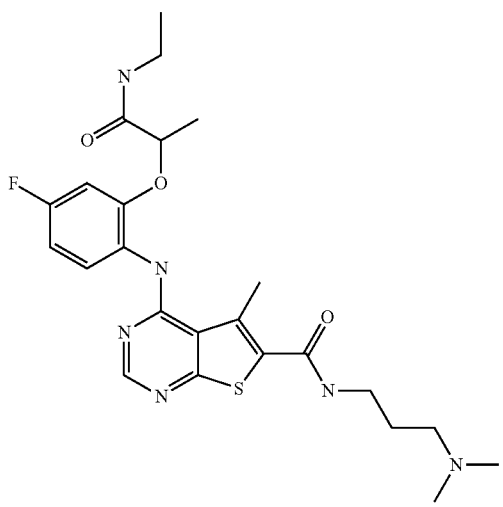 [SMILES: CCNC(=O)C(C)Oc1cc(F)ccc1Nc1ncnc2sc(C(=O)NCCCN(C)C)c(C)c12]

Prepared analogously to example 5 using 4-[2-(1-ethylcarbamoyl-ethoxy)-4-fluoro-phenylamino]-5-methyl-thieno[2,3-d]pyrimidine-6-carboxylic acid (60 mg) and N,N-dimethyl-1,3-propanediamine (24 µl).

Yield: 0.32 g
ESI mass spectrum: m/z=503 (M+H)$^+$
Retention time HPLC: 1.97 min
HPLC method: A_4

Compound 41

The compound listed in the following table was synthesized analogously to example 40 using 4-[2-(1-ethylcarbamoyl-ethoxy)-4-fluoro-phenylamino]-5-methyl-thieno[2,3-d]pyrimidine-6-carboxylic acid (compound 39) and ethanolamine.

126

Compound 42

4-[2-(3-Amino-1-methyl-propoxy)-3pyridin-3-ylamino]-5-methyl-thieno[2,3-d]pyrimidine-6-carboxylic acid (2-hydroxy-ethyl)-amide

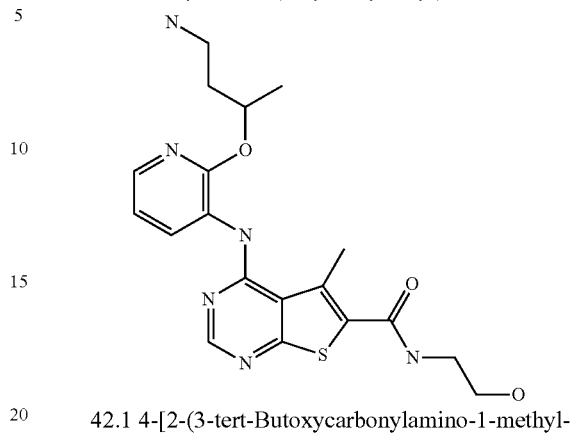

42.1 4-[2-(3-tert-Butoxycarbonylamino-1-methyl-propoxy)-pyridin-3-ylamino]5-methyl-thieno[2,3-d]pyrimidine-6-carboxylic acid

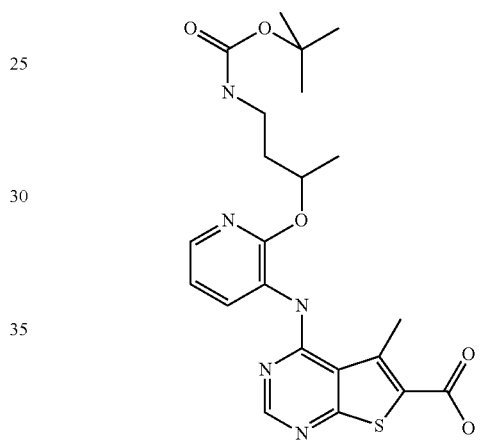

To the product from 16.1 (0.20 g) in DMF (5 ml) was added CDI (75 mg) and stirred for 2 hours at 70° C. Then 2-aminoethanol (28.8 µl) was added and stirred at rt overnight. The reaction mixture was concentrated. Purification was achieved by chromatography.

| Structure | Name | Yield | Mass | Retention time | HPLC method |
|---|---|---|---|---|---|
| 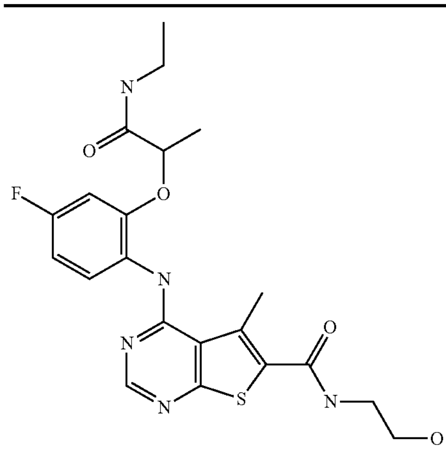 | 4-[2-(1-Ethylcarbamoyl-ethoxy)-4-fluoro-phenylamino]-5-methyl-thieno[2,3-d]pyrimidine-6-carboxylic acid(2-hydroxy-ethyl)-amide | 25 mg | 462 | 2.33 | A_4 |

Yield: 0.16 g
ESI mass spectrum: m/z=417 (M+H)+
Retention time HPLC: 2.18 min
HPLC method: A_10

Compound 43

4-[2-(3-Methanesulfonylamino-1-methyl-propoxy)-pyridin-3-ylamino]-5-methyl-thieno[2,3-d]pyrimidine-6-carboxylic acid (2-hydroxy-ethyl)-amide

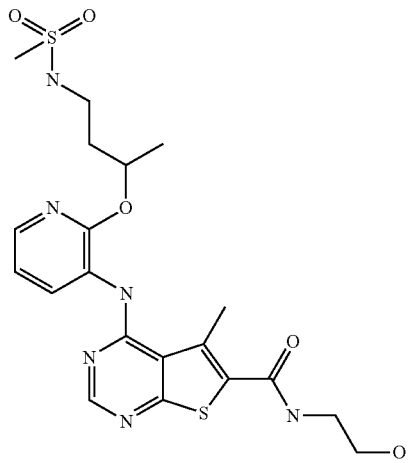 [SMILES: Cc1c(C(=O)NCCO)sc2ncnc(Nc3cccnc3OC(C)CCNS(C)(=O)=O)c12]

Methanesulfonyl chloride (19 µl) was added to a mixture of the product from example 42 (0.11 g), DCM (5 ml) and DBU (75 µl). The mixture was stirred at rt overnight. The reaction mixture was concentrated and then purified by chromatography.
Yield: 9.8 mg
ESI mass spectrum: m/z=495 (M+H)+
Retention time HPLC: 2.38 min
HPLC method: AC 1

Compound 44

4-[2-(3-Methanesulfonylamino-1-methyl-propoxy)-pyridin-3-ylamino]-5-methyl-thieno[2,3-d]pyrimidine-6-carboxylic acid

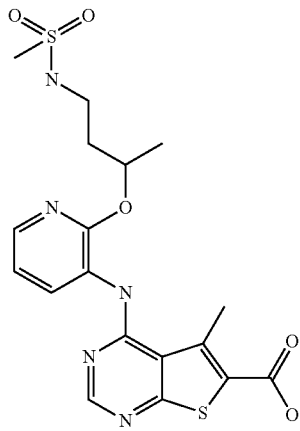

44.1 4-[2-(3-Methanesulfonylamino-1-methyl-propoxy)-pyridin-3-ylamino]-5-methyl-thieno[2,3-d]pyrimidine-6-carboxylic acid methyl ester

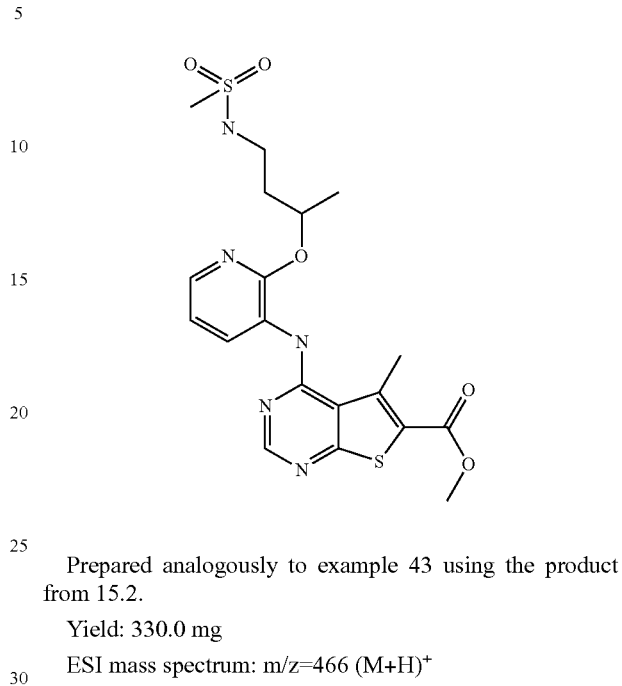

Prepared analogously to example 43 using the product from 15.2.
Yield: 330.0 mg
ESI mass spectrum: m/z=466 (M+H)+

44.2 4-[2-(3-Methanesulfonylamino-1-methyl-propoxy)-pyridin-3-ylamino]-5-methyl-thieno[2,3-d]pyrimidine-6-carboxylic acid

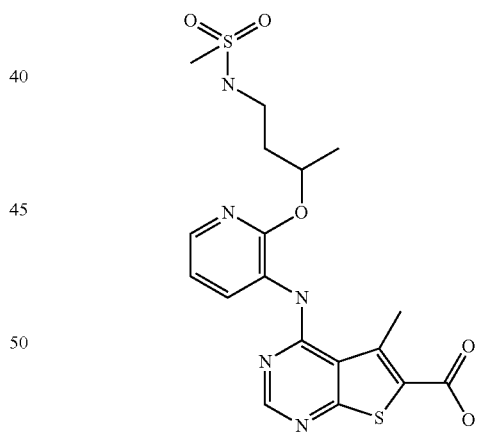

Sodium hydroxid 1M (3 ml) was added to a mixture of the product from example 44.1 (0.27 g) and MeOH (5 ml). The mixture was stirred at 50° C. for 1 hour. Then the reaction mixture was neutralized with hydrochloric acid 1M (3 ml) and concentrated. The residue was diluted with water and extracted with DCM. The organic layer was washed with a sodium chloride solution, dried and concentrated.
Yield: 210.0 mg
ESI mass spectrum: m/z=452 (M+H)+
Retention time HPLC: 1.62 min
HPLC method: A_10

Compound 45

4-[2-(3-Methanesulfonylamino-1-methyl-propoxy)-pyridin-3-ylamino]-5-methyl-thieno[2,3-d]pyrimidine-6-carboxylic acid amide

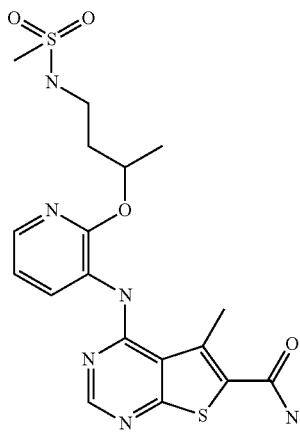 [SMILES: Cc1c(C(N)=O)sc2ncnc(Nc3cccnc3OC(C)CCNS(C)(=O)=O)c12]

A reaction mixture of the product from example 44.2 (50 mg), TBTU (36 mg), DIPEA (39 µl), ammonia 0.5M in THF (222 µl), THF (3 ml) was stirred at rt for 1 hour. Then the mixture was concentrated and then purified by chromatography.
Yield: 18.0 mg
ESI mass spectrum: m/z=451 (M+H)$^+$
Retention time HPLC: 1.46 min
HPLC method: A_10

Compound 46

4-[2-(3-Methanesulfonylamino-1-methyl-propoxy)-pyridin-3-ylamino]-5-methyl-thieno[2,3-d]pyrimidine-6-carboxylic acid (3-dimethylamino-propyl)-amide

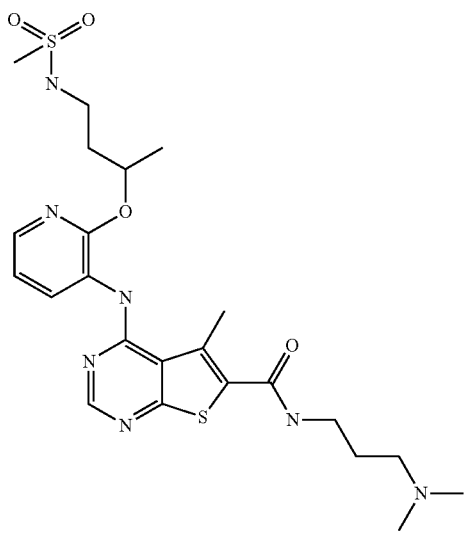 [SMILES: Cc1c(C(=O)NCCCN(C)C)sc2ncnc(Nc3cccnc3OC(C)CCNS(C)(=O)=O)c12]

Prepared analogously to example 45 using the product from 44.2.
Yield: 62.0 mg
ESI mass spectrum: m/z=536 (M+H)$^+$
Retention time HPLC: 1.14 min
HPLC method: A_10

Compound 47

Methyl 4-[4-cyano-2-(2-fluoro-1-fluoromethyl-ethoxy)phenylamino]-5-methyl-thieno[2,3-d]pyrimidine-6-carboxylate

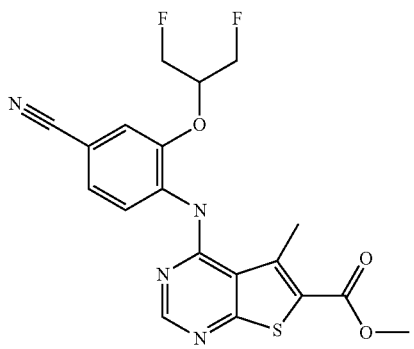 [SMILES: COC(=O)c1sc2ncnc(Nc3ccc(C#N)cc3OC(CF)CF)c2c1C]

4-Chloro-5-methyl-thieno[2,3-d]pyrimidine-6-carboxylic acid methyl ester (0.2 g), 4-amino-3-(2-fluoro-1-fluoromethyl-ethoxy)-benzonitrile (0.17 g), p-toluenesulfonic acid monohydrate (0.16 g) and isopropanol (3.0 ml) were stirred at 90° C. for 2 hours. Then the mixture was poured in water and filtrated. The solid was washed with water and dried in an oven at 70° C.
Yield: 160.0 mg
ESI mass spectrum: m/z=419 (M+H)$^+$
Retention time HPLC: 2.05 min
HPLC method: AC 1

Compound 48

4-[4-Cyano-2-(2-fluoro-1-fluoromethyl-ethoxy)-phenylamino]-5-methyl-thieno[2,3-d]pyrimidine-6-carboxylic acid (3-pyrrolidin-1-yl-propyl)-amide

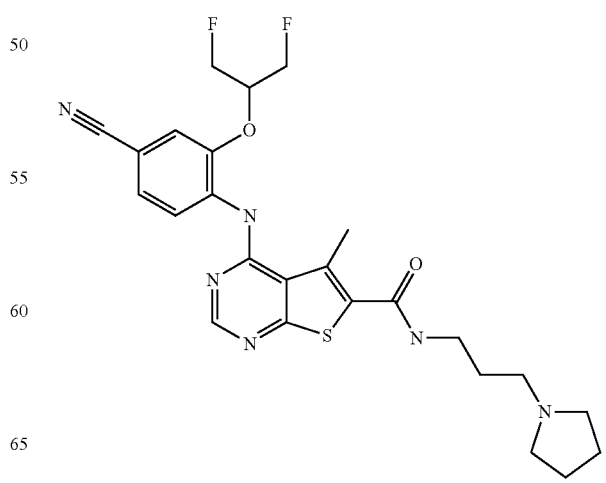

48.1 4-[4-Cyano-2-(2-fluoro-1-fluoromethyl-ethoxy)-phenylamino]-5-methyl-thieno[-2,3-d]pyrimidine-6-carboxylic acid

48.2 4-[4-Cyano-2-(2-fluoro-1-fluoromethyl-ethoxy)-phenylamino]-5-methyl-thieno[2,3-d]pyrimidine-6-carboxylic acid (3-pyrrolidin-1-yl-propyl)-amide

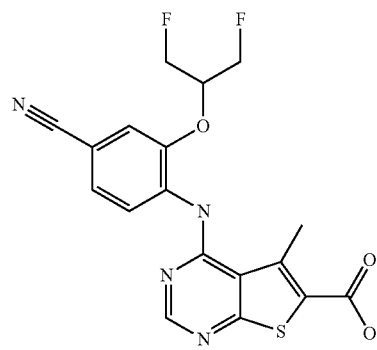 [SMILES: Cc1c(C(=O)O)sc2ncnc(Nc3ccc(C#N)cc3OC(CF)CF)c12]

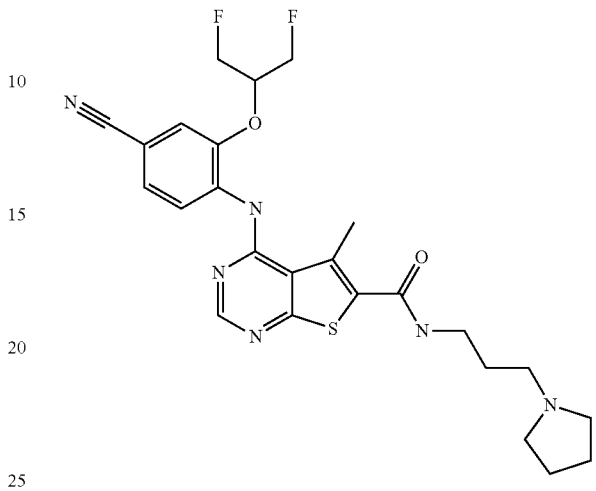

The product from example 47 (1.4 g) was dissolved in THF (200 ml). 10 ml water and LiOH (0.48 g) were added. The mixture was stirred at rt for 4 days. Then the mixture was acidified with 10% citric acid and concentrated. The residue was dried in an oven at 70° C.

Yield: 950.0 mg

4-[4-Cyano-2-(2-fluoro-1-fluoromethyl-ethoxy)-phenylamino]-5-methyl-thieno[2,3-d]pyrimidine-6-carboxylic acid (100 mg), HATU (114 mg) and TEA (52 µl) were dissolved in DMF (4 ml). N,N-dimethyl-1,3-propanediamine (31 µl) was added. The mixture was stirred for 1 hour at rt. Then the mixture was poured in water and filtrated. The solid was washed with water and dried in an oven at 70° C.

Yield: 75.0 mg
ESI mass spectrum: m/z=515 (M+H)$^+$
Retention time HPLC: 1.95 min
HPLC method: AC 1

The following compounds were prepared analogously to example 48.2 using 4-[4-cyano-2-(2-fluoro-1-fluoromethyl-ethoxy)-phenylamino]-5-methyl-thieno[2,3-d]pyrimidine-6-carboxylic acid and the corresponding amine.

| | Structure | Name | Yield | Mass | Retention time | HPLC method | Amine |
|---|---|---|---|---|---|---|---|
| 49 | ![structure] | 4-(4-Cyano-2-(2-fluoro-1-fluoromethyl-ethoxy)-phenylamino]-5-methyl-thieno[2,3-d]pyrimidine-6-carboxylic acid (3-dimethylamino-propyl)-amide | 30 mg | 489 | 1.9 | AC 1 | ![amine] |

| | Structure | Name | Yield | Mass | Retention time | HPLC method | Amine |
|---|---|---|---|---|---|---|---|
| 50 | 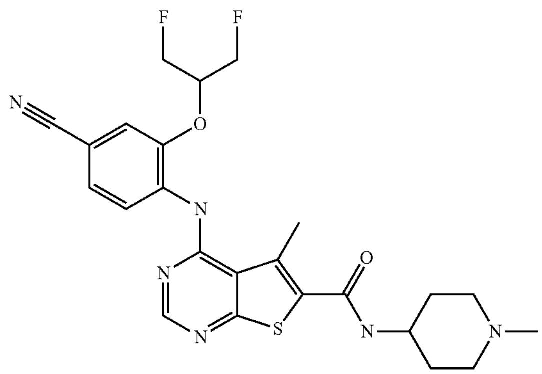 [SMILES: Cc1c(C(=O)NC2CCN(C)CC2)sc2ncnc(Nc3ccc(C#N)cc3OC(CF)CF)c12] | 4-(4-Cyano-2-(2-fluoro-1-fluoromethyl-ethoxy)-phenylamino]-5-methyl-thieno[2,3-d]pyrimidine-6-carboxylic acid (1-methyl-piperidin-4-yl)-amide | 40 mg | 501 | 1.95 | AC 1 | |
| 51 | 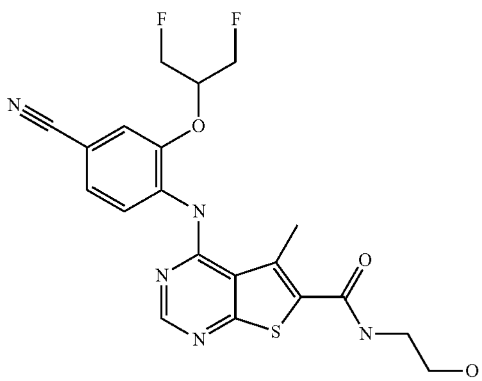 [SMILES: Cc1c(C(=O)NCCO)sc2ncnc(Nc3ccc(C#N)cc3OC(CF)CF)c12] | 4-(4-Cyano-2-(2-fluoro-1-fluoromethyl-ethoxy)-phenylamino]-5-methyl-thieno[2,3-d]pyrimidine-6-carboxylic acid (2-hydroxy-ethyl)-amide | 60 mg | 448 | 2.21 | AC 1 | |
| 52 | 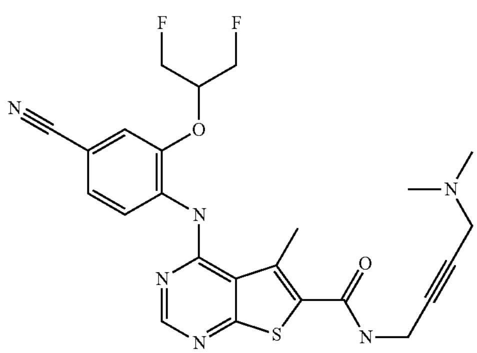 [SMILES: Cc1c(C(=O)NCC#CCN(C)C)sc2ncnc(Nc3ccc(C#N)cc3OC(CF)CF)c12] | 4-(4-Cyano-2-(2-fluoro-1-fluoromethyl-ethoxy)-phenylamino]-5-methyl-thieno[2,3-d]pyrimidine-6-carboxylic acid (4-dimethylamino-but-2-ynyl)-amide | 50 mg | 499 | 1.87 | AC 1 | |
| 53 | 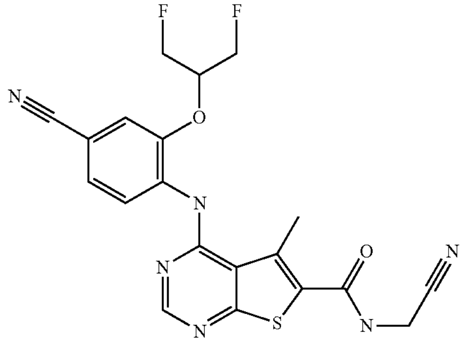 [SMILES: Cc1c(C(=O)NCC#N)sc2ncnc(Nc3ccc(C#N)cc3OC(CF)CF)c12] | 4-(4-Cyano-2-(2-fluoro-1-fluoromethyl-ethoxy)-phenylamino]-5-methyl-thieno[2,3-d]pyrimidine-6-carboxylic acid cyanomethyl-amide | 35 mg | 443 | 1.99 | AC 1 | |

Compound 54

4-[2-Cyano-methyl-methoxy)-4-fluoro-phenylamino]-5-methyl-thieno[2,3-d]pyrimidine-6-carboxylic acid amide

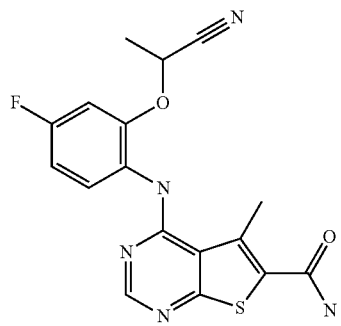 [SMILES: Cc1c(C(N)=O)sc2ncnc(Nc3ccc(F)cc3OC(C)C#N)c12]

54.1 4-(4-Fluoro-2-hydroxy-phenylamino)-5-methyl-thieno[2,3-d]pyrimidine-6-carboxylic acid

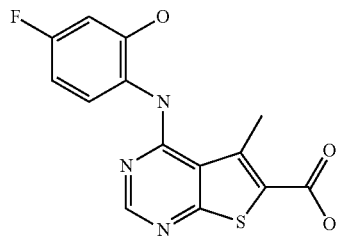 [SMILES: Cc1c(C(N)=O)sc2ncnc(Nc3ccc(F)cc3O)c12]

Methyl 4-(4-fluoro-2-hydroxyphenylamino)-5-methyl-thieno[2,3-d]pyrimidine-6-carboxylate (Intermediate III) (1.0 g), sodium hydroxide 1M (10 ml), methanol (20 ml) and THF (20 ml) were stirred at rt overnight. The mixture was concentrated and diluted with EE and water. The aqueous layer was acidified with hydrochloric acid and filtrated.

Yield: 800 mg
ESI mass spectrum: m/z=320 (M+H)⁺
Retention time HPLC: 2.22 min
HPLC method: 004_CC_ZQ6

54.2 4-(4-Fluoro-2-hydroxy-phenylamino)-5-methyl-thieno[2,3-d]pyrimidine-6-carboxylic acid amide

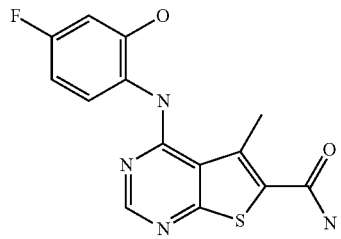

Prepared analogously to example 21.3 using the product from 66.1

Yield: 30 mg
ESI mass spectrum: m/z=319 (M+H)⁺
Retention time HPLC: 1.9 min
HPLC method: 004_CC_ZQ6

54.3 4-[2-Cyano-methyl-methoxy)-4-fluoro-phenylamino]-5-methyl-thieno[2,3-d]pyrimidine-6-carboxylic acid amide

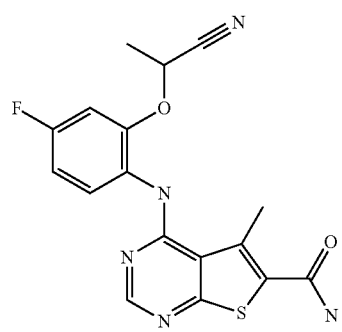

The product from 54.2 (30 mg), 2-bromopropionitrile (13 mg), cesium carbonate (40 mg) in DMF (1 ml) were stirred at rt overnight. The mixture was filtrated and the solid was washed with DMF. Water was added to the filtrate. The solid was isolated by filtration. The combined solids were freeze-dried.

Yield: 14 mg
ESI mass spectrum: m/z=372 (M+H)⁺
Retention time HPLC: 1.92 min
HPLC method: 004_CC_ZQ6

Compound 55

4-[2-(1-Carboxy-ethoxy)-4-fluoro-phenylamino]-5-methyl-thieno[2,3-d]pyrimidine-6-carboxylic acid methyl ester

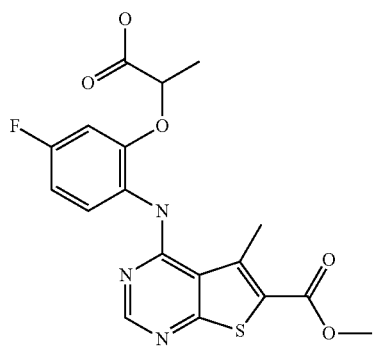 [SMILES: COC(=O)c1sc2ncnc(Nc3ccc(F)cc3OC(C)C(=O)O)c2c1C]

55.1 4-[2-(1-tert-Butoxycarbonyl-ethoxy)-4-fluoro-phenylamino]-5-methyl-thieno[2,3-d]pyrimidine-6-carboxylic acid methyl ester

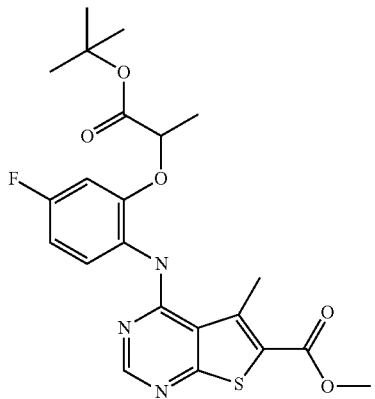 [SMILES: COC(=O)c1sc2ncnc(Nc3ccc(F)cc3OC(C)C(=O)OC(C)(C)C)c2c1C]

2-Bromopropionic acid tert-butyl-ester (1.4 g) was added to methyl 4-(4-fluoro-2-hydroxyphenylamino)-5-methyl-thieno[2,3-d]pyrimidine-6-carboxylate (Intermediate III) (2.00 g) and cesium carbonate (4.8 g) in ACN (50 ml) and stirred at 60° C. for 2 hours. The mixture was diluted with water, filtrated and washed with water.

Yield: 2.1 g

ESI mass spectrum: m/z=462 (M+H)$^+$

Retention time HPLC: 2.12 min

HPLC method: A_9

55.2 4-[2-(1-Carboxy-ethoxy)-4-fluoro-phenylamino]-5-methyl-thieno[2,3-d]pyrimidine-6-carboxylic acid methyl ester

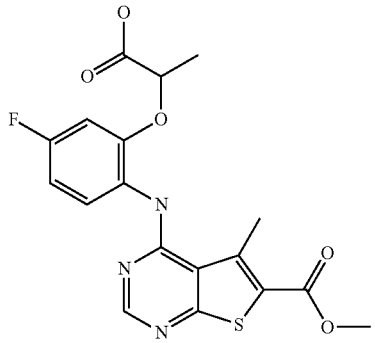 [SMILES: COC(=O)c1sc2ncnc(Nc3ccc(F)cc3OC(C)C(=O)O)c2c1C]

A mixture of the product from 55.1 (2.1 g) and 50% trifluoroacetic acid in DCM was stirred at rt overnight. Then the mixture was concentrated and the residue was triturated with diethylether.

Yield: 1.9 g

ESI mass spectrum: m/z=406 (M+H)$^+$

Retention time HPLC: 1.96 min

HPLC method: A_9

Compound 56
4-{2-[1-(3-Amino-propylcarbamoyl)-ethoxy]-4-fluoro-phenylamino}-5-methyl-thieno[2,3-d]pyrimidine-6-carboxylic acid methyl ester

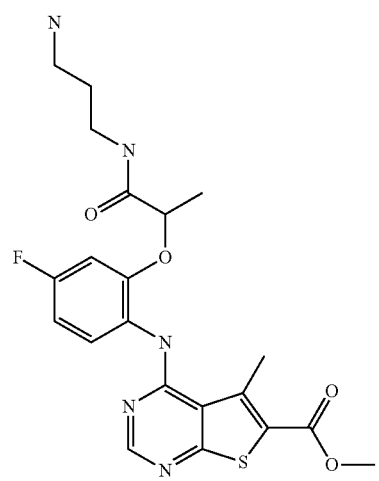 [SMILES: COC(=O)c1sc2ncnc(Nc3ccc(F)cc3OC(C)C(=O)NCCCN)c2c1C]

56.1 4-{2-[1-(3-tert-Butoxycarbonylamino-propylcarbamoyl)-ethoxy]-4-fluoro-phenylamino}-5-methyl-thieno[2,3-d]pyrimidine-6-carboxylic acid methyl ester

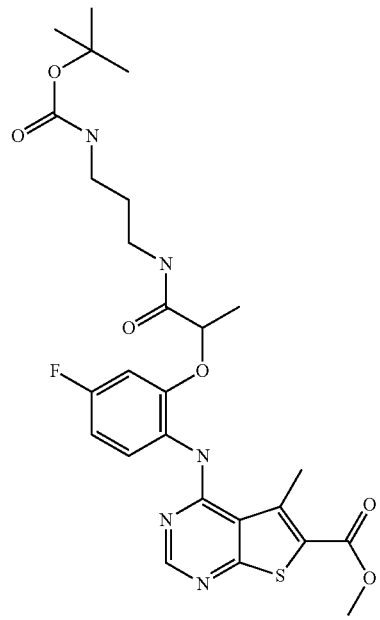 [SMILES: COC(=O)c1sc2ncnc(Nc3ccc(F)cc3OC(C)C(=O)NCCCNC(=O)OC(C)(C)C)c2c1C]

The product from 55 (170 mg) and TBTU (150 mg) was dissolved in ACN (5 ml). TEA (150 µl) was added to the mixture. The mixture was stirred for 15 min. at rt. Then tert-butyl N-(3-Aminopropyl)carbamate (200 mg) was added. The mixture was stirred at 50° C. for 2 days. Afterwards the mixture was diluted with water and filtrated. The solid was washed with water and dried in an oven Yield: 176 mg ESI mass spectrum: m/z=562 (M+H)$^+$ Retention time HPLC: 2.21 min HPLC method: A_9

56.2 4-{2-[1-(3-Amino-propylcarbamoyl)-ethoxy]-4-fluoro-phenylamino}-5-methyl-thieno[2,3-d]pyrimidine-6-carboxylic acid methyl ester

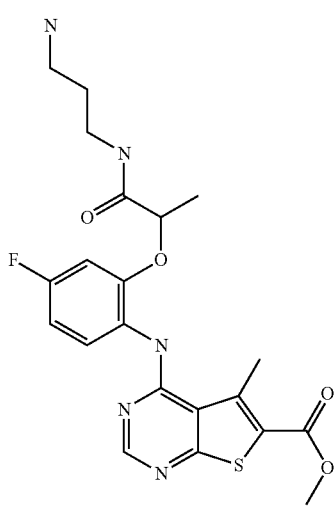 [SMILES: COC(=O)c1sc2ncnc(Nc3ccc(F)cc3OC(C)C(=O)NCCCN)c2c1C]

A mixture of the product from 56.1 (30 mg) and 25% trifluoroacetic acid in DCM (2 ml) was stirred at rt for 4 hours. The mixture was concentrated.

Yield: 25 mg

ESI mass spectrum: m/z=462 (M+H)$^+$

HPLC method: A_9

Compound 57

4-{2-[1-(3-Amino-propylcarbamoyl)-ethoxy]-4-fluoro-phenylamino}-5-methyl-thieno[2,3-d]pyrimidine-6-carboxylic acid (2-hydroxy-ethyl)-amide

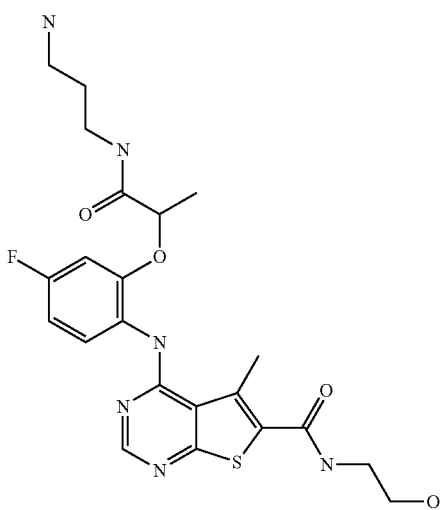 [SMILES: Cc1c(C(=O)NCCO)sc2ncnc(Nc3ccc(F)cc3OC(C)C(=O)NCCCN)c12]

57.1 4-{2-[1-(3-tert-Butoxycarbonylamino-propyl-carbamoyl)-ethoxy]-4-fluoro-phenylamino}-5-methyl-thieno[2,3-d]pyrimidine-6-carboxylic acid

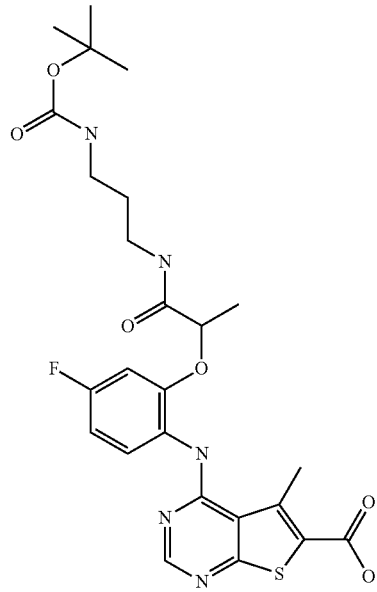 [SMILES: Cc1c(C(=O)O)sc2ncnc(Nc3ccc(F)cc3OC(C)C(=O)NCCCNC(=O)OC(C)(C)C)c12]

To the product from 55 (130 mg) in THF:MeOH=1:1 (5 ml) was added sodium hydroxide solution 1M (580 μl) and stirred at 40° C. overnight. The mixture was cooled down to rt and added Hydrochloric acid 1M (580 ml). Then the methanol was concentrated and the residue with DCM diluted. The organic layer was seperated by a cartridge and concentrated. The residue was triturated with diethylether.

Yield: 113 mg

57.2 4-{2-[1-(3-Amino-propylcarbamoyl)-ethoxy]-4-fluoro-phenylamino}-5-methyl-thieno[2,3-d]pyrimidine-6-carboxylic acid (2-hydroxy-ethyl)-amide

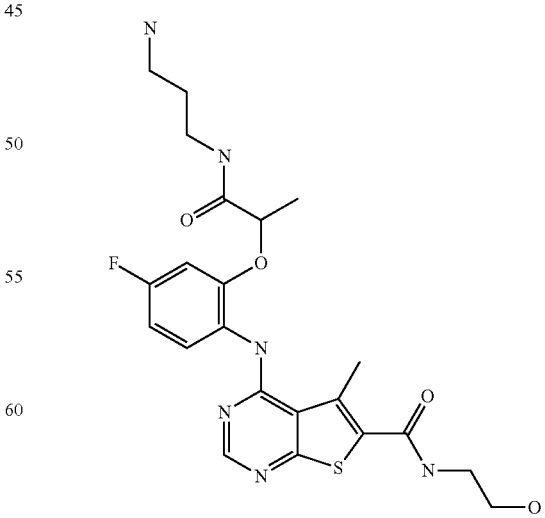

The product from 57.1 (115 mg) and TBTU (70 mg) were dissolved in DMF (1.5 ml). TEA (75 μl) was added and the mixture was stirred for 5 min. at rt. Ethanolamine (20 μl) was added and the mixture was stirred at rt overnight. Afterwards the mixture was diluted with methanol. Purification was achieved by chromatography. The combined fractions were concentrated. A mixture of DCM:TFA=50:50 was added to the residue and the mixture was stirred at rt for 1 hour. Then the mixture was concentrated. A solution of hydrochloric acid in methanol was added and the mixture was concentrated.

Yield: 70 mg
ESI mass spectrum: m/z=491 (M+H)⁺
Retention time HPLC: 1.92 min
HPLC method: A_9

Compound 58

4-{2-[1-(2-Amino-ethylcarbamoyl)-ethoxyl]-4-fluoro-phenylamino}-5-methyl-thieno[2,3-d]pyrimidine-6-carboxylic acid methyl ester

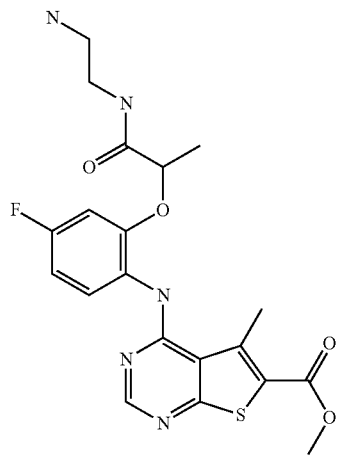 [SMILES: COC(=O)c1sc2ncnc(Nc3ccc(F)cc3OC(C)C(=O)NCCN)c2c1C]

58.1 4-{2-[1-(2-tert-Butoxycarbonylamino-ethylcarbamoyl)-ethoxy]-4-fluoro-phenylamino}-5-methyl-thieno[2,3-d]pyrimidine-6-carboxylic acid methyl ester

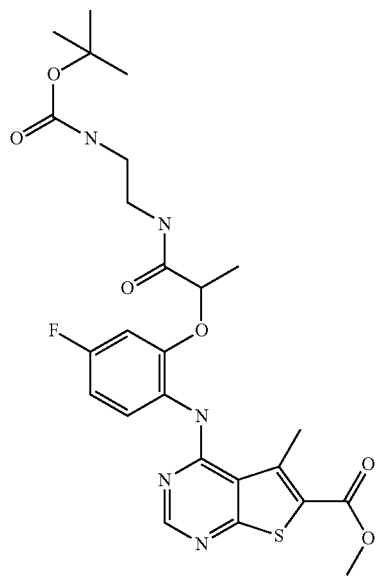 [SMILES: COC(=O)c1sc2ncnc(Nc3ccc(F)cc3OC(C)C(=O)NCCNC(=O)OC(C)(C)C)c2c1C]

Prepared analogously to example 56.1 using the product from 55 (170 mg) and tert-butyl N-(2-aminoethyl)carbamate (90 μl).

Yield: 135 mg
ESI mass spectrum: m/z=548 (M+H)⁺

58.2 4-{2-[1-(2-Amino-ethylcarbamoyl)-ethoxy]-4-fluoro-phenylamino}-5-methyl thieno[2,3-d]pyrimidine-6-carboxylic acid methyl ester

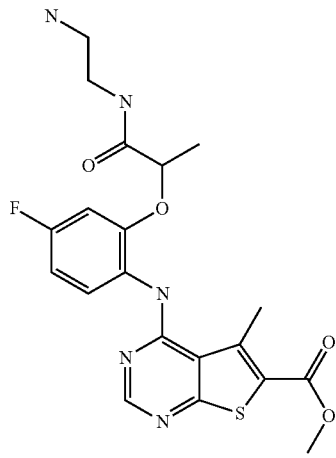 [SMILES: COC(=O)c1sc2ncnc(Nc3ccc(F)cc3OC(C)C(=O)NCCN)c2c1C]

Prepared analogously to example 56.2 using the product from 57.3 (170 mg).

Yield: 28 mg
ESI mass spectrum: m/z=448 (M+H)⁺
Retention time HPLC: 1.83 min
HPLC method: A_9

Compound 59

4-{2-[1-(2-Amino-ethylcarbamoyl)-ethoxy]-4-fluoro-phenylamino}-5-methyl-thieno[2,3-d]pyrimidine-6-carboxylic acid (2-hydroxy-ethyl)amide

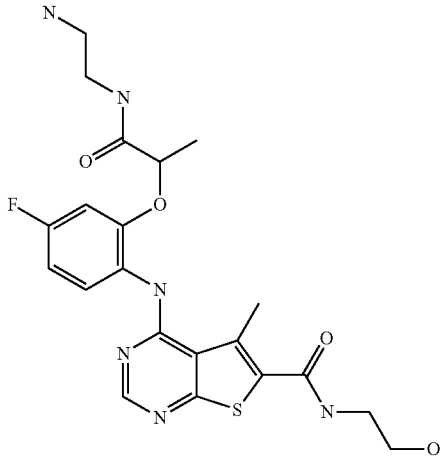 [SMILES: Cc1c(C(=O)NCCO)sc2ncnc(Nc3ccc(F)cc3OC(C)C(=O)NCCN)c12]

59.1 4-{2-[1-(2-tert-Butoxycarbonylamino-ethylcarbamoyl)-ethoxy]-4-fluoro-phenylamino}-5-methyl-thieno[2,3-d]pyrimidine-6-carboxylic acid

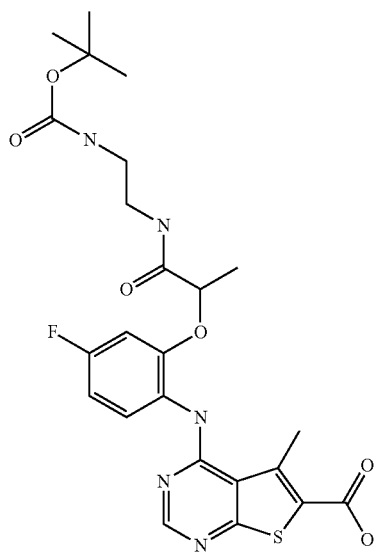 [SMILES: Cc1c(C(=O)O)sc2ncnc(Nc3ccc(F)cc3OC(C)C(=O)NCCNC(=O)OC(C)(C)C)c12]

Prepared analogously to example 57.1 using the product from 58 (90 mg).
Yield: 73 mg
ESI mass spectrum: m/z=534 (M+H)+

59.2 [2-(2-{5-Fluoro-2-[6-(-hydroxy-etyhlcabamoyl)-5-methyl-thieno[2,3-d]pyrimidin-4-ylamino]-phenoxy}-propionylamino]-ethyl]-carbamic acid tet-butyl ester

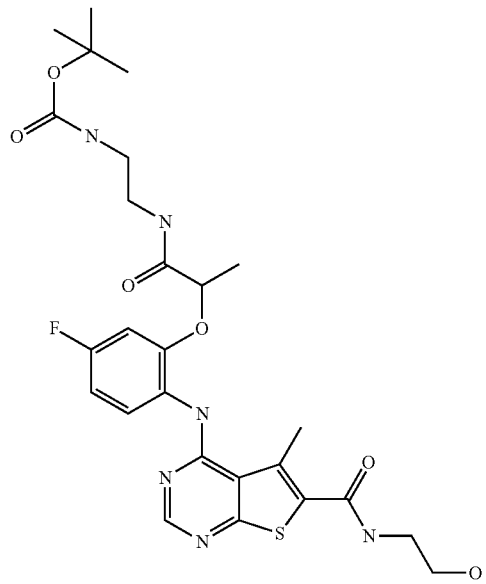 [SMILES: Cc1c(C(=O)NCCO)sc2ncnc(Nc3ccc(F)cc3OC(C)C(=O)NCCNC(=O)OC(C)(C)C)c12]

The product from 59.1 (73 mg) and TBTU (48 mg) were dissolved in DMF (1 ml). TEA (48 pp was added and the mixture was stirred for 5 min. at rt before ethanolamine (11 µl) was added. The mixture was stirred at rt overnight. The mixture was then diluted with methanol. Purification was achieved by chromatography.
Yield: 40 mg
ESI mass spectrum: m/z=577 (M+H)+
Retention time HPLC: 1.56 min
HPLC method: A_9

59.3 4-{2-[1-(2-Amino-ethylcarbamoyl)-ethoxy]-4-fluoro-phenylamino}-5-methyl-thieno[2,3-d]pyrimidine-6-carboxylic acid (2-hydroxy-ethyl)amide

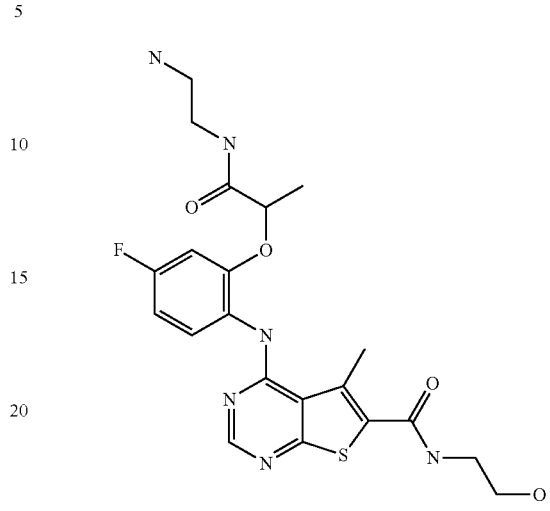

A mixture of the product from 59.2 (40 mg) and 25% trifluoroacetic acid in DCM (5 ml) was stirred at rt for 4 hours. Methanol and a solution of hydrochloric acid in methanol were added. Then the mixture was concentrated.
Yield: 7 mg
ESI mass spectrum: m/z=462 (M+H)+
Retention time HPLC: 1.96 min
HPLC method: A_9

Compound 60

4-[4-Fluoro-2-(2-hydroxy-1,2-dimethyl-propoxy)-phenylamino]-5-methyl-thieno[2,3-d]pyrimidine-6-carboxylic acid amide

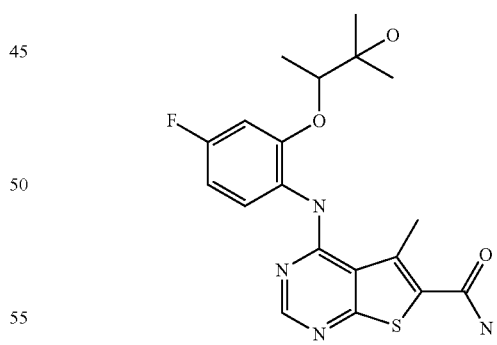

4-Chloro-5-methyl-thieno[2,3-d]pyrimidine-6-carboxylic acid amide (intermediate XXIV) (100 mg), intermediate XXVI (120 mg) and p-toluenesulfonic acid (5 mg) in dioxane (2 ml) were stirred at 100° C. for 6 hours. Then the mixture was filtrated. The solid was washed with methanol.
Yield: 145 mg
ESI mass spectrum: m/z=405 (M+H)+
Retention time HPLC: 1.245 min
HPLC method: M2-SB-C18

Compound 61

4-[2-(1-Ethylcarbamoyl-ethoxy)-4-fluoro-phenylamino}-5-methylthieno[2,3d]pyrimidine-6-carboxylic acid methyl ester

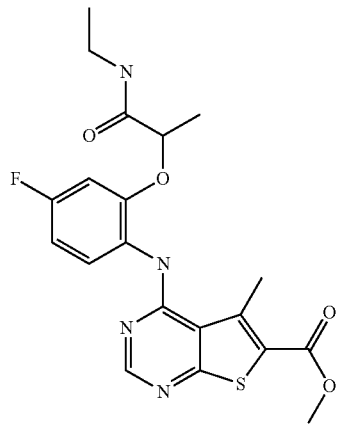 [SMILES: CCNC(=O)C(C)Oc1cc(F)ccc1Nc1ncnc2sc(C(=O)OC)c(C)c12]

The product from 55 (500 mg) and TBTU (400 mg) were dissolved in ACN (10 ml). TEA (430 µl) was added and the mixture was stirred for 20 min. at rt before Ethylamine (1.5 ml) was added. The mixture was stirred at rt overnight. Then the mixture was diluted with methanol. Purification was achieved by chromatography.

Yield: 360 mg
ESI mass spectrum: m/z=433 (M+H)⁺
Retention time HPLC: 1.89 min
HPLC method: A_9

The following compound was prepared analogously to example 61 using the product from 55 and the corresponding amine.

Compound 63

4-[2-Cyano-methyl-methoxy)-4-fluoro-phenylamino]-5-methyl-thieno[2,3-d]pyrimidine-6-carboxylic acid (2-dimethylamino-propy)-amide

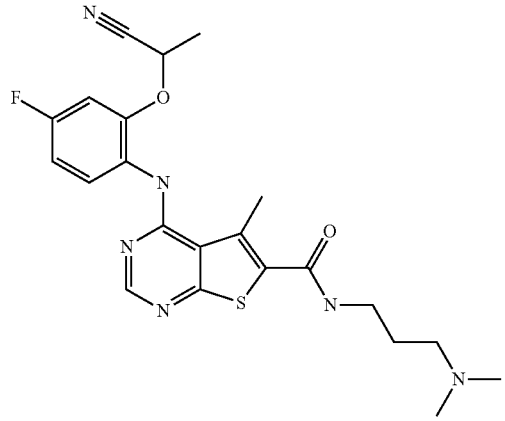 [SMILES: Cc1c(C(=O)NCCCN(C)C)sc2ncnc(Nc3ccc(F)cc3OC(C)C#N)c12]

63.1 4-(4-Fluoro-2-hydroxy-phenylamino)-5-methyl-thieno[2,3-d]pyrimidine-6-carboxylic acid

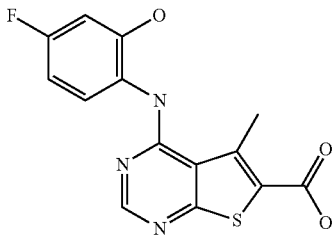

Intermediate III (333 mg), sodium hydroxide solution 1M (5 ml) in 10 ml methanol and 10 ml THF were stirred at rt overnight. Then the mixture was acidified with hydrochloric acid and filtrated.

Yield: 256 mg
ESI mass spectrum: m/z=320 (M+H)⁺
Retention time HPLC: 2.22 min
HPLC method: 004_CC_ZQ6

| | Structure | Name | Yield | Mass | Retention time | HPLC method | Amine |
|---|---|---|---|---|---|---|---|
| 62 | 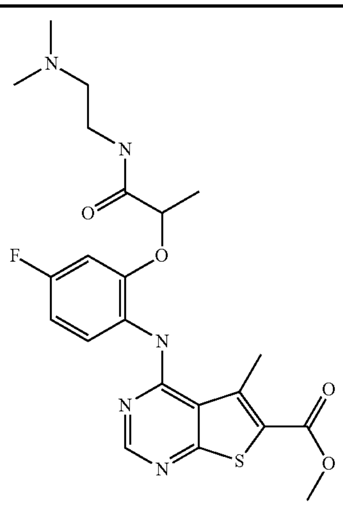 | 4-{2-[1-(2-Dimethylamino-ethylcabamoyl)-ethoxy]-4-fluoro-phenylamino}-5-methyl-thieno[2,3-d]pyrimidine-6-carboxylic acid methyl ester | 136 mg | 476 | 2.17 | A-4 | |

63.2 4-(4-Fluoro-2-hydroxy-chenylamino)-5-methyl-thieno[2,3-d]pyrimidine-6-carboxylic acid (3-dimethylamino-propyl)-amide

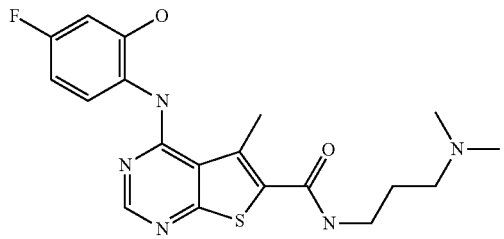 [SMILES: Cc1c(C(=O)NCCCN(C)C)sc2ncnc(Nc3ccc(F)cc3O)c12]

Prepared analogously to example 21.1 using the product from 63.1 (150 mg) and N,N-dimethyl-1,3-propanediamine (90 µl).
Yield: 157 mg
ESI mass spectrum: m/z=404 (M+H)$^+$
Retention time HPLC: 1.62 min
HPLC method: 004_CC_ZQ6

63.3 4-[2-Cyano-methyl-methoxy)-4-fluoro-phenylamino]-5-methyl-thieno[2,3-d]pyrimidine-6-carboxylic acid (2-dimethylamino-propy)-amide

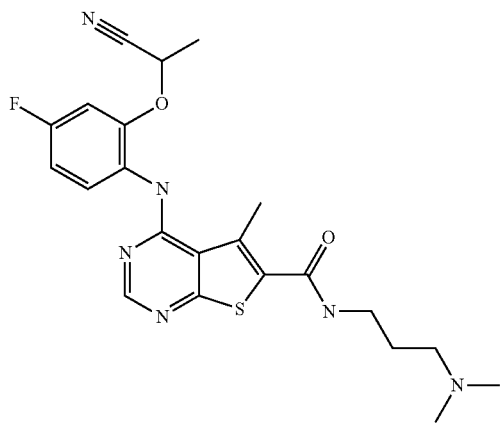 [SMILES: Cc1c(C(=O)NCCCN(C)C)sc2ncnc(Nc3ccc(F)cc3OC(C)C#N)c12]

To the product from 63.2 (157 mg) in DMF (4 ml) was added cesium carbonate (165 mg). After 5 min. 2-Bromopropionitrile (37 µl) was added and the mixture was stirred at rt overnight. Then the mixture was concentrated and diluted with DCM and water. The organic layer was seperated, dried and concentrated.
Yield: 130 mg
ESI mass spectrum: m/z=457 (M+H)$^+$
MNK$_2$-Inhibition Kinase Fluorescence Polarization Assays Assay Principle:

Inhibitory potency of compounds against Mnk1, Mnk2a and other kinases was assessed with assays based on a format known to those skilled in the art as the indirect (competitive) fluorescence polarization. The assay detection system comprises a small fluorophore-labeled phospho-peptide (termed ligand) bound to a phospho-specific antibody. The product generated by the kinase reaction competes with the ligand for antibody binding. Based on the larger molecular volume of the bound ligand, which results in a lower rotation rate in solution, its emitted light has a higher degree of polarization than the one from the free ligand.

Description of the Specific Homogenous Kinase Assay

Example 2a

Mnk1 and Mnk2a In Vitro Kinase Assay

As a source of enzyme, human Mnk1 and human Mnk2a were expressed as GST fusion proteins in *E. coli*, purified to >80% homogeneity by glutathione affinity chromatography and activated in vitro with pre-activated ERK2. In brief, the open reading frames of human Mnk1 and Mnk2a were amplified from cDNA using the forward/reverse primer pairs

| | |
|---|---|
| 5'TTTAGGATCCGTATCTTCTCAAAAGTTGG/ | SEQ ID NO: 1 |
| 5'CTGGGTCGACTCAGAGTGCTGTGGGCGG and | SEQ ID NO: 2 |
| 5'ACAGGGATCCGTGCAGAAGAAACCAGCC/ | SEQ ID NO: 3 |
| 5'GATGGTCGACTCAGGCGTGGTCTCCCACC | SEQ ID NO: 4 |

(utilized restriction sites underlined), respectively, and cloned into the BamHI and SalI sites of the vector pGEX-4T1 (Amersham, Sweden, cat. no. 27-4580-01). These constructs allow prokaryotic expression of Mnk1 or Mnk2a as fusion protein with a N-terminal glutathione S-transferase (GST) tag, referred to as GST-Mnk1 or GST-Mnk2a. The following expression and purification procedure was identical for GST-Mnk1 and GST-Mnk2a, referring in general to GST-Mnk, when not distinguishing between the two isoforms. Expression of GST-Mnk was in *E. coli* BL21 (Merck Biosciences, Germany, cat. no. 69449). Cells were grown in LB-Bouillon (Merck, Germany, cat. no. 1.10285) supplemented with 100 µg/ml ampicillin (Sigma, Germany, cat. no. A9518) at 37° C. When the culture had reached a density corresponding to an A$_{600}$ of 0.8, an equal volume of ice cold LB/ampicillin was added, the culture transferred to 25° C. and induced for 4 h with 1 mM isopropyl thiogalactoside (IPTG, Roth, Germany, cat. no. 2316.4). Cells harvested by centrifugation were resuspended in 10 ml lysis buffer (50 mM tris(hydroxymethyl)aminomethane hydrochloride (Tris/HCl, Sigma, Germany, cat. no. T5941) pH 7.5, 300 mM sodium chloride (NaCl, Sigma, Germany, cat. no. S7653), 5% (w/v) glycerol (Sigma, Germany, cat. no. G5516), 3 mM DTT dithiotreitol (DTT, Sigma, Germany, cat. no. D9779)) per gram wet weight cell pellet. Lysates were prepared by disruption of cells with a sonifier and subsequent clearing by centrifugation at 38000 g for 45 min at 4° C.

The lysate was applied to a GSTPrep FF 16/10 column (Amersham, Sweden, cat. no. 17-5234-01) equilibrated with lysis buffer. Removal of unbound material was with 3 column volumes (CV) lysis buffer. Elution was with 2 CV of elution buffer (50 mM Tris/HCl pH 7.5, 300 mM NaCl, 5% (w/v) glycerol, 20 mM glutathione (Sigma, Germany, cat. no. G4251)). Peak fractions were pooled and the protein transferred into storage buffer (50 mM Tris/HCl pH 7.5, 200 mM NaCl, 0.1 mM ethylene glycol-01-2600 bis(2-aminoethyl-ether)-N,N,N',N'-tetraacetic acid (EGTA, Aldrich, Germany, cat. no. 23, 453-2), 1 mM DTT, 10% (w/v) glycerol, 0.5 M sucrose (Sigma, Germany, cat. no. S0389) by gel filtration on a PD10 desalting column (Amersham, Sweden, cat. no. 17-0851-01). Aliquots were shock frozen in liquid nitrogen and stored at −80° C.

Activation of Mnk1 and Mnk2a was at a concentration of 2.5 μM of either purified GST-Mnk1 or GST-Mnk2a by incubation with 150 nM pre-activated NHis-ERK2 (see ERK2 assay for preparation) and 50 μM adenosine triphosphate (ATP, Sigma, cat. no. A2699) in a buffer comprising 20 mM N-(2-hydroxyethyl)piperazine-N'-(2-ethanesulfonic acid) (HEPES, Fluka, Germany, cat. no 54459)/potassium hydroxide (KOH, Roth, Germany, cat. no 6751.1) pH 7.4, 10 mM magnesium chloride ($MgCl_2$, Sigma, Germany, cat. no. M2670), 0.25 mM DTT, 0.05% (w/v) polyoxyethylene 20 stearylether (Brij 78, Sigma, Germany, cat. no. P4019) (HMDB buffer) for 45 min at 30° C. After the incubation, the preparation was aliquoted into single-use samples, shock frozen in liquid nitrogen, stored at −80° C. and utilized for Mnk1 or Mnk2a kinase assays as detailed below. The presence of activating kinase has been tested to not interfere with the Mnk activity assay.

SUBSTRATE: A carboxy-terminal amidated 12mer peptide with the sequence SEQ ID NO: 5 TATKSGSTTKNR, derived from the amino acid sequence around serine 209 of the eukaryotic translation initiation factor 4E (eIF4E) has been synthesized and purified by high performance liquid chromatography (HPLC) to >95% (Thermo, Germany). The serine residue phosphorylated by Mnk kinases is underlined.

LIGAND: The peptide TATKSG-pS-TTKNR (SEQ ID NO: 6), containing an amidated carboxy-terminus and conjugated at the amino-terminus with the oxazine derived fluorophore depicted below was synthesized and used as ligand.

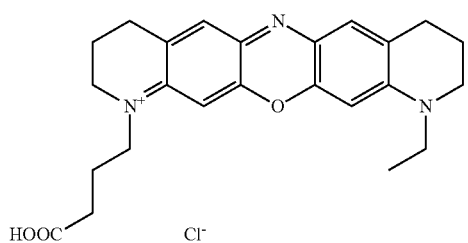 [SMILES: CCN1CCCc2cc3c(cc21)Oc1cc2c(cc1=N3)CCC[N+]=2CCCC(=O)O ; [Cl-]]

ANTIBODY: SPF New Zealand White Rabbits have been immunized according to standard protocols with the peptide NH2—CTATKSG-pS-TTKNR—CONH2 (SEC) ID NO: 7), coupled to keyhole limpet hemocyanin (KLH). The immune globulin G (IgG) fraction was purified from serum of boosted animals by techniques known in the art. In brief, serum was subjected to protein A affinity chromatography. Eluted material was precipitated at 50% cold saturated ammonium sulfate, pellets dissolved and desalted. The resulting material was appropriate for use in below described assay without further antigen-specific purification.

ASSAY SETUP: Inhibition of kinase activity of Mnk1 and Mnk2a was assessed with the same assay system, using pre-activated GST-Mnk1 or GST-Mnk2a, respectively. The kinase reaction contains 30 μM substrate peptide, 20 μM ATP, 60 nM ligand and one of either 25 nM pre-activated Mnk1 or 2.5 nM pre-activated Mnk2a. The reaction buffer conditions are 16 mM HEPES/KOH pH 7.4, 8 mM $MgCl_2$, 0.4 mM DTT, 0.08% (w/v) bovine serum albumin (BSA, Sigma, Germany, cat. no. A3059), 0.008% (w/v) Pluronic F127 (Sigma, Germany, cat. no. P2443), 3% (v/v) DMSO (Applichem, Germany, cat. no. A3006). The kinase reaction is at 30° C. for 40 min. The kinase reaction is terminated by addition of 0.67 reaction volumes of 1 μM antibody in 20 mM HEPES/KOH pH 7.4, 50 mM ethylenediaminetetraacetic acid, disodium salt (EDTA, Sigma, Germany, cat. no. E5134), 0.5 mM DTT, 0.05% (w/v) polyoxyethylene-sorbitan monolaureate (Tween 20, Sigma, Germany, cat. no. P7949). After 1 h equilibration time at room temperature, samples are subjected to fluorescence polarization measurement. The fluorescence polarization readout was generated on an Analyst AD multimode reader (Molecular Devices, Sunnyvale, Calif., USA) equipped with a DLRP650 dichroic mirror (Omega Opticals, Brattleboro, Vt., USA, cat. no. XF2035), a 630AF50 band pass filter (Omega Opticals, Brattleboro, Vt., USA, cat. no. XF1069) on the excitation and a 695AF55 band pass filter on the emission side (Omega Opticals, Brattleboro, Vt., USA, cat. no. XF3076).

The activity of Mnk proteins can be assayed also by other in vitro kinase assay formats. For example, suitable kinase assays have been described in the literature in Knauf et al., Mol Cell Biol. 2001 August; 21(16):5500-11 or in Scheper et al., Mol Cell Biol. 2001 February; 21(3):743-54. In general, Mnk kinase assays can be performed such that a Mnk substrate such as a protein or a peptide, which may or may not include modifications as further described below, or others are phosphorylated by Mnk proteins having enzymatic activity in vitro. The activity of a candidate agent can then be determined via its ability to decrease the enzymatic activity of the Mnk protein. The kinase activity may be detected by change of the chemical, physical or immunological properties of the substrate due to phosphorylation.

In one example, the kinase substrate may have features, designed or endogenous, to facilitate its binding or detection in order to generate a signal that is suitable for the analysis of the substrates phosphorylation status. These features may be, but are not limited to, a biotin molecule or derivative thereof, a glutathione-S-transferase moiety, a moiety of six or more consecutive histidine residues, an amino acid sequence or hapten to function as an epitope tag, a fluorochrome, an enzyme or enzyme fragment. The kinase substrate may be linked to these or other features with a molecular spacer arm to avoid steric hindrance.

In another example the kinase substrate may be labelled with a fluorophore. The binding of the reagent to the labelled substrate in solution may be followed by the technique of fluorescence polarization as it is described in the literature. In a variation of this example, a fluorescent tracer molecule may compete with the substrate for the analyte to detect kinase activity by a technique which is know to those skilled in the art as indirect fluorescence polarization.

In yet another example, radioactive gamma-ATP is used in the kinase reaction, and the effect of the test agent on the incorporation of radioactive phosphate in the test substrate is determined relative to control conditions.

It has been shown that the compounds of the invention exhibit low $IC_{50}$ values in in vitro biological screening assays as described in example 2a for inhibition of Mnk 1 and/or Mnk 2 kinase activity. The following table contains the test results for exemplary compounds.

| Example | MNK2 $IC_{50}$ [nM] |
| --- | --- |
| 1-2 | 52 |
| 1-3 | 342 |
| 1-4 | 294 |
| 1-5 | 459 |
| 2-1 | 70 |
| 2-2 | 41 |

-continued

| Example | MNK2 IC$_{50}$ [nM] |
|---|---|
| 2-3 | 50 |
| 2-4 | 23 |
| 3-1 | 41 |
| 3-2 | 204 |
| 3-3 | 18 |
| 3-4 | 261 |
| 3-5 | 443 |
| 4 | 3144 |
| 5 | 230 |
| 6-1 | 164 |
| 6-2 | 90 |
| 7 | 14 |
| 8-1 | — |
| 8-2 | 64 |
| 9-2 | 577 |
| 10-2 | 229 |
| 11-2 | 418 |
| 12 | 52 |
| 13 | 90 |
| 13-2 | 471 |
| 13-3 | 677 |
| 13-4 | 898 |
| 14 | 1017 |
| 15-2 | 174 |
| 16-2 | 8 |
| 16-3 | 74 |
| 16-4 | 44 |
| 17 | — |
| 18-2 | 691 |
| 19-1 | 1526 |
| 19-2 | 1166 |
| 20-1 | 142 |
| 20-2 | 25 |
| 20-3 | 59 |
| 21-2 | 15 |
| 21-3 | 11 |
| 21-4 | 54 |
| 21-5 | 42 |
| 21-6 | 12 |
| 21-7 | 24 |
| 21-8 | 20 |
| 22-3 | 296 |
| 23-1 | 78 |
| 23-2 | 6 |
| 23-3 | 4 |
| 23-4 | 8 |
| 23-5 | 13 |
| 23-6 | 10 |
| 23-7 | 17 |
| 23-8 | 8 |
| 23-9 | 7 |
| 23-10 | 7 |
| 24 | 7 |
| 25 | 12 |
| 26-3 | 790 |
| 27-2 | 33 |
| 27-3 | 58 |
| 27-4 | 73 |
| 28-3 | 26 |
| 28-4 | 78 |
| 28-5 | 93 |
| 29-3 | 86 |
| 29-4 | 288 |
| 30-2 | 20 |
| 30-3 | 18 |
| 30-4 | 48 |
| 30-5 | 57 |
| 31-3 | 77 |
| 31-4 | 19 |
| 31-5 | 11 |
| 31-6 | 13 |
| 31-7 | 20 |
| 32-1 | 267 |
| 32-2 | 19 |
| 32-3 | — |
| 32-4 | 13 |
| 32-5 | 8 |

-continued

| Example | MNK2 IC$_{50}$ [nM] |
|---|---|
| 32-6 | 23 |
| 32.7 | 5 |
| 32-8 | — |
| 32-9 | 13 |
| 32-10 | 18 |
| 32-11 | 14 |
| 32-12 | 12 |
| 32-13 | — |
| 32-14 | 65 |
| 32-15 | 78 |
| 32-16 | 66 |
| 32-17 | 16 |
| 32-18 | 30 |
| 32-19 | 23 |
| 32-20 | 19 |
| 32-21 | 8 |
| 32-22 | 36 |
| 32-23 | 26 |
| 32-24 | 25 |
| 32-25 | 13 |
| 32-26 | 7 |
| 32-27 | 7 |
| 32-28 | 3 |
| 32-29 | 170 |
| 32-30 | 56 |
| 32-31 | 146 |
| 32-32 | 27 |
| 32-33 | 65 |
| 32-34 | 69 |
| 32-35 | 35 |
| 32-36 | 25 |
| 32-37 | 8 |
| 32-38 | 26 |
| 32-39 | 35 |
| 32-40 | 13 |
| 32-41 | 25 |
| 32-42 | 12 |
| 32-43 | 12 |
| 32-44 | 6 |
| 32-45 | 11 |
| 33 | 47 |
| 33-4 | 16 |
| 34 | 54 |
| 34-4 | 15 |
| 35 | 12 |
| 36 | 29 |
| 36-1 | 35 |
| 36-2 | 42 |
| 36-3 | 26 |
| 36-4 | 44 |
| 36-5 | 25 |
| 36-6 | 55 |
| 36-7 | 27 |
| 36-8 | 19 |
| 36-9 | 63 |
| 36-10 | 32 |
| 36-11 | 45 |
| 36-12 | 31 |
| 36-13 | 54 |
| 36-14 | 64 |
| 36-15 | 24 |
| 36-16 | 22 |
| 36-17 | 46 |
| 36-18 | 26 |
| 36-19 | 14 |
| 37 | 4 |
| 38 | 6 |
| 39 | 19 |
| 40 | 20 |
| 41 | 31 |
| 42 | 70 |
| 43 | 62 |
| 44 | 24 |
| 45 | 20 |
| 46 | 84 |
| 47 | 125 |
| 48 | 12 |

-continued

| Example | MNK2 IC$_{50}$ [nM] |
|---|---|
| 49 | 8 |
| 50 | 13 |
| 51 | 10 |
| 52 | 25 |
| 53 | 7 |
| 54 | 11 |
| 55 | 5403 |
| 56 | 314 |
| 57 | 110 |
| 58 | 119 |
| 59 | 29 |
| 60 | 37 |
| 61 | 77 |
| 62 | 267 |
| 63 | 17 |

HPLC methods:
Method A_10
Waters ZQ 2000; Waters 1515 Pumpe; Waters PDA 996 Detektor; Waters 2747
Injektor
DAD 200-420 nm
mobile phases:
A: water with 0.10% formic acid
B: acetonitrile with 0.10% formic acid

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

Stationary phase: X-terra MS C18; 4.6×30 mm*2.5 μm
Method AC1
Waters ZQ 2000; Waters 1515 Pumpe; Waters PDA 996 Detektor; Waters 2747
Injektor
DAD 210-420 nm
mobile phases:
A: water with 0.10% formic acid
B: acetonitrile with 0.10% formic acid

| time in min | % A | % B | flow rate in ml/min |
|---|---|---|---|
| 0.00 | 95 | 5 | 1.00 |
| 0.10 | 95 | 5 | 1.00 |
| 3.10 | 2 | 98 | 1.00 |
| 4.50 | 2 | 98 | 1.00 |
| 5.00 | 95 | 5 | 1.00 |

Stationary phase: X-terra MS C18; 4.6×30 mm*2.5 μm
Method A_9
(pos/neg switch method)
Waters ZQ 2000; Waters 1515 Pumpe; Waters PDA 996 Detektor; Waters 2747
Injektor
DAD 200-420 nm
mobile phases:
A: water with 0.10% formic acid
B: acetonitrile with 0.10% formic acid

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

Stationary phase: X-terra MS C18; 4.6×30 mm*2.5 μm
Method C_SF_TFA_MeOH_P30V#004_CC_ZQ1
RP-HPLC MS analyses have been performed on a Waters ZQ2000 mass spectrometer,
HP1100 HPLC+DAD (Wavelength range (nm): 210 to 500) and Gilson 215 Autosampler.
Mobile Phases:
A: Water with 0.1% TFA
B: MeOH

| Time in min | % A | % B | Flowrate in ml/min |
|---|---|---|---|
| 0.00 | 80 | 20 | 2.00 |
| 1.7 | 0 | 100 | 2.00 |
| 2.50 | 0 | 100 | 2.00 |
| 2.60 | 80 | 20 | 2.00 |

Stationary phase: Waters, Sunfire, C18, 3.5 μm, 4.6×50 mm.
Column temp: 60° C.
Diode array detection is at the wavelength range of 210-500 nm.
Method A_4
Waters ZQ 2000; Waters 1515 Pumpe; Waters PDA 996 Detektor; Waters 2747
Injektor
DAD 200-420 nm
mobile phases:
A: water with 0.10% formic acid
B: acetonitrile with 0.10% formic acid

| time in min | % A | % B | flow rate in ml/min |
|---|---|---|---|
| 0.00 | 95 | 5 | 1.00 |
| 0.10 | 95 | 5 | 1.00 |
| 3.10 | 2 | 98 | 1.00 |
| 4.50 | 2 | 95 | 1.00 |
| 5.00 | 95 | 5 | 1.00 |

Stationary phase: X-terra MS C18; 4.6×30 mm*2.5 μm
Method amslstandard:
ZQ 2000MS; Waters 2996 PDA (210-600 nm); Waters 2525 pump; Waters 515 make up pump; Waters 2767 injector/fraction collector, Waters columns and fluidics organizer (CFO)
mobile phases:
A: water with 0.20% trifluoroacetic acid
B: Methanol

| time in min | % A | % B | flow rate in ml/min |
|---|---|---|---|
| 0.00 | 72 | 18 | 55.00 |
| 2.00 | 72 | 18 | 55.00 |
| 2.50 | 62 | 38 | 55.00 |
| 9.50 | 18 | 72 | 55.00 |
| 10.00 | 0 | 100 | 55.00 |
| 12.00 | 0 | 100 | 55.00 |
| 12.50 | 0 | 100 | 0 |

Stationary phase: X-terra MS C18; 30×100 mm*5 µm
Temperature 25° C.
Method Amslunpolar1:
ZQ 2000MS; Waters 2996 PDA (210-600 nm); Waters 2525 pump; Waters 515 make up pump; Waters 2767 injector/fraction collector, Waters columns and fluidics organizer (CFO)
mobile phases:
A: water with 0.20% trifluoroacetic acid
B: Methanol

| time in min | % A | % B | flow rate in ml/min |
|---|---|---|---|
| 0.00 | 59 | 41 | 55.00 |
| 2.00 | 59 | 41 | 55.00 |
| 2.50 | 49 | 51 | 55.00 |
| 9.50 | 5 | 95 | 55.00 |
| 10.00 | 0 | 100 | 55.00 |
| 12.00 | 0 | 100 | 55.00 |
| 12.50 | 0 | 100 | 0 |

Stationary phase: X-terra MS C18; 30×100 mm*5 µm
Temperature 25° C.
Method 002_CC_ZQ4
RP-HPLC MS analyses have been performed on a Waters ZQ2000 mass spectrometer,
HP1100 HPLC+DAD (Wavelength range (nm): 210 to 500) and
Gilson 215 Autosampler.
Mobile Phases:
A: Water with 0.1% TFA
B: MeOH

| Time in min | % A | % B | Flowrate in ml/min |
|---|---|---|---|
| 0.00 | 95 | 5 | 1.50 |
| 1.3 | 0 | 100 | 1.50 |
| 2.50 | 0 | 100 | 1.50 |
| 2.60 | 95 | 5 | 1.50 |

Stationary phase: Waters, Sunfire, C18, 3.5 µm, 4.6×50 mm.
Column temp: constant at 40° C.
Diode array detection is at the wavelength range of 210-500 nm.
Method 003_CC_ZQ6
RP-HPLC MS analyses have been performed on a Waters ZQ2000 mass spectrometer, Alliance 2695, PDA2996
HP1100 HPLC+DAD (Wavelength range (nm): 210 to 500) and
As 2700
Mobile Phases:
A: Water with 0.1% TFA
B: MeOH

| Time in min | % A | % B | Flowrate in ml/min |
|---|---|---|---|
| 0.00 | 95 | 5 | 1.50 |
| 1.3 | 0 | 100 | 1.50 |
| 3.00 | 0 | 100 | 1.50 |
| 3.40 | 95 | 5 | 1.50 |

Stationary phase: Waters, Sunfire, C18, 3.5 µm, 4.6×50 mm.
Column temp: constant at 40° C.
Diode array detection is at the wavelength range of 210-500 nm.

Method 004_CC_ZQ6
RP-HPLC MS analyses have been performed on a Waters ZQ2000 mass spectrometer, Alliance 2695, PDA2996
DAD (Wavelength range (nm): 210 to 500) and 2700 AS
Mobile Phases:
A: Water with 0.1% TFA
B: MeOH

| Time in min | % A | % B | Flowrate in ml/min |
|---|---|---|---|
| 0.00 | 80 | 20 | 2 |
| 1.7 | 0 | 100 | 2 |
| 2.5 | 0 | 100 | 2 |
| 2.6 | 80 | 20 | 2 |

Stationary phase: Waters, Sunfire, C18, 3.5 µm, 4.6×50 mm.
Column temp: 60° C.
Diode array detection is at the wavelength range of 210-500 nm.
Method 004_CC_ZQ7
RP-HPLC MS analyses have been performed on a Waters ZQ2000 mass spectrometer,
DAD (Wavelength range (nm): 210 to 500) and 2700 AS
Mobile Phases:
A: Water with 0.15% TFA
B: MeOH

| Time in min | % A | % B | Flowrate in ml/min |
|---|---|---|---|
| 0.00 | 95 | 5 | 1.5 |
| 1.5 | 95 | 5 | 1.5 |
| 2.0 | 0 | 100 | 1.5 |

Stationary phase: Xbridge C18, 3.5 µm, 4.6×50 mm.
Column temp: 40° C.
Diode array detection is at the wavelength range of 210-500 nm.
Method 003_CC_ZQ7
RP-HPLC MS analyses have been performed on a Waters ZQ2000 mass spectrometer,
DAD (Wavelength range (nm): 210 to 500) and 2700 AS
Mobile Phases:
A: Water with 0.032% NH4OH
B: MeOH

| Time in min | % A | % B | Flowrate in ml/min |
|---|---|---|---|
| 0.00 | 95 | 5 | 1.5 |
| 1.5 | 95 | 5 | 1.5 |
| 2.0 | 0 | 100 | 1.5 |

Stationary phase: Xbridge C18, 3.5 µm, 4.6×50 mm.
Column temp: 40° C.
Diode array detection is at the wavelength range of 210-500 nm.
Method 007_CC_ZQ5
RP-HPLC MS analyses have been performed on a Waters ZQ2000 mass spectrometer, Alliance 2790
DAD (Wavelength range (nm): 210 to 500) and 2700 AS
Mobile Phases:
A: Water with 0.1% TFA
B: MeOH

| Time in min | % A | % B | Flowrate in ml/min |
| --- | --- | --- | --- |
| 0.00 | 80 | 20 | 2 |
| 1.7 | 0 | 100 | 2 |
| 2.5 | 0 | 100 | 2 |
| 2.6 | 80 | 20 | 2 |

Stationary phase: Waters, Sunfire C18, 3.5 µm, 4.6×50 mm.
Column temp: 60° C.
Diode array detection is at the wavelength range of 210-500 nm.
Method 007_CC_ZQ7
RP-HPLC MS analyses have been performed on a Waters ZQ2000 mass spectrometer, Alliance 2790
DAD (Wavelength range (nm): 210 to 500) and 2700 AS
Mobile Phases:
A: Water with 0.1% TFA
B: MeOH

| Time in min | % A | % B | Flowrate in ml/min |
| --- | --- | --- | --- |
| 0.00 | 80 | 20 | 2 |
| 1.7 | 0 | 100 | 2 |
| 2.5 | 0 | 100 | 2 |
| 2.6 | 80 | 20 | 2 |

Stationary phase: Waters, Sunfire C18, 35 µm, 4.6×50 mm.
Column temp: 60° C.
Diode array detection is at the wavelength range of 210-500 nm.

Method M2-SB-C18
RP-HPLC MS analyses have been performed on a Agilent 1200, MS G6140A, binare Pumpe, DAD 190-400 nm
Mobile Phases:
A: Water with 0.1% TFA
B: MeOH

| Time in min | % A | % B | Flowrate in ml/min |
| --- | --- | --- | --- |
| 0.00 | 90 | 10 | 3 |
| 1.8 | 0 | 100 | 3 |
| 2.0 | 0 | 100 | 3 |
| 2.15 | 90 | 10 | 3 |
| 2.35 | 90 | 10 | 3 |

Stationary phase: Agilent, Stable Bond SB-C18, 1.8 µm, 4.6×30 mm.
Diode array detection is at the wavelength range of 190-400 nm.

| Method W001_001 | | | | |
| --- | --- | --- | --- | --- |
| column: Supplier | XBridge C18, 4.6 × 30 mm, 2.5 µm Waters | | | |
| time [min] | % Sol [H2O, 0.1% TFA] | % Sol [Methanol, 0.1% TFA] | Flow [ml/min] | Temp [° C.] |
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4 | 60 |
| 2.35 | 0 | 100 | 4 | 60 |

The invention claimed is:

1. A compound of Formula (I)

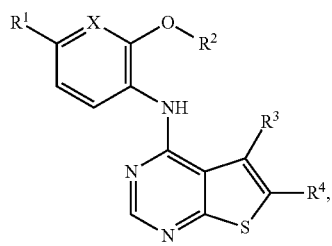

(I)

wherein

X is CH or N, $R^1$ is a halogen atom or CN or an $C_{1-3}$alkyl or $CONH_2$ group, if X is CH, or $R^1$ is hydrogen if X=N, $R^2$ is a straight-chained or branched $C_{1-6}$ alkyl group which is independently substituted with one or two fluorine atoms, or one or two trifluoromethyl, tetrahydropyranyl, cyclopropyl, $H_2N$—CO—, $R^5$NHCO— or $(R^5)_2$N—CO— groups, wherein the above-mentioned cyclopropyl group may be substituted with one or two F or —$CH_2$—CN, and wherein the two $R^5$ groups together with the N atom to which they are attached may form a 4- to 8-membered ring, in which a carbon atom may be replaced by a O, S, SO, SO₂ and/or which may be substituted with OH, NH₂, N(C₁₋₃-alkyl)₂, NH(C₁₋₃ alkyl), CF₃ or C₁₋₃-alkyl, or a straight-chained or branched C₂₋₆ alkyl group which is independently substituted in position 2 to 6 with one or two hydroxy, C₁₋₃ alkoxy, amino, CN, RNH—, (R⁵)₂N—, R⁵OCONH—, R⁵CONH—, R⁵SO₂NH—, R⁵NHCONH— groups, wherein R⁵ is a C₁₋₅ alkyl group, each optionally substituted with one CF₃, NH₂, NH(C₁₋₃ alkyl), N(C₁₋₃-alkyl)₂ or MeO— group, and wherein the hydrogen atoms of any of the above-mentioned NH moiety may be replaced by methyl, R³ is a C₁₋₂ alkyl group and R⁴ is a carboxy, —CONH₂, —CONHR⁷, —CONH—OR⁷, —CONH—SO₂R⁷ or —CO—NH-L-R⁶ group, wherein L is a —(CH₂)ₙ—, —CH₂—C≡C—CH₂—, or

wherein * indicates the point of attachment to the rest of the molecule,

R⁶ is OH, —NH₂, —NHR⁷, —N(R⁷)₂, —NH—CO₂R⁷ or a 3- to 6-membered cyclic amine, n is 2 or 3 and R⁷ is C₁₋₄ alkyl, or a salt thereof.

2. A compound of Formula (I) according to claim 1, wherein

R³ is methyl, or a pharmaceutically acceptable salt thereof.

3. A compound of Formula (I) according to claim 1, wherein

X is CH and

R¹ is a fluorine atom, or a pharmaceutically acceptable salt thereof.

4. A compound of Formula (I) according to claim 1, wherein

R² is selected from:

(dimethylamino)-carbonylmethyl, 2-amino-ethyl, 1-(trifluoromethyl)-ethyl;

isopropyl substituted in position 2 with amino or tert-butyloxycarbonylamino; 2,2'-diamino-isopropyl, 2,2'-difluoro-isopropyl, 2,2'-di-(ethoxy)-isopropyl, 2,2'-bis-(tert-butyloxycarbonylamino)-isopropyl, 2-[2'-(trifluoromethyl)-ethylamino]-isopropyl, 3-amino-1-methyl-propyl, 3-(dimethylamino)-1-methyl-propyl, 3-hydroxy-1,3-dimethyl-butyl, 1,3-difluoropropan-2-yl, 1,1,1-trifluoropropan-2-yl or 1,1-difluoroethyl, or pharmaceutically acceptable salt thereof.

5. A compound of Formula (I) according to claim 1, wherein

R⁴ is selected from:

carboxy, aminocarbonyl or N—(C₁₋₃ alkyl)-aminocarbonyl group, wherein the alkyl moiety of the above-mentioned N—(C₁₋₃ alkyl)-aminocarbonyl group may optionally be terminally substituted with a hydroxy, amino, N—(C₁₋₃ alkyl)-amino or N,N—[di-(C₁₋₃ alkyl)]-amino group, or a pharmaceutically acceptable salt thereof.

6. A compound of Formula (I) according to claim 1, wherein

R⁴ is selected from:

aminocarbonyl, N-methyl-aminocarbonyl, N-(2-hydroxy-ethyl)-aminocarbonyl, N-[2-(dimethylamino)-ethyl]-aminocarbonyl, N-[3 (dimethylamino)-propyl]-aminocarbonyl, and carboxy, or a pharmaceutically acceptable salt thereof.

7. The compound of Formula (I) according to claim 1 selected from the group consisting of:

b) 4-(2-(1-Aminopropan-2-yloxy)-4-fluorophenylamino)-N-5-methylthieno[2,3-d]pyrimidine-6-carboxamide, d) 4-(2-(1-Aminopropan-2-yloxy)-4-fluorophenylamino)-5-methylthieno[2,3-d]pyrimidine-6-carboxamide, e) 4-(2-(1-Aminopropan-2-yloxy)-4-fluorophenylamino)-5-methylthieno[2,3-d]pyrimidine-6-carboxylic acid, h) 4-(2-(4-Aminobutan-2yloxy)pyridin-3ylamino)-5-methylthieno[2,3-d]pyrimidine-6-carboxylic acid, i) N-(3-(Dimethylamino)propyl)-4-(4-fluoro-2-(4-hydroxy-4-methylpentan-2-yloxy)phenylamino)-5-methylthieno[2,3-d]pyrimidine-6-carboxamide, j) 5-Methyl-4-(2-(1,1,1-trifluoropropan-2yloxy)pyridin-3-ylamino)thieno[2,3-d]pyrimidine-6-carboxylic acid, k) 5-Methyl-4-(2-(1,1,1-trifluoropropan-2yloxy)pyridin-3-ylamino)thieno[2,3-d]pyrimidine-6-carboxamide, l) N-Methyl-5-methyl-4-(2-(1,1,1-trifluoropropan-2-yloxy)pyridin-3-ylamino)thieno[2,3-d]pyrimidine-6-N-methylcarboxamide, m) 4-(2-(1,3-Difluoropropan-2-yloxy)-4-fluorophenylamino)-5-methyl-thieno[2,3-d]pyrimidine-6-carboxamide, n) N-Methyl-4-(2-(1,3-difluoropropan-2-yloxy)-4-fluorophenylamino)-5-methyl-thieno[2,3 d]pyrimidine-6-carboxamide, o) 4-(2-(1,3-Difluoropropan-2-yloxy)-4-fluorophenylamino)-N-(3-(dimethylamino)propyl)-5-methyl-thieno[2,3-d]pyrimidine-6-carboxamide, p) 4-(2-(1,3-Difluoropropan-2-yloxy)-4-fluorophenylamino)-N-(2-(dimethylamino)ethyl)-5-methylthieno[2,3-d]pyrimidine-6-carboxamide, q) 4-(2-(1,3-Difluoropropan-2-yloxy)-4-fluorophenylamino)-N-(2-(hydroxyethyl)-5-methylthieno[2,3-d]pyrimidine-6-carboxamide, r) 4-(2-(1,3-Difluoropropan-2-yloxy)-4-fluorophenylamino)-5-methyl-N-(3-(pyrrolidin-1-yl)propyl)thieno[2,3-d]pyrimidine-6-carboxamide, s) N-((trans)-2-Aminocyclopropyl)-4-(2-(1,3-difluoropropan-2-yloxy)-4-fluorophenylamino)-5-methylthieno[2,3-d]pyrimidine-6-carboxamide, t) 4-(2-(2-Fluoropropoxy)pyridin-3-ylamino)-N-(2-hydroxyethyl)-5-methylthieno[2,3-d]pyrimidine-6-carboxamide, u) 4-(2-(2,2-Difluoroethoxy)pyridin-3-ylamino)-5-methylthieno[2,3-d]pyrimidine-6-carboxylic acid, v) 4-(2-(2,2-Difluoroethoxy)pyridin-3-ylamino)-5-methyl-thieno[2,3-d]pyrimidine-6-carboxamide, w) 4-(2-(2,2-Difluoroethoxy)pyridin-3-ylamino)-N-(3-(dimethylamino)propyl)-5-methylthieno[2,3-d]pyrimidine-6-carboxamide, and x) 4-(2-(1-(Ethylamino)-1-oxopropan-2-yloxy)-4-fluorophenylamino)-N,5-dimethylthieno[2,3-d]pyrimidine-6-carboxamide, or a pharmaceutically acceptable salt thereof.

8. A pharmaceutically acceptable salt of a compound according to claim 1.

9. A pharmaceutical composition comprising a compound according to claim 1 or a pharmaceutically acceptable salt thereof and optionally a pharmaceutically acceptable carrier.

10. The pharmaceutical composition according to claim 9 further comprising an additional therapeutic agent.

11. The pharmaceutical composition according to claim 10 wherein the additional therapeutic agent is selected from an antidiabetic agent, a lipid lowering agent, a cardiovascular agent, an antihypertensive agent, a diuretic agent, a thrombocyte aggregation inhibitor, an antineoplastic agent and an anti-obesity agent.

* * * * *